United States Patent
Francis et al.

(10) Patent No.: US 9,969,677 B2
(45) Date of Patent: *May 15, 2018

(54) HISTONE ACETYLTRANSFERASE MODULATORS AND USES THEREOF

(75) Inventors: Yitshak Francis, New York, NY (US);
Mauro Fa, New York, NY (US);
Ottavio Arancio, New York, NY (US);
Jole Fiorito, New York, NY (US);
Shixian Deng, White Plains, NY (US);
Donald W. Landry, New York, NY (US); Michal Luzac, New York, NY (US); Yan Feng, Shanghai (CN)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1207 days.

This patent is subject to a terminal disclaimer.

(21) Appl. No.: 13/996,483

(22) PCT Filed: Dec. 22, 2011

(86) PCT No.: PCT/US2011/066851
§ 371 (c)(1),
(2), (4) Date: Jul. 31, 2013

(87) PCT Pub. No.: WO2012/088420
PCT Pub. Date: Jun. 28, 2012

(65) Prior Publication Data
US 2017/0121276 A1    May 4, 2017

Related U.S. Application Data

(60) Provisional application No. 61/426,033, filed on Dec. 22, 2010, provisional application No. 61/539,697, filed on Sep. 27, 2011, provisional application No. 61/541,706, filed on Sep. 30, 2011.

(51) Int. Cl.
| | |
|---|---|
| *C07C 217/22* | (2006.01) |
| *C07D 209/48* | (2006.01) |
| *C07D 295/088* | (2006.01) |
| *C07D 265/14* | (2006.01) |

(52) U.S. Cl.
CPC .......... *C07C 217/22* (2013.01); *C07D 209/48* (2013.01); *C07D 265/14* (2013.01); *C07D 295/088* (2013.01)

(58) Field of Classification Search
CPC .................................................. C07C 217/22
USPC ...................................................... 514/230.5
See application file for complete search history.

(56) References Cited

U.S. PATENT DOCUMENTS

| | | | |
|---|---|---|---|
| 3,254,120 A | 5/1966 | Albin et al. | |
| 3,591,684 A | 7/1971 | Chupp et al. | |
| 3,671,630 A | 6/1972 | Carroll et al. | |
| 3,678,111 A | 7/1972 | Houlihan | |
| 4,088,770 A | 5/1978 | Paget, Jr. | |
| 4,118,332 A | 10/1978 | Apostolatos et al. | |
| 5,304,532 A | 4/1994 | Munro et al. | |
| 5,430,062 A | 7/1995 | Cushman et al. | |
| 5,565,325 A | 10/1996 | Blake | |
| 5,712,171 A | 1/1998 | Zambias et al. | |
| 5,814,646 A | 9/1998 | Heinz et al. | |
| 7,332,629 B2 * | 2/2008 | Kundu .................. | C07C 235/64 558/415 |
| 2005/0009163 A1 | 1/2005 | Tong et al. | |
| 2005/0227915 A1 | 10/2005 | Steffan et al. | |
| 2006/0014811 A1 | 1/2006 | Muto et al. | |
| 2006/0019958 A1 | 1/2006 | Muto et al. | |
| 2006/0167107 A1 | 7/2006 | Kundu et al. | |
| 2007/0042997 A1 | 2/2007 | Itai et al. | |
| 2007/0265296 A1 | 11/2007 | Dalton et al. | |
| 2008/0300205 A1 | 12/2008 | Tsai et al. | |
| 2009/0076155 A1 | 3/2009 | Kundu et al. | |
| 2009/0163545 A1 | 6/2009 | Goldfarb | |
| 2009/0264414 A1 | 10/2009 | Andersen et al. | |
| 2010/0168084 A1 | 7/2010 | Huber et al. | |
| 2010/0311616 A1 | 12/2010 | Ozawa et al. | |
| 2011/0046154 A1 | 2/2011 | Roux et al. | |
| 2011/0081403 A1 | 4/2011 | Templeton | |
| 2013/0121919 A1 * | 5/2013 | Feng .................... | C07C 235/64 424/9.2 |

FOREIGN PATENT DOCUMENTS

| | | |
|---|---|---|
| CN | 101698651 A | 4/2010 |
| DE | 4428380 A1 | 2/1996 |
| EP | 1574504 A1 | 9/2005 |
| EP | 1649852 A1 | 4/2006 |

(Continued)

OTHER PUBLICATIONS

Japanese Office Action dated Sep. 16, 2015 for co-pending JP Application No. 2013-546423; 9 pages (with English translation).
International Search Report dated May 1, 2012 for related WO Application No. PCT/US2011/066851; 3 pages.
Coombs et al., "Synthesis and antiinflammatory activity of tert-aminomethylbenzophenones," J. Med. Chem., 14(11), pp. 1072-1074 (1971).
Middleton et al., "Designing rapid onset selective serotonin re-uptake inhibitors. 2: structure-activity relationships of substituted (aryl)benzylamines," Bioorg. Med. Chem. Lett., 18, pp. 4018-4021 (2008).

(Continued)

*Primary Examiner* — Nizal S Chandrakumar
(74) *Attorney, Agent, or Firm* — Wilmer Cutler Pickering Hale and Dorr LLP

(57) ABSTRACT

The invention provides compounds and compositions comprising compounds that modulate histone acyl transferase (HAT). The invention further provides methods for treating neurodegenerative disorders, conditions associated with accumulated amyloid-beta peptide deposits, Tau protein levels, and/or accumulations of alpha-synuclein as well as cancer by administering a compound that modulates HAT to a subject.

18 Claims, 9 Drawing Sheets

(56) References Cited

FOREIGN PATENT DOCUMENTS

| | | |
|---|---|---|
| GB | 728098 A | 4/1955 |
| GB | 1217868 A | 12/1970 |
| GB | 1436306 A | 5/1976 |
| JP | 55-129256 | 10/1980 |
| JP | 56-087501 | 7/1981 |
| JP | 56-087502 | 7/1981 |
| JP | 2002249473 A | 9/2002 |
| JP | 55-41202 B2 | 7/2014 |
| RU | 02370484 C1 | 10/2009 |
| WO | WO-91/05058 | 4/1991 |
| WO | WO-1992012961 A1 | 8/1992 |
| WO | WO-93/20242 | 10/1993 |
| WO | WO-94/18318 | 8/1994 |
| WO | WO-95/18972 | 7/1995 |
| WO | WO-96/22529 | 7/1996 |
| WO | WO-1997045111 A1 | 12/1997 |
| WO | WO-1998037068 A1 | 8/1998 |
| WO | WO-99/07409 | 2/1999 |
| WO | WO-99/32619 | 7/1999 |
| WO | WO-1999055663 A1 | 11/1999 |
| WO | WO-1999065449 A2 | 12/1999 |
| WO | WO-00/01846 | 1/2000 |
| WO | WO-00/44895 | 8/2000 |
| WO | WO-00/44914 | 8/2000 |
| WO | WO-200062778 | 10/2000 |
| WO | WO-2001000566 | 1/2001 |
| WO | WO-01/29058 | 4/2001 |
| WO | WO-01/36646 | 5/2001 |
| WO | WO-2001092288 | 12/2001 |
| WO | WO-2003103657 | 12/2003 |
| WO | WO-2004006858 A2 | 1/2004 |
| WO | WO-2004006906 A2 | 1/2004 |
| WO | WO-2004041256 A2 | 5/2004 |
| WO | WO-2004/052871 | 6/2004 |
| WO | WO-2004/053140 | 6/2004 |
| WO | WO2004/053140 A2 | 6/2004 |
| WO | WO-2005/080377 | 9/2005 |
| WO | WO-2005/121119 A1 | 12/2005 |
| WO | WO-2006084246 A2 | 8/2006 |
| WO | WO-2006132583 A1 | 12/2006 |
| WO | WO-2007008541 A2 | 1/2007 |
| WO | WO-2007101710 A1 | 9/2007 |
| WO | WO-2009/010454 A2 | 1/2009 |
| WO | WO-2009/016088 A1 | 2/2009 |
| WO | WO-2009/044410 A1 | 4/2009 |
| WO | WO-2011/072243 A1 | 6/2011 |

OTHER PUBLICATIONS

Abel et al., "Epigenetic targets of HDAC inhibition in neurodegenerative and psychiatric disorders," Current Opinion in Pharmacology, vol. 8, pp. 57-64 (2008).
Alamed, J., et al., "Two-day radial-arm water maze learning and memory task; robust resolution of amyloid-related memory deficits in transgenic mice," Nature Protocols, vol. 1, No. 4, pp. 1671-1679 (2006).
Alarcon, JM et al., "Chromatin acetylation, Memory, and LTP Are Impaired in CBP+/− Mice: A Model for the Cognitive Deficit in Rubinstein-Taybi Syndrome and Its Amelioration" Neuron, vol. 42, No. 6, pp. 947-959 (Jun. 24, 2004).
Atherton, E., et al., "Solid phase peptide synthesis: A practical approach," Oxford Press, 1989, 7 pgs.
Bach, M.E., et al., "Age-related defects in spatial memory are correlated with defects in the late phase of hippocampal long-term potential in vitro and are attenuated by drugs that enhance the cAMP signaling pathway," Proc. Natl. Acad. Sci. USA, Apr. 1999, vol. 96, pp. 5280-5285.
Bailey, C.H., et al., "Morphological basis of long-term habituation and sensitization in aplysia," Science, Apr. 1983, 220(4592): pp. 91-93.
Balasubramanyam, K., et al., "Small molecule modulators of histone acetyltransferase p300," J. Biol. Chem, 2003, 278(21): 19134-19140.

Baltrons, M.A., et al., "Regulation of NO-dependent cyclic GMP formation by inflammatory agents in neural cells," Toxicol Lett., 2003, 139(2-3): pp. 191-198.
Baratti, C.M., et al., "Effects of sildenafil on long-term retention of an inhibitory avoidance response in mice," Behav Pharmacol., 1999, 10(8): pp. 731-737.
Bass, B.L., "RNA interference: the short answer," Nature, 2001, vol. 411, pp. 428-429.
Berge, SM et al., "Pharmaceutical Salts" Journal of Pharmaceutical Sciences, vol. 66, No. 1, pp. 1-19 (Jan. 1977).
Biel, M., et al., "Epigenetics—an epicenter of gene regulation: histones and histone-modifying enzymes," Angew Chem Int Ed Engl, 2005, 44(21): pp. 3186-3216.
Bliss, T.V.P., et al., "A synaptic model of memory: long-term potentiation in the hippocampus," Nature, 1993, 361(6407): pp. 31-39.
Blondelle, S.E., et al., "Novel antimicrobial compounds indentified using synthetic combinatorial library technology," Tib Tech, 1996, vol. 14, pp. 60-65.
Bolden, J.E., et al., "Anticancer activities of histone deacetylase inhibitors," Nature Reviews Drug Discovery, 2006, vol. 5, pp. 769-784.
Bon, C.L.M., et al., "On the role of nitric oxide in hippocampal long-term potentiation," J Neurosci, 2003, 23(5): pp. 1941-1948.
Bordoli, L., et al., "Plant orthologs of p300/CMP: conservation of a core domain in metazoan p300/CMP acetyltransferase-related proteins," Nucleic Acids Res, 2001, vol. 29, pp. 589-597.
Bourtchuladze, R. et al., "Deficient Long-Term Memory in Mice with a Targeted Mutation of the cAMP-Responsive Element-Binding Protein" Cell, vol. 79, No. 1, pp. 59-68 (Oct. 7, 1994).
Bowers, E.M., et al., "Virtual ligand screening of the p300/CBP histone acetyltransferase: identification of a selective small molecule inhibitor," Chem Biol., May 2010, 17(5): pp. 471-482.
Brenner, S., et al., "Encoded combinatorial chemistry," Proc Natl Acad Sci USA, Jun. 1992, vol. 89, pp. 5381-5383.
Bunin, B.A., et al., "The combinatorial synthesis and chemical and biological evaluation of a 1,4-benzodiazepine library," Natl Acad Sci USA, Jan. 1994, vol. 91, pp. 4708-4712.
Caccia, S. et al., "Disposition and metabolism of minaprine in the rat," Xenobiotica, vol. 15, No. 12, pp. 1111-1119 (Dec. 1985).
Cao, X., et al., "A transcriptively active complex of APP with Fe65 and histone acetyltransferase Tip60.," Science, 2001, vol. 293, pp. 115-120.
Chapman, P.F., et al., "Impaired synaptic plasticity and learning in aged amyloid precursor protein transgenic mice," Nat Neurosci, 1999, 2(3): pp. 271-276.
Chee, F.C., et al., "An efficient synthesis of (±)-panduratin A and (±)-isopanduratin A, inhibitors of dengue-2 viral activity," Tetrahedron Letters, vol. 51, pp. 495-498 (2010).
Chen, Q., et al., "Impairment of hippocampal long-term potentiation by alzheimer amyloid β-peptides," J Neurosci Res, 2000, 60: pp. 65-72.
Christian, R.B., et al., "Simplified methods for construction, assessment and rapid screening of peptide libraries in bacteriophage," J Mol Biol, vol. 227, pp. 711-718 (1992).
Cleary, J.P., et al., "Natural oligomers of the amyloid-β protein specifically disrupt cognitive function," Nat Neurosci, 2005, 8: pp. 79-84.
Colton, C.A., et al., "NO synthase 2 (NOS2) deletion promotes multiple pathologies in a mouse model of alzheimer's disease," Proceedings of the Natl Acad of Sci USA, 2006, vol. 103, pp. 12867-12872.
Contestabile, A. et al., "Brain Nitric Oxide and Its Dual Role in Neurodegeneration/Neuroprotection: Understanding Molecular Mechanisms to Devise Drug Approaches" Current Medical Chemistry, vol. 10, pp. 2147-2174 (Oct. 2003).
International Search Report and Written Opinion issued for PCT/US2010/059925, dated May 9, 2011, 9 pages.
Coutts, R.T., et al., "Involvement of CYP2D6, CYP3A4, and other cytochrome P-450 isozymes in N-dealkylation reactions," J Pharmacol Toxicol Methods, 1994, 31(4): pp. 177-186.

(56) References Cited

OTHER PUBLICATIONS

Cullen, W.K., et al., "Block of LTP in rat hippocampus in vivo by β-amyloid precursor protein fragments," Neuroreport, 1997, 8(15): pp. 3213-3217.
Czech, C., et al., "Presenilins and alzheimer's disease: biological functions and pathogenic mechanisms," Prog Neurobiol, 2000, 60:pp. 363-384.
Dahiyat, B.I., et al., "De novo protein design: fully automated sequence selection," Science, 1997, vol. 278, pp. 82-87.
Dal Paz, F., et al., "The identification of a novel natural activator of p300 histone acetyltransferase provides new insights into the modulation mechanism of this enzyme," Chembiochem, 2009, 11(6): pp. 818-827.
Dallas, A., et al., "RNAi: a novel antisense technology and its therapeutic potential," Med Sci Monit, 2006, 12(4): pp. RA67-RA74.
Dash, P.K., et al., "Injection of the cAMP-responsive element into the nucleus of Aplysia sensory neurons blocks long-term facilitation," Nature, 1990, 345(6277): pp. 718-721.
De La Cruz, X. et al., "Do protein motifs read the histone code?," Bioessays, vol. 27, No. 2, pp. 164-175 (Feb. 2005).
De Ruijter, A.J.M., et al., "Histone deacetylases (HDACs): characterizaiton of the classical HDAC family," Biochem J., 2003, 370(pt 3): pp. 737-749.
Devlin, J.J., et al., "Random peptide libraries: a source of specific protein binding molecules," Science, 1990, vol. 249, pp. 404-406.
Di Rosa, G. et al., "Calpain inhibitors: a Treatment for Alzheimer's Disease" Journal of Molecular Neuroscience, vol. 19, pp. 135-141 (2002).
Dineley, K.T., et al., "Accelerated plaque accumulation, associative learning deficits, and up-regulation of α7 nicotinic receptor protein in transgenic mice co-expressing mutant human presenilin 1 and amyloid precursor proteins," J Biol Chem, 2002, 277(25): pp. 22768-22780.
Dineley, K.T., et al., "β-Amyloid Activates the Mitogen-Activated Protein Kinase Cascade via Hippocampal α7 Nicotinic Acetylcholine Receptors: In Vitro and In Vivo Mechanisms Related to Alzheimer's Disease," Journal of Neuroscience, vol. 21, No. 12, pp. 4125-4133 (Jun. 15, 2001).
Duff, K., et al., "Increased amyloid-β42(43) in brains of mice expressing mutant presenilin 1," Nature, vol. 383, pp. 710-713 (Oct. 1996).
Elbashir, S.M., et al., "Duplexes of 21-nucleotide RNAs mediate RNA interference in cultured mammalian cells," Nature, vol. 411, pp. 494-498 (May 24, 2001).
Emborg, Marina E., "Evaluation of animal models of Parkinson's disease for neuroprotective strategies," Journal of Neuroscience Methods, vol. 139, pp. 121-143 (Oct. 2004).
Erb, E., et al., "Recursive deconvolution of combinatorial chemical libraries," Proc Natl Acad Sci USA, 1994, vol. 91, pp. 11422-11426.
Eyupoglu, I.Y., et al., "Experimental therapy of malignant gliomas using the inhibitor of histone deacetylase MS-275," Mol Cancer Ther, 2006, 5(5): pp. 1248-1255.
Fischer, A., et al., "Recovery of learning and memory is associated with chromatin remodelling," Nature, vol. 447, pp. 178-182 (May 2007).
Fitzjohn, S.M., et al., "Age-related impairment of synaptic transmission but normal long-term potentiation in transgenic mice that overexpress the human APP695SWE mutant form of amyloid precursor protein," J Neurosci, 2001, 21(13): ppl. 4691-4698.
Fleming, S.M., et al., "Early and progressive sensorimotor anaomalies in mice overexpressing wild-type human α-synuclein," The J of Neuroscience, 2004, vol. 24, No. 42, pp. 9434-9440.
Fodor, S.P.A., et al., "Light-directed, spatially addressable parallel chemical synthesis," Science, 1991, vol. 251, pp. 767-773.
Francis, Y.I., et al., "CREB-binding protein activation by presenilin 1 but not by its M146L mutant," Neuroreport, 2006, 17: pp. 917-921.
Francis, Y.I., et al., "Dysregulation of histone acetylation in the APP/PS1 mouse model of alzheimer's disease," J Alzheimers Dis, 2009, 18(1): pp. 131-139.
Francis, Y.I., et al., "p300 activation by Presenilin 1 but not by its M146L mutant," Neuroscience Letters, vol. 413, pp. 137-140 (Feb. 2007).
Freir, D.B., et al., "Blockade of long-term potentiation by β-amyloid peptides in the CA1 region of the rat hippocampus in vivo," J Neurophysiol, 2001, 85(2): pp. 708-713.
Gallop, M.A., et al., "Applications of combinatorial technologies to drug discovery. 1. backgroud and peptide combinatorial libraries," J Medicinal Chemistry, 1994, vol. 37, No. 9, pp. 1233-1251.
Garcia, B.A., et al., "Chemical derivatization of histones for facilitated analysis by mass spectrometry," Nat Protoc, 2007, 2(4): pp. 933-938.
Gong, B. et al., "Ubiquitin Hydrolase Uch-L1 Rescues β-Amyloid-Induced Decreases in Synaptic Function and Contextual Memory" Cell, vol. 126, No. 4, pp. 775-788 (Aug. 2006).
Gong, B., et al., "Persistent improvement in synaptic and cognitive functions in an alzheimer mouse model after rolipram treatment," J. Clin Invest, 2004, 114: pp. 1624-1634.
Green, K.N., et al., "Nicotinamide restores cognition in alzheimer's disease transgenic mice via a mechanism involving sirtuin inhibition and selective reduction of Thr231-phosphotau," J Neurosci, 2008, vol. 28, pp. 11500-11510.
Gregoretti, I.V., et al., "Molecular evolution of the histone deacetylase family: functional implications of phylogenetic analysis," J Mol Biol, 2004, 338(1): pp. 17-31.
Guan, J.S., et al., "HDAC2 negatively regulates memory formation and synaptic plasticity," Nature, 2009, 459(7243): pp. 55-60.
Guo, X., et al. "Epigenetic mechanisms of amyloid-β production in anisomycin-treated SH-SY5Y cells," Neuroscience, vol. 194, pp. 272-281 (Oct. 2011).
Gwack, Y., et al., "CREB-Binding Protein and Histone Deacetylase Regulate the Transcriptional Activity of Kaposi's Sarcoma-Associated Herpesvirus Open Reading Frame 50," Journal of Virology, vol. 75, No. 4, pp. 1909-1917 (Feb. 2001).
Haas, J., et al., "Inducible nitric oxide synthase and argininosuccinate synthetase: co-induction in brain tissue of patients with Alzheimer's dementia and following stimulation with β-amyloid 1-42 in vitro," Neuroscience Letters, vol. 322, pp. 121-125 (Apr. 2002).
Hansen, J.B., "Towards selective Kir6.2/SUR1 potassium channel openers, medicinal chemistry and therapeutic perspectives," Curr Med Chem, 2006, vol. 13, No. 4, pp. 361-376.
Hockly, E., et al., "Suberoylanilide hydroxamic acid, a histone deacetylase inhibitor, ameliorates motor deficits in a mouse model of Huntington's disease," Proc. National Academy of Sciences USA, vol. 100, No. 4, pp. 2041-2046 (Feb. 2003).
Hodgson, J.G., et al., "A YAC Mouse Model for Huntington's disease with Ffull-Length Mutant Huntingtin, Cytoplasmic Toxicity, and Selective Striatal Neurodegeneration," Neuron, vol. 23, pp. 181-192 (May 1999).
Hodgson, J.G., et al., "ADMET—turning chemicals into drugs: Rapidly resolving the pharmacokinetic and tocxicological properties of drug candidates remains a key challenge for drug developers," Nature Biotechnology, vol. 19, No. 8, pp. 722-726 (Aug. 2001).
Holcomb, L., et al., "Accelerated alzheimer-type phenotype in transgenic mice carrying both mutant amyloid precursor protein and presenilin 1 transgenes," Nat Med, 1998, 4: pp. 97-100.
Houghten, R.A., et al., "Generation and use of synthetic peptide combinatorial libraries for basic research and drug discovery," Nature, 1991, vol. 354, pp. 84-86.
Houghten, R.A., et al., "The use of synthetic peptide combinatorial libraries for the identification of bioactive peptides," Biotechniques, 1992, vol. 13, pp. 412-421.
Hsia, A. Y., et al., "Plaque-independent disruption of neural circuits in alzheimer's disease mouse models," Proc Natl Acad Sci USA, 1999, 96(6): pp. 3228-3233.
Hsiao, K., et al., "Correlative Memory Deficits, Aβ Elevation, and Amyloid Plaques in Transgenic Mice," Science, vol. 274, pp. 99-102 (Oct. 1996).

(56) References Cited

OTHER PUBLICATIONS

Hudson, P.J., "Recombinant antibody fragments," Curr Opin Biotechnol, 1998, vol. 9, pp. 395-402.

Hwang, D. Y., et al., "3,4-Dihydroxyphenylalanine reverses the motor deficits in Pitx3-deficient aphakia mice: behavioral characterization of a novel genetic model of parkinson's disease," The J of Neuroscience, 2005, vol. 25, No. 8, pp. 2132-2137.

Itoh, A., et al., "Impairments of long-term potentiation in hippocampal slices of β-amyloid-infused rates," European Journal of Pharmacology, vol. 382, pp. 167-175 (Oct. 1999).

Janeway, C., et al., "Immunobiology: the immune system in health and disease," Garland Publishing, 2001, New York, 5th Edition, 13 pg.

Jayawickreme, C.K., et al., "Creation and functional screening of a multi-use peptide library," Proc Natl Acad Sci USA, 1994, vol. 91, pp. 1614-1618.

Jolas, T., et al., "Long-Term Potentiation Is Increased in the CA1 Area of the Hippocampus of APP swe/ind CRND8 Mice," Neurobiology of Disease, vol. 11, No. 3, pp. 394-409 (Dec. 2002).

Kalota, A., et al., "Progress in the Development of Nucleic Acid Therapeutics," Handbook Exp. Pharmacol, 2006, vol. 173, pp. 173-196.

Kamal, A., et al., "Kinesin-mediated axonal transport of a membrane compartment containing β-secretase and presenilin-1 requires APP," Nature, 2001, vol. 414, pp. 643-648.

Kandel, E.R., "The molecular biology of memory storage: a dialog between genes and synapses," Biosci Rep, 2001, 21(5): pp. 565-611.

Kang, J., et al., "The precursor of Alzheimer's disease amyloid A4 protein resembles a cell-surface receptor," Nature, vol. 325, pp. 733-736 (1987).

Kay, B.K., et al., "An M13 phage library displaying random 38-amino-acid peptides as a source of novel sequences with affinity to selected targets," Gene, 1993, vol. 128, pp. 59-65.

Kazantsev, A.G., et al., "Therapeutic application of histone deacetylase inhibitors for central nervous system disorders," Nat Rev Drug Discov, 2008, vol. 7, pp. 854-868.

Kemenes, I., et al., "Critical time-window for NO-cGMP-dependent long-term memory formation after one-trial appetitive conditioning," J Neurosci, 2002, 22(4), pp. 1414-1425.

Kim, D., et al., "SIRT1 deacetylase protects against neurodegeneration in models for Alzheimer's disease and amyotrophic lateral sclerosis," The EMBO Journal, vol. 26, pp. 3169-3179 (Jul. 2007).

Kim, J.H., et al., "Use-dependent effects of amyloidogenic fragments of β-amyloid precursor protein on synaptic plasticity in rat hippocampus in vivo," J. Neurosci, 2001, 21(4): pp. 1327-1333.

Kimura, A., et al. "A Decade of Histone Acetylation: Marking Eukaryotic Chromosomes with Specific Codes," Journal of Biochemistry, vol. 138, No. 6, pp. 647-662 (Dec. 2005).

Kornberg, R.D., et al., "Twenty-FIve years of the nucleosome, fundamental particle of the eukaryote chromosome," Cell, 1999, 98(3): pp. 285-294.

Korzus, E., et al., "CBP Histone Acetyltransferase Activity Is a Critical Component of Memory Consolidation," Neuron, vol. 42, No. 6, pp. 961-972 (Jun. 24, 2004).

Kowalska, M.A., et al., "Beta-amyloid protein induces platelet aggregation and supports platelet adhesion," Biochem Biophys Res Commun, 1994, 205(3): pp. 1829-1835.

Kuehne, M. E., et al., "Reduction of amides and lactams to amines by reactions with phosphorus oxychloride and sodium borohydride," J Org Chem, 1977, 42: pp. 2082-2087.

Kurt, M.A., et al., "Neurodegenerative changes associated with β-amyloid deposition in the brains of mice carrying mutant amyloid precursor protein and mutant presenilin-1 transgenes," Exp Neurol, 2001, 171(1): pp. 59-71.

Lam, K.S., et al., "A new type of synthetic peptide library for identifying ligand-binding activity," Nature, 1991, vol. 354, pp. 82-84.

Lambert, M.P., et al., "Diffusivle, nonfibrillar ligands derived from $Aβ_{1-42}$ are potent central nervous system neurotoxins," Proc Natl Acad Sci USA, 1998, 95: pp. 6448-6453.

Lander, E.S., et al., "Initial sequencing and analysis of the human genome," Nature, 2001, 409(6822), p. 860-921.

Lane, A.A., et al., "Histone deacetylase inhibitors in cancer therapy," J Clin Oncol, 2009, 27)32), pp. 5459-5468.

Lane, E., et al., "Animal models of Parkinson's disease and L-dopa induced dyskinesia: how close are we to the clinic?," Psychopharmacology, vol. 199, pp. 303-312 (Aug. 2008).

Langley, B., et al., "Remodeling Chromatin and Stress Resistance in the Central Nervous System: Histone Deacetylase Inhibitors as Novel and Broadly Effective Neuroprotective Agents," Current Drug Targets: CNS & Neurological Disorders, vol. 4, No. 1, pp. 41-50 (Feb. 2005).

Larson, J., et al., "Alterations in synaptic transmission and long-term potentiation in hippocampal slices from young and aged PDAPP mice," Brain Research, vol. 840, No. 1, pp. 23-35 (Sep. 1999).

Lee, K.K., et al., Histone acetyltransferase complexes: one size doesn't fit all, Nat Rev Mol Cell Biol, 2007, vol. 8, No. 4, pp. 284-295.

Lenstra, J.A., et al., "Isolation of sequences from a random-sequence expression library that mimic viral epitopes," J Immunol Meth, 1992, vol. 152, pp. 149-157.

Levenson, J.M., et al., "Epigenetic mechanism in memory formation," Nature Reviews, vol. 6, No. 2, pp. 108-118 (Feb. 2005).

Levenson, J.M., et al., "Regulation of histone acetylation during memory formation in the hippocampus," J Biol Chem, 2004, vol. 279, pp. 40545-40559.

Levy-Lahad, E., et al., "A Familial Alzheimer's Disease Locus on Chromosome 1," Science, vol. 269, pp. 970-973 (Aug. 1995).

Lodish, H., et al., "Molecular Cell Biology," 4 ed, 2000, New York: W.H. Freeman Company, 24 pg.

Lu, F., et al., "Chromatin Remodeling of the Kaposi's Sarcoma-Associated Herpesvirus ORF50 Promoter Correlates with Reactivation from Latency" Journal of Virology, vol. 77, No. 21, pp. 11425-11435 (Nov. 2003).

Lu, Y.F., et al., "Nitric oxide signaling contributes to late-phase LTP and CREB phosphorylation in the hippocampus," J Neurosci, 1999, 19(23): pp. 10250-10261.

Lutzelberger, M., et al., "Strategies to identify potential therapeutic target sites in RNA," Handbook Exp Pharmacol, 2006, vol. 173, pp. 243-259.

Mahmoud, R.M., et al., "Synthesis of novel indeno[1,2-c]isoquinoline derivatives," Synthetic Communications, 2010, 40: pp. 666-676.

Malm, T., et al., "β-Amyloid infusion results in delayed and age-dependent learning deficits without role of inflammation or β-amyloid deposits," Proc Natl Acad Sci USA, 2006, 103: pp. 8852-8857.

Manh, H.T., et al., "Amyloid β-peptide induces nitric oxide production in rat hippocampus: association with cholinergic dysfunction and amelioration by inducible nitric oxide synthase inhibitors," Faseb J., 2001, 15(8): pp. 1407-1409.

Mannhold,R., "Structure-activity relationships of $K_{ATP}$ channel openers," Curr Top Med Chem, 2006, vol. 6, No. 10, pp. 1031-1047.

Mantelingu, K., et al., "Activation of p300 Histone Acetyltransferase by Small Molecules Altering Enzyme Structure: Probed by Surface-Enhanced Raman Spectroscopy," Journal of Physical Chemistry B, vol. 111, pp. 4527-4534 (May 2007).

Mao, X., et al., "GCN5 is a required cofactor for a ubiquitin ligase that targets NF-κB/RelA," Genes Dev, 2009, vol. 23, No. 7, pp. 849-861.

Marmonstein, R., et al., "Histone acetyltransferases: function, structure, and catalysis," Curr Opin in Genet and Develop, 2001, vol. 11, pp. 155-161.

Marmorstein, R., "Structure of histone acetyltranserases," J Molec Biol, 2001, 311: pp. 433-444.

Masliah, E., "Mechanisms of synaptic dysfunction in Alzheimer's disease," Histology and Histopathology, vol. 10, pp. 509-519 (Apr. 1995).

(56) References Cited

OTHER PUBLICATIONS

Mattheakis, L.C., et al., "An in vitro polysome display system for identifying ligands from very large peptide libraries," Proc Natl Acad Sci USA, 1994, vol. 91, pp. 9022-9026.
Mattson, M.P., et al., "Secreted form of amyloid precursor protein enhances basal glucose and glutamate transport and protects against oxidative impairment of glucose and glutamate transport in synaptosomes by a cyclic GMP-mediated mechanism," J Neurochem, 1999, 73(2), pp. 532-537.
Maurice, T., et al., "Altered memory capacities and response to stress in p300/CBP-associated factor (PCAF) histone acetylase knockout mice," Neuropsychopharmacology, 2008, 33(7): pp. 1584-1602.
Maynard, J., et al., "Antibody Engineering," Ann Rev Biomed Eng, 2008, vol. 2, pp. 339-376.
McCann, S.M., "The nitric oxide hypothesis of brain aging," Exp Gerontol, 1997, 32(4-5), pp. 431-440.
McCarty, M.F., "Vascular nitric oxide may lessen alzheimer's risk," Med Hypotheses, 1998, 51(6): pp. 465-476.
McConnell, H.M., et al., "The Cytosensor Microphysiometer: Biological Applications of Silicon Technology," Science, vol. 257, pp. 1906-1912 (Sep. 25, 1992).
McGowan, E., et al., "Amyloid phenotype characterization of transgenic mice overexpressing both mutant amyloid precursor protein and mutant presenilin 1 transgenes," Neurobiol Dis, 1999, 6(4): pp. 231-244.
Medynski, D., "Synthetic peptide combinatorial libraries," Biotechnology, 1994, vol. 12, pp. 709-710.
Melgar-Fernandez, R., et al., "Synthesis of novel derivatives of (1S,4S)-2,5-diazabicyclo[2.2.1]heptane and their evaluation as potential ligands in asymmetric catalysis," Eur. J. Org. Chem., 2008: p. 655-672.
Meredith, G.E., et al., "Animal Models of Parkinson's Disease Progression" Acta Neuropathology, vol. 115, No. 4, 21 pages (Apr. 2008).
Moechars, D, et al, "Early phenotypic changes in transgenic mice that overexpress different mutants of amyloid precursor protein in brain," J Biol Chem, 1999, 274(10): pp. 6483-6492.
Mondal, M., et al., "Facile Synthesis of 1,3,7-Trihydroxyxanthone and Its Regioselective Coupling Reactions with Prenal: Simple and Efficient Access to Osajaxanthone and Nigrolineaxanthone F," The Journal Organic Chemistry, vol. 71, No. 13, pp. 4992-4995 (Jun. 2006).
Monsonego, A., et al., "Microglia-Mediated Nitric Oxide Cytotoxicity of T Cells Following Amyloid β-Peptide Presentation to Th1 Cells," Journal of Immunology, vol. 171, No. 5, pp. 2216-2224 (Sep. 2003).
Montarolo, P.G., et al., "A critical period for macromolecular synthesis in long-term heterosynaptic faciliation in Aplysia," Science, 1986, 234(4781): pp. 1249-1254.
Mosbach, K., "Molecular Imprinting," Trends in Biochem Sci, 1994, vol. 19, No. 9, pp. 9-14.
Nakagami, Y., et al., "A novel β-sheet breaker, RS-0406, reverses amyloid β-induced cytotoxicity and impairment of long-term potentiation in vitro," British Journal of Pharmacology, vol. 137, pp. 676-682 (Nov. 2002).
Nalbantoglu, J., et al., "Impaired learning and LTP in mice expressing the carboxy terminus of the Alzheimer amyloid precursor protein," Nature, vol. 387, pp. 500-505 (May 29, 1997).
Narayanan, B.C., et al., "Structure and Function of PA4872 from Pseudomonas aeruginosa, A Novel Class of Oxaloacetate Decarboxylase from the PEP Mutase/Isocitrate Lyase Superfamily," Biochemistry, vol. 47, pp. 167-182 (2008).
Ng, H.H., et al., "Histone deacetylases: silencers for hire," Trends in Biochem Sci, 2000, 25(3): pp. 121-126.
Ninan, I., et al., "Presynaptic CaMKII Is Necessary for Synaptic Plasticity in Cultured Hippocampal Neurons," Neuron, vol. 42, pp. 129-141 (Apr. 8, 2004).

Ohlmeyer, M.H., et al., "Complex synthetic chemical libraries indexed with molecular tags," Proc Natl Acad Sci USA, 1993, vol. 90, pp. 10922-10926.
Ostresh, J.M., et al., "'Libraries from libraries': chemical transformation of combinatorial libraries to extend the range and repertoire of chemical diversity," Proc Natl Acad Sci USA, 1994, vol. 91, pp. 11138-11142.
Paakkari, I., et al., "Nitric oxide in the central nervous system," Ann Med, 1995, 27(3): pp. 369-377.
Parkinson's Disease mice models available from the Jackson Laboratory, Bar Harbor, ME at http://jaxmice.jax.org/list/ra1594.html; 17 pgs. (Retrieved from the internet on Jun. 26, 2014).
Paxinos, G., et al., "The mouse brain in stereotaxic coordinates," 2nd ed, 1998, (2001), New York: Academic Press, 4 pg.
Peleg, S., et al., "Altered histone acetylation is associated with age-dependent memory impairment in mice," Science, 2010, 328(5979): pp. 753-756.
Peterson, C.L., et al., "Histones and histone modifications," Curr Biol, 2004, 14(14): pp. R546-R551.
Phillips, R.G., et al., Differential Contribution of Amygdala and Hippocampus to Cued and Contextual Fear Conditioning,: Behav Neurosci, 1992, 106(2): pp. 274-285.
Pittenger, C., et al., "In search of general mechanisms for long-lasting plasticity: Aplysia and the hippocampus," Phil. Trans. R. Soc. Lond. B, vol. 358, pp. 757-763 (Apr. 2003).
Prickaerts, J., et al., "cGMP but not cAMP, in rat hippocampus is involved in early stages of object memory consolidation," Eur J Pharmacol, 2003, 436(1-2): pp. 83-87.
Puzzo, D., et al., "Amyloid-β peptide inhibits activation of the nitric oxide/cGMP/cAMP-responsive element-binding protein pathway during hippocampal synaptic plasticity," J Neurosci, 2005, 25(29): pp. 6887-6897.
Puzzo, D., et al., "Picomolar amyloid-β positively modulates synaptic plasticity and memory in hippocampus," J. Neurosci, 2008, 28(53): pp. 14537-14545.
Puzzo, D., et al., "Sildenafil resuces synaptic and cognitive impairment in a mouse model of alzheimer's disease," Soc Neurosci Abstr, 2005, Atlanta, 1 pg.
Rajan, I., et al., "Loss of the putative catalytic domain of HDAC4 leads to reduced thermal nociception and seizures while allowing normal bone development," PLoS One, 2009, 4(8):e6612, 11pgs.
Rakyan, V.K., et al., "The marks, mechanism and memory of epigenetic states in mammals," Biochem J, 2001, 356: pp. 1-10.
Roelfsema, J.H., et al., "Rubinstein-Taybi syndrome: clinical and molecular overview," Expert Rev Mol Med, 2007, 9(23): pp. 1-16.
Rouaux, C., et al., "Critical loss of CBP/p300 histone acetylase activity by caspase-6 during neurodegeneration," The EMBO Journal, vol. 22, No. 24, pp. 6537-6549 (Dec. 2003).
Salmon, S.E., et al., "Discovery of biologically active peptides in random libraries: solution-phase testing after staged orthogonal release from resin beads," Proc Natl Acad Sci USA, 1993, vol. 90, pp. 11708-11712.
Sant'Angelo, A., et al., "Usefulness of behavioral and electrophysiological studies in transgenic modesl fo alzheimer's disease," Neurochem Res, 2003, 28(7): pp. 1009-1015.
Saura, C.A., et al., "Loss of presenilin function causes impairments of memory and synaptic plasticity followed by age-dependent neurodegeneration," Neuron, 2004, 42: pp. 23-36.
Sbardella, G., et al., "Identification of long chain alkylidenemalonates as novel small molecule modulators of histone acetyltransferases," Bioorg Med Cham Lett, 2008, 18(9): pp. 2788-2792.
Schenk, D., et al., "Immunization with amyloid-β attenuates Alzheimer-disease-like pathology in the PDAPP mouse," Nature, vol. 400, pp. 173-177 (Jul. 8, 1999).
Schultheiss, D. et al., "Central effects of sildenafil (Viagra) on auditory selective attention and verbal recognition memory in humans: a study with event-related brain potentials," World J Urol, 2001, 19(1): pp. 46-50.
Scott, J. K., et al., "Searching for peptide ligans with an epitope library," Science, 1990, vol. 249, pp. 386-390.

(56) References Cited

OTHER PUBLICATIONS

Selig, D.K., et al., "Examination of the role of cGMP in long-term potentiation in the CA1 region of the hippocampus," Learn Mem, 1996, 3(1): pp. 42-48.
Selkoe, D.J., "Alzeihmer's disease is a synaptic failure," Science, 2002, 298(5594): pp. 789-791.
Shea, K.J., "Molecular imprinting of synthetic network polymers: the de novo synthesis of macromolecular binding and catalytic sites," Trip, 1994, vol. 2, No. 5, pp. 166-173.
Sherrington, R., et al., "Cloning of a gene bearing missense mutations in early-onset familial Alzheimer's disease," Nature, vol. 375, pp. 754-760 (Jun. 29, 1995).
Simon, R.J., et al., "Peptoids: a modular approach to drug discovery," Proc Natl Acad Sci USA, 1992, vol. 89, pp. 9367-9371.
Sipos, E., et al., "β-amyloid pathology in the entorhinal cortex of rats induces memory deficits: implications for Alzheimer's disease," Neuroscience, vol. 147, pp. 28-36 (Jun. 2007).
Sjolander, S., et al., "Integrated Fluid Handling System for Biomolecular Interaction Analysis," Anal. Chem., vol. 63, pp. 2338-2345 (1991).
Sperling, R.A., et al., "fMRI studies of associative encoding in young and elderly controls and mild alzheimer's disease," J Neurol Neurosurg Psychiatry, 2003, 74(1): pp. 44-50.
Stephan, A., et al., "Generation of Aggregated β-Amyloid in the Rat Hippocampus Impairs Synaptic Transmission and Plasticity and Causes Memory Deficits," Journal of Neuroscience, vol. 21, No. 15, pp. 5703-5714 (Aug. 2001).
Stine, W. B., et al., "In vitro characterization of conditions for amyloid-β peptide oligomerization and fibrillogeneis," J Biol Chem, 2003, vol. 278, pp. 11612-11622.
Strahl, B.D., et al., "THe language of covalent histone modifications,:" Nature, 2000, 403(6765): pp. 41-45.
Suhara, T., et al., "Aβ42 generation is toxic to endothelial cells and inhibits eNOS function through an Akt/GSK-3β signaling-dependent mechanism," Neurobiol Agin, 2003, 24(3): pp. 437-451.
Sweatt, J.D., "Epigenetics and Cognitive Aging," Science, vol. 328, pp. 701-702 (May 2010).
Takahashi, H., et al., "Impaired proteolytic processing of Presenilin-1 in chromosome 14-linked familial Alzheimer's disease patient lymphocytes," Neurosciece Letters, vol. 260, pp. 121-124 (Jan. 1999).
Tanzi, Rudolph E., "The synaptic Aβ hypothesis of Alzheimer disease," Nature Neuroscience, vol. 8, No. 8, pp. 977-979 (Aug. 2005).
Thatcher, G.R.J., et al., "Nitric oxide mimetic molecules as therapeutic agents in alzheimer's disease," Curr Alzheimer Res, 2005, 2(2): pp. 171-182.
Thompson, T.N., "Optimization of metabolic stability as a goal of modern drug design," Med Res Rev, 2001, 21(5): pp. 412-449.
Tran, M.H., et al., "Amyloid β-peptide induces nitric oxide production in rat hippocampus: association with cholinergic dysfunction and amelioration by inducible nitric oxide synthase inhibitors," The FASEB Journal, vol. 15, No. 8, pp. 20 pgs. (Jun. 2001).
Trinchese, F., et al., "Progressive Age-Related Development of Alzheimer-like Pathology in APP/PS1 Mice," American Neurolocial Association, vol. 55, No. 6, pp. 801-814 (Jun. 2004).
Troy, C.M., et al., "Caspase-2 Mediates Neuronal Cell Death Induced by β-Amyloid," Journal of Neuroscience, vol. 20, No. 4, pp. 1386-1392 (Feb. 2000).
Tsuritani, T., et al., "Efficient synthesis of 1,4-diaryl-5-methyl-1,2,3-triazole, a potential mGluR1 antagonist, and the risk assessment study of arylazides," Organic Process Research & Development, 2009, 13(6): pp. 1407-1412.
Van Staveren, W.C.G., et al., "mRNA expression patterns of the cGMP-hydrolyzing phosphodiesterases types 2, 5, and 9 during development of the rat brain," J Comp Neurol, 2003, 467(4): pp. 566-580.
Van Staveren, W.C.G., et al., "Species differences in the localization of cGMP-producing and NO-responsive elements in the mouse and rat hippocampus using cGMP immunocytochemistry," Eur J Neurosci, 2004, 19(8): pp. 2155-2168.
Vecsey, C.G., et al., "Histone deacetylase inhibitors enhance memory and synaptic plasticity via CREB: CBP-dependent transcriptional activation," J Neurosci, 2007, 27(23): pp. 6128-6140.
Venturini, G., et al., "β-Amyloid inhibits NOS activity by subtracting NADPH availability," Faseb J, 2002, 16(14): pp. 1970-1972.
Vitolo, O.V., et al., "Amyloid β-peptide inhibition of the PKA/CREB pathway and long-term potentiation: reversibility by drugs that enhance cAMP signaling," Proc Natl Acad Sci USA, 2002, 99(20): pp. 13217-13221.
Walsh, D., et al. "Certain Inhibitors of Synthetic Amyloid β-Peptide (Aβ) Fibrillogenesis Block Oligomerization of Natural Aβ and Thereby Rescue Long-Term Potentiation," The Journal of Neuroscience, vol. 25, No. 10, pp. 2455-2462 (Mar. 2005).
Walsh, D.M., et al., "Naturally secreted oligomers of amyloid β protein potently inhibit hippocampal long-term potentiation in vivo," Nature, 2002, 416(6880): pp. 535-539.
Wang, H., et al., "ATP-Sensitive potassium channel openers and 2,3-dimethyl-2-butylamine derivatives," Curr Med Chem, 2007, vol. 14, No. 2, pp. 133-155.
Wang, Q., et al., "β-Amyloid-mediated inhibition of NMDA receptor-dependent long-term potentiation induction involves activation of microglia and stimulation of inducible nitric oxide synthase and superoxide," J Neurosci, 2004, 24(27): pp. 6049-6056.
Werner, T., et al., "Joining high-throughput technology with in silico modelling advances genome-wide screening towards targeted discovery," Brief Funct. Genomic Proteomic, 2006, vol. 5, No. 1, pp. 32-36.
Wirtz-Brugger, F., et al., "Guanosine 3',5'-cyclic monophosphate mediated inhibition of cell death induced by nerve growth factor withdrawal and β-amyloid: protective effects of propentofylline," Neuroscience, 2000, 99(4): pp. 737-750.
Wong, A., et al., "Advanced glycation endproducts co-localize with inducible nitric oxide synthase in Alzheimer's disease," Brain Research, vol. 920, pp. 32-40 (Nov. 2001).
Wu, J., et al., "β-Amyloid-(1-40) increases long-term potentiation in rat hippocampus in vitro," European Journal of Pharmacology, vol. 284, pp. R1-R3 (Sep. 1995).
Wuff, G., "Molecular recognition in polymers prepared by imprinting with templates," Ford, ACS Symposium Series No. 308, American Chemical Society 1986, pp. 186-230.
Xie, Z., et al., "Peroxynitrite Mediates Neurotoxicity of Amyloid β-Peptide $_{1-42}$- and Lipopolysaccharide-Activated Microglia," The Journal of Neuroscience, vol. 22, No. 9, pp. 3484-3492 (May 2002).
Yang, X-J., et al., "HATs and HDACs: from structure, function and regulation to novel strategies for therapy and prevention," Oncogene, 2007, 26(37): pp. 5310-5318.
Yin, J.C.P., et al., "Induction of a dominant negative CREB transgene specifically blocks long-term memory in *Drosophila*," Cell, 1994, 79(1): pp. 49-58.
Clements, A. et al., "Crystal structure of the histone acetyltransferase domain of the human PCAF transcriptional regulator bound to coenzyme A," The EMBO Journal, vol. 18, No. 13, pp. 3521-3532 (1999).
Corless, I.B. et al., "Predictors of Perception of Cognitive Functioning in HIV/AIDS," Journal of the Association of Nurses in AIDS care, vol. 11, Issue 3, pp. 19-26 (May-Jun. 2000).
European Search Report issued by the European Patent Office for Application No. 11850544.5 dated Jul. 29, 2014 (8 pages).
International Search Report and Written Opinion issued by the International Search Authority for Application No. PCT/US12/41907, dated Sep. 21, 2012 (9 pages).
Renaud, J. et al., "Estrogen Receptor Modulators: Identification and Structure-Activity Relationships of Potent ERα-Selective Tetrahydroisoquinoline Ligands," Journal of Medicinal Chemistry, American Chemical Society, vol. 46, pp. 2945-2957 (Jan. 1, 2003).
Clements, A. et al., "Crystal structure of the histone acetyltransferase domain of the human PCAF transcriptional regulator bound to coenzyme A." The EMBO Journal 18(13):3521-3532, 1999.

\* cited by examiner

HISTONE ACETYLTRANSFERASE MODULATORS AND USES THEREOF

This application claims priority to International Application No. PCT/US2011/066851, filed on Dec. 22, 2011, which claims priority to U.S. Provisional Application No. 61/426,033, filed on Dec. 22, 2010, U.S. Provisional Application No. 61/539,697, filed on Sep. 27, 2011, and U.S. Provisional Application No. 61/541,706, filed on Sep. 30, 2011, each of which are incorporated herein by reference in their entireties.

GOVERNMENT SUPPORT

This invention was made with government support under grants NS049442, AG017490, AG014351, and AG031294 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Cognitive neurodegenerative disorders are characterized by synaptic dysfunction, cognitive abnormalities, and/or the presence of inclusion bodies throughout the CNS containing, for example, but not limited to native beta-amyloid fragments, native and phosphorylated Tau, native and phosphorylated alpha-synuclein, lipofuscin, cleaved TARDBP (TDB-43), in various percentages and in relation to the specific disease.

Alzheimer's disease (AD) is a neurodegenerative disorder characterized by memory loss, synaptic dysfunction and accumulation of amyloid β-peptides (Aβ). It is caused in part by increased levels of amyloid-β-peptide 1-42 (Aβ42). Although Alzheimer's Disease (AD) was described almost a century ago, the molecular mechanisms that lead to its development are still unknown. From a neuropathological point of view, Alzheimer's Disease is characterized by the presence of amyloid plaques and neurofibrillary tangles associated with neuronal degeneration; whereas the clinical hallmark is progressive memory loss associated with a number of neuropsychiatric symptoms.

Currently available therapies for AD are palliative and do not address the underlying cause of the disease. Cholinesterase inhibitors such as Razadyne® (galantamine), Exelon® (rivastigmine), Aricept® (donepezil), and Cognex® (tacrine) have been prescribed for early stages of Alzheimer's disease, and may temporarily delay or prevent progression of symptoms related to AD. However, as AD progresses, the brain loses less acetylcholine, thereby rendering cholinesterase inhibitors unproductive as treatment for AD. Namenda® (memantine), an N-methyl D-aspartate (NMDA) antagonist, is also prescribed to treat moderate to severe Alzheimer's disease; however only temporary benefits are realized.

Histone Acetyltransferases (HATs) are involved in histone acetylation (leading to gene activation), chromosome decondensation, DNA repair and non-histone substrate modification.

SUMMARY OF THE INVENTION

In one aspect, the invention is directed to a compound of formula (I),

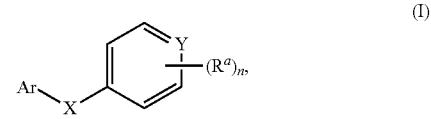

wherein,
Ar is

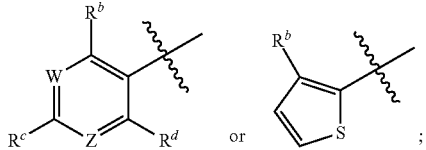

$R^a$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$;
$R^b$ is H, $C_1$-$C_6$-alkyl, $C_2$-$C_6$-alkenyl, $C_3$-$C_8$-cycloalkyl, $C_2$-$C_6$-heteroalkyl, $C_3$-$C_8$-heterocycloalkyl, aryl, heteroaryl, O—($C_1$-$C_6$-alkyl), O—($C_3$-$C_8$-cycloalkyl), O—($C_2$-$C_6$-alkenyl), O—($C_3$-$C_8$-heterocycloalkyl), N($R^{10}$)—($C_1$-$C_6$-alkyl), N($R^{10}$)—($C_3$-$C_8$-cycloalkyl), S—($C_1$-$C_6$-alkyl), O—($C_2$-$C_6$-alkyl)-N($R^{10}$)$_2$, O—($C_3$-$C_8$-cycloalkyl)-N($R^{10}$)$_2$), N($R^{10}$)—($C_2$-$C_6$-alkyl)-N($R^{10}$)$_2$, —($C_1$-$C_6$-alkyl)-N($R^{10}$)$_2$, —($C_1$-$C_6$-alkyl)-$R^3$, O—($C_1$-$C_6$-alkyl)-$R^3$, O—($C_3$-$C_8$-cycloalkyl)-$R^3$), N($R^{10}$)—($C_1$-$C_6$-alkyl)-$R^3$, O-aryl, or O-heteroaryl;
$R^c$ is H, —($C_1$-$C_6$-alkyl), O—($C_1$-$C_6$-alkyl), C(=O)NH-phenyl, wherein phenyl is substituted with one or more halo or haloalkyl;
$R^d$ is H, OH, —($C_1$-$C_6$-alkyl), O—($C_3$-$C_8$-cycloalkyl), O—($C_3$-$C_8$-heterocycloalkyl), O—($C_2$-$C_6$-alkenyl), O—($C_1$-$C_6$-alkyl), O—($C_2$-$C_6$-alkyl)-N($R^{10}$)$_2$, —($C_1$-$C_6$-alkyl)-$R^3$, O—($C_1$-$C_6$-alkyl)-$R^3$), N($R^{10}$)—($C_1$-$C_6$-alkyl)-$R^3$), —N($R^{10}$)—($C_1$-$C_6$-alkyl), —N($R^{10}$)—($C_2$-$C_6$-alkenyl), —N($R^{10}$)—($C_3$-$C_8$-cycloalkyl), —N($R^{10}$)—($C_3$-$C_8$-heterocycloalkyl), N($R^{10}$)—($C_2$-$C_6$-alkyl)-N($R^{10}$)$_2$, —($C_1$-$C_6$-alkyl)-N($R^{10}$)$_2$, S—($C_2$-$C_6$-alkyl)-N($R^{10}$)$_2$, $OCH_2C(O)$ O-alkyl, O-aryl, N-aryl, O-heteroaryl, or N-heteroaryl;
W and Z are independently N or $CR^1$;
X is —CO—, —CON($R^{10}$)—, —CON($R^{10}$)($CH_2$)$_n$—, —($CH_2$)$_n$—CON($R^{10}$)—, —($CH_2$)$_n$CON($R^{10}$)($CH_2$)$_n$—, —SON($R^{10}$)—, —SON($R^{10}$)($CH_2$)$_n$—, —$SO_2$N($R^{10}$)—, —$SO_2$N($R^{10}$)($CH_2$)$_n$—, —N($R^{10}$)C(=O)N($R^{10}$)—, —N($R^{10}$)CO—, —N($R^{10}$)CO($CH_2$)$_n$—, or —N($R^{10}$)CO ($CH_2$)$_n$—, —($CH_2$)$_n$N($R^{10}$)—, —C=N—; or
Ar and X together form

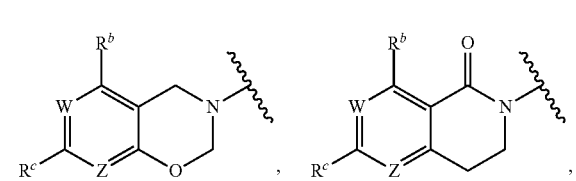

-continued

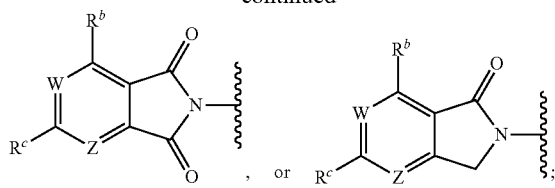

Y is N or CR²;
R¹ is H, halogen, O—(C₁-C₆-alkyl), O—(C₂-C₆-alkyl)N(R¹⁰)₂;
R² is H, C₁-C₆-alkyl, C₁-C₆-haloalkyl, O—(C₁-C₆-alkyl), O—(C₁-C₆-haloalkyl), halogen, CN, or NO₂;
R³ is cycloalkylamino, optionally containing a heteroatom selected from N(R¹⁰), O and S;
R¹⁰ is independently H, —(C₁-C₄-alkyl), —(C₁-C₄-haloalkyl), —(C₃-C₈-cycloalkyl), —(C₃-C₈-heterocycloalkyl), aryl or heteroaryl; and
each n is independently an integer from 1-3, or a pharmaceutically acceptable salt or hydrate thereof; with the proviso that Ar is not

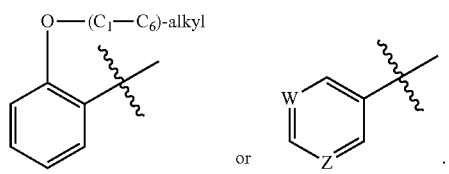

In some embodiments, Rᵃ is H, halogen, or haloalkyl;
Y is CH, C-halogen, or C—CN;
Rᵇ is H, O—(C₁-C₂-alkyl), S—(C₁-C₂-alkyl), O-cyclopentyl, OCH₂CH₂N(CH₃)₂, or CH₂CH₂CH₂N(CH₃)₂;
Rᶜ is H; C(=O)NH-phenyl, wherein phenyl is substituted with one or more halo or haloalkyl;
Rᵈ is H, C₁-C₅-alkyl, OH, O-alkyl, OCH₂CH₂N(CH₃)₂, CH₂CH₂CH₂N(CH₃)₂, SCH₂CH₂N(CH₃)₂, or OCH₂C(=O)O-alkyl;
Z is CH, C—O—(C₁-C₂-alkyl), C—OCH₂CH₂N(CH₃)₂; and
X is CONH, SONH, SO₂NH, NHC(=O)NH, or NHCO, or a pharmaceutically acceptable salt or hydrate thereof.

In some embodiments, when

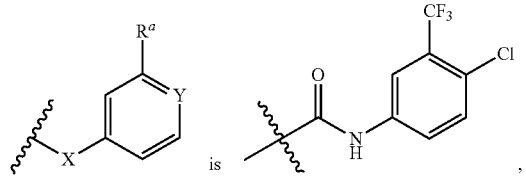

Ar is not

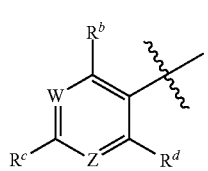

wherein W and Z are each CH, Rᵇ is ethoxy, Rᶜ is hydrogen, and Rᵈ is —OCH₂CH₂N(CH₃)₂ or OH; or
wherein W is C—OCH₂CH₂N(CH₃)₂, Z is CH, Rᵇ is hydrogen, Rᶜ is hydrogen, and Rᵈ is hydrogen; or
wherein W and Z are each CH, Rᵇ is cyclopentyloxy, Rᶜ is hydrogen, and Rᵈ is —OCH₂CH₂N(CH₃)₂; or
wherein W and Z are each CH, Rᵇ is —OCH₂CH₂N(CH₃)₂, Rᶜ is —C(O)NH-(3-CF₃, 4-Cl-phenyl), and Rᵈ is —OCH₂CH₂N(CH₃)₂; or
wherein W is CH, Z is C-ethoxy, Rᵇ is ethoxy, Rᶜ is —C(O)NH-(3-CF₃, 4-Cl-phenyl), and Rᵈ is hydrogen; or
wherein W and Z are each CH, Rᵇ is —CH₂CH₂CH₂N(CH₃)₂, Rᶜ is —C(O)NH-(3-CF₃, 4-Cl-phenyl), and Rᵈ is —CH₂CH₂CH₂N(CH₃)₂ or hydrogen; or
wherein W and Z are each CH, Rᵇ is ethoxy, Rᶜ is —C(O)NH-(3-CF₃, 4-Cl-phenyl), and Rᵈ is hydrogen or —OCH₂CH₂N(CH₃)₂; or
wherein W and Z are nitrogen, Rᵇ is ethoxy, Rᶜ is hydrogen, and Rᵈ is —OCH₂CH₂N(CH₃)₂; or
when

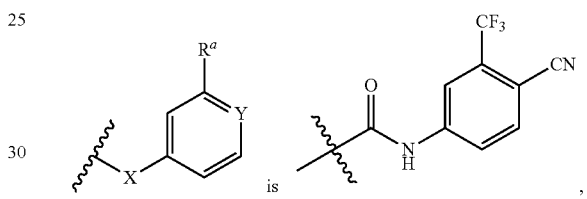

Ar is not

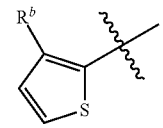

wherein Rᵇ is ethoxy, or Ar is not

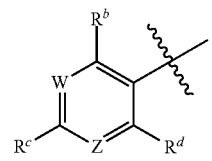

wherein W and Z are each CH, Rᵇ is —S-ethyl, Rᶜ is hydrogen, and Rᵈ is n-pentyl; or
when

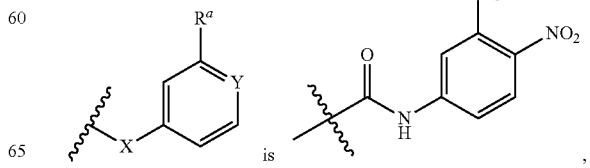

Ar is not

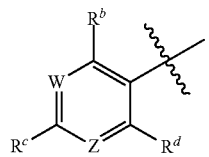

wherein W is CH, Z is nitrogen, $R^b$ is —SCH$_3$, $R^c$ is hydrogen, and $R^d$ is n-pentyl; or
when

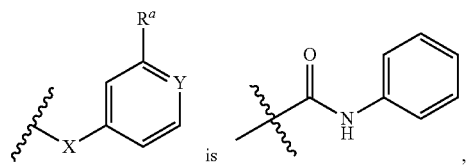 is

Ar is not

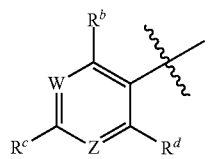

wherein W and Z are each CH, $R^b$ is hydrogen, $R^c$ is hydrogen, and $R^d$ is —OCH$_2$CH$_2$N(CH$_3$)$_2$; or
when

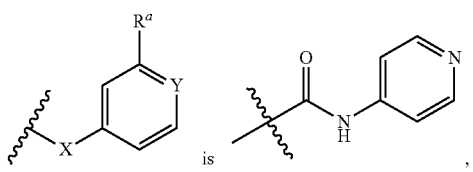 is

Ar is not

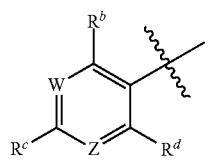

wherein W and Z are each CH, $R^b$ is ethoxy, $R^c$ is hydrogen, and $R^d$ is —OCH$_2$CH$_2$N(CH$_3$)$_2$; or when

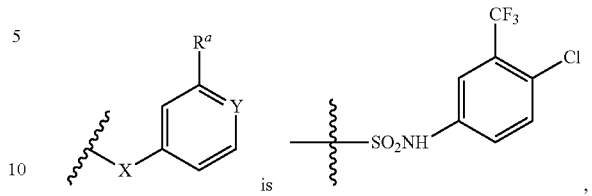 is

Ar is not

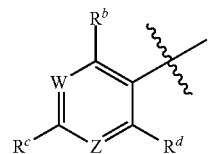

wherein W and Z are each CH, $R^b$ is methoxy, $R^c$ is hydrogen, and $R^d$ is —SCH$_2$CH$_2$N(CH$_3$)$_2$; or
when

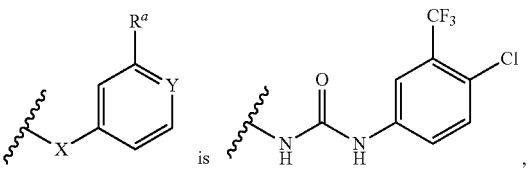 is

Ar is not

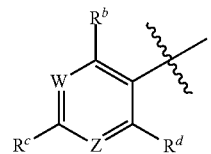

wherein W and Z are each CH, $R^b$ is —OCH$_2$C(O)OR wherein R is H or alkyl, $R^c$ is hydrogen, and $R^d$ is —Sethyl; or
when

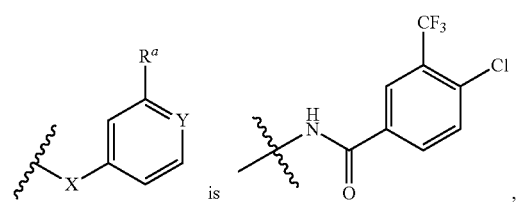 is

Ar is not

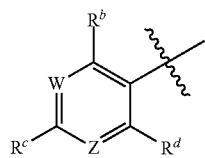

wherein W and Z are each CH, $R^b$ is ethoxy, $R^c$ is hydrogen, and $R^d$ is —SCH$_2$CH$_2$N(CH$_3$)$_2$.

In some embodiments, Ar is

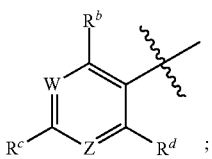

$R^a$ is H, halogen, or haloalkyl;
$R^b$ is H, O—(C$_1$-C$_6$-alkyl), O—(C$_3$-C$_8$-cycloalkyl), O—(C$_2$-C$_6$-alkenyl), O—(C$_3$-C$_8$-heterocycloalkyl), N(R$^{10}$)—(C$_1$-C$_6$-alkyl), N(R$^{10}$)—(C$_3$-C$_8$-cycloalkyl), O—(C$_2$-C$_6$-alkyl)-N(R$^{10}$)$_2$, O—(C$_3$-C$_8$-cycloalkyl)-N(R$^{10}$)$_2$, N(R$^{10}$)—(C$_2$-C$_6$-alkyl)-N(R$^{10}$)$_2$, —(C$_1$-C$_6$-alkyl)-N(R$^{10}$)$_2$, —(C$_1$-C$_6$-alkyl)-R$^3$, O—(C$_1$-C$_6$-alkyl)-R$^3$, O—(C$_3$-C$_8$-cycloalkyl)-R$^3$, N(R$^{10}$)—(C$_1$-C$_6$-alkyl)-R$^3$, O-aryl, or O-heteroaryl;
$R^c$ is H, —(C$_1$-C$_6$-alkyl), or O—(C$_1$-C$_6$-alkyl);
$R^d$ is H, OH, C$_1$-C$_6$-alkyl, O—(C$_3$-C$_8$-cycloalkyl), O—(C$_3$-C$_8$-heterocycloalkyl), O—(C$_1$-C$_6$-alkyl), —O—(C$_2$-C$_6$-alkenyl), O—(C$_2$-C$_6$-alkyl)-N(R$^{10}$)$_2$, —(C$_1$-C$_6$-alkyl)-R$^3$, O—(C$_1$-C$_6$-alkyl)-R$^3$, N(R$^{10}$)—(C$_1$-C$_6$-alkyl)-R$^3$, —N(R$^{10}$)—(C$_1$-C$_6$-alkyl), —N(R$^{10}$)—(C$_3$-C$_8$-cycloalkyl), —N(R$^{10}$)—(C$_3$-C$_8$-heterocycloalkyl), —N(R$^{10}$)—(C$_2$-C$_6$-alkenyl), N(R$^{10}$)—(C$_2$-C$_6$-alkyl)-N(R$^{10}$)$_2$, —(C$_1$-C$_6$-alkyl)-N(R$^{10}$)$_2$, O-aryl, N-aryl, O-heteroaryl, or N-heteroaryl;
W and Z are CR$^1$;
X is —CO—, —CON(R$^{10}$)—, —CON(R$^{10}$)(CH$_2$)$_n$—, —(CH$_2$)$_n$N(R$^{10}$)—, —C=N—; or
Ar and X together form

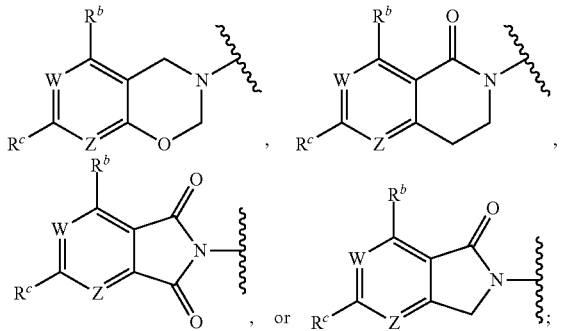

Y is CR$^2$;
$R^1$ is H, halogen, O—(C$_1$-C$_6$-alkyl), O—(C$_2$-C$_6$-alkyl)N(R$^{10}$)$_2$;
$R^2$ is halogen or haloalkyl;
$R^3$ is cycloalkylamino, optionally containing a heteroatom selected from N(R$^{10}$), O and S;

$R^{10}$ is independently H, —(C$_1$-C$_4$-alkyl), —(C$_1$-C$_4$-haloalkyl), —(C$_3$-C$_8$-cycloalkyl), —(C$_3$-C$_8$-heterocycloalkyl), aryl or heteroaryl; and
n is an integer from 1-3, or a pharmaceutically acceptable salt thereof.

In some embodiments, compounds of formula (I) have histone acetyltransferase (HAT) activity. In some embodiments, the compounds of formula (I) are HAT modulators. In some embodiments, the compounds of formula (I) are HAT activators. In some embodiments, the compounds of formula (I) are HAT inhibitors. In some embodiments, the compounds of formula (I) exhibit high selectivity for HAT and blood-brain-barrier (BBB) permeability. In some embodiments, the compounds of formula (I) exhibit high selectivity for HAT. In some embodiments, the compounds of formula (I) exhibit blood-brain-barrier (BBB) permeability.

Another aspect of the invention provides a method for screening compounds of formula (I) to treat conditions associated with accumulated amyloid-beta peptide deposits. In some embodiments, the method comprises (a) administering a compound of formula (I) to an animal model of amyloid-beta peptide deposit accumulation; and (b) selecting a compound of formula (I) that can modulate histone acetylation after administration in an animal model of amyloid-beta peptide deposit accumulation.

Another aspect of the invention provides a method for reducing amyloid beta (Aβ) protein deposits in a subject wherein the method comprises administering to the subject an effective amount of a compound of formula (I) or a composition comprising a compound of formula (I) thereby decreasing Aβ protein deposits in the subject. In some embodiments, a compound of formula (I) is administered. In some embodiments, a composition comprising a compound of formula (I) is administered. In some embodiments, the subject exhibits abnormally elevated levels of amyloid beta plaques. In some embodiments, the subject is afflicted with Alzheimer's disease, Lewy body dementia, inclusion body myositis, or cerebral amyloid angiopathy. In some embodiments, the Aβ protein deposit comprises an Aβ$_{40}$ isomer, an Aβ$_{42}$ isomer, or a combination of isomers. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is a compound of formula (I). In some embodiments, the compound is compounds 1-26, or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides a method for treating Alzheimer's Disease in a subject, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is a compound of formula (I). In some embodiments, the compound is compounds 1-26, or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides a method for treating Alzheimer's Disease in a subject, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is a compound of formula (I). In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides a method for increasing memory retention in a subject afflicted with a neurodegenerative disease, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is a compound of formula (I). In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides a method for increasing synaptic plasticity in a subject afflicted with a neurodegenerative disease, the method comprising administering to a subject a therapeutic amount of a composition that increases histone acetylation in the subject, wherein the composition comprises a compound of formula (I). In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In some embodiments, synaptic plasticity comprises learning, memory, or a combination thereof. In some embodiments, synaptic plasticity comprises long term potentiation (LTP). In some embodiments, the compound is a compound of formula (I). In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides a method for ameliorating symptoms of Parkinson's Disease in a subject, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof. In some embodiments, the symptoms of Parkinson's Disease comprise tremor, bradykinesia, dyskinesia, rigidity, postural instability, dystonia, akathisia, dementia, impaired gross motor coordination, or a combination of the listed symptoms. In some embodiments, the postural instability comprises impaired imbalance, impaired coordination, or a combination thereof.

Another aspect of the invention also provides a method for treating cancer in a subject, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the cancer comprises B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, lung cancer, liver cancer, non-Hodgkins lymphoma, Hodgkins lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, or medullary carcinoma. In some embodiments, the compound is a compound of formula (I). In some embodiments, the compound is any of compounds 1-26 or any combination thereof.

Another aspect of the invention provides a method for treating Huntington's Disease in a subject, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides for a method of treating a neurodegenerative disease in a subject, the method comprising administering to a subject a therapeutic amount of a compound of formula (I) or a composition comprising a compound of formula (I). In some embodiments, a compound of formula (I) is administered. In some embodiments, a composition comprising a compound of formula (I) is administered. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In other embodiments, synaptic plasticity comprises learning, memory, or a combination thereof. In some embodiments, synaptic plasticity comprises long term potentiation (LTP). In some embodiments, the compound is a compound of formula (I). In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

Another aspect of the invention provides for a method of decreasing inclusion bodies in a subject afflicted with a neurodegenerative disorder, the method comprising administering to the subject an effective amount of a compound of formula (I) or a composition comprising a compound of formula (I). In some embodiments, a compound of formula (I) is administered. In some embodiments, a composition comprising a compound of formula (I) is administered. In some embodiments, the inclusion bodies comprise beta-amyloid peptides, native and phosphorylated Tau proteins, native and phosphorylated alpha-synuclein, lipofuscin, cleaved TARDBP (TDB-43), or a combination thereof. In other embodiments, the subject exhibits abnormally elevated levels of amyloid beta plaques. In some embodiments, the beta-amyloid peptides comprises an $A\beta_{40}$ isomer, an $A\beta_{42}$ isomer, or a combination of isomers. In some embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In other embodiments, synaptic plasticity comprises learning, memory, or a combination thereof. In some embodiments, synaptic plasticity comprises long term potentiation (LTP). In some embodiments, the compound is a compound of formula (I). In some embodiments, the compound is any of compounds 1-26 or any combination thereof. In some embodiments, the compound increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

DETAILED DESCRIPTION OF THE INVENTION

Figure 1:
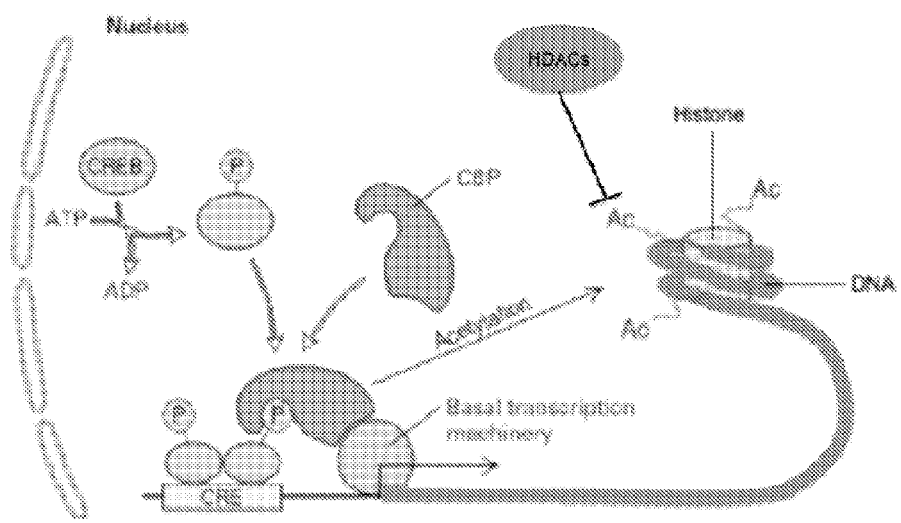
FIG. 1 is a schematic showing that CBP is recruited to act as a bridge between DNA-bound phosphorylated CREB and the basal transcription machinery located at the start site of transcription. In addition, CBP acts as a HAT, making the chromatin more accessible and increasing the transcription of memory associated genes. Unlike CBP, HDACs remove an acetyl group from histones, thus restricting access of the transcriptional machinery to the DNA (figure was modified from Lodish H., B. A., Zipursky L S., Matsudaira P., Baltimore D., Darnell J., Molecular Cell Biology. 4 ed. 2000, New York: W. H. Freeman and Company).
Figure 2:
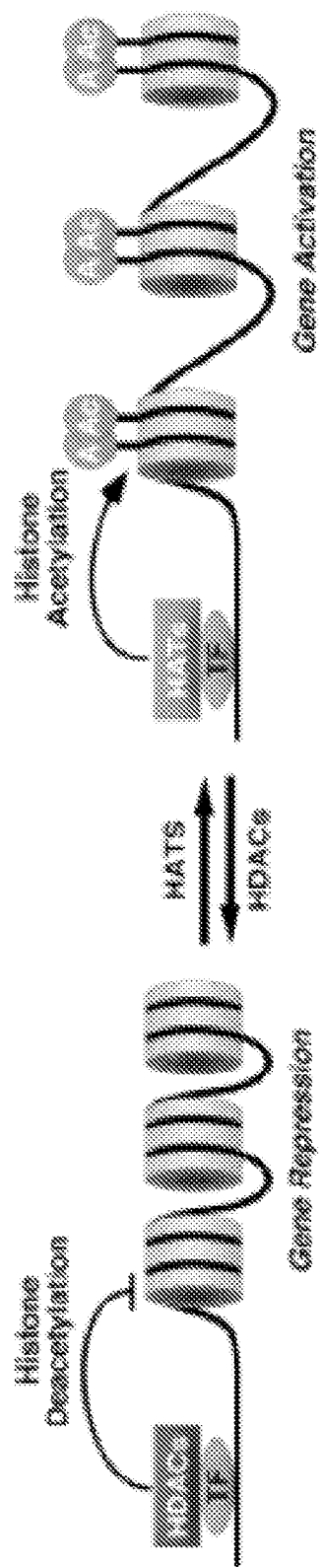
FIG. 2 is a schematic of histone acetylation and the role of HATs.
Figure 3:
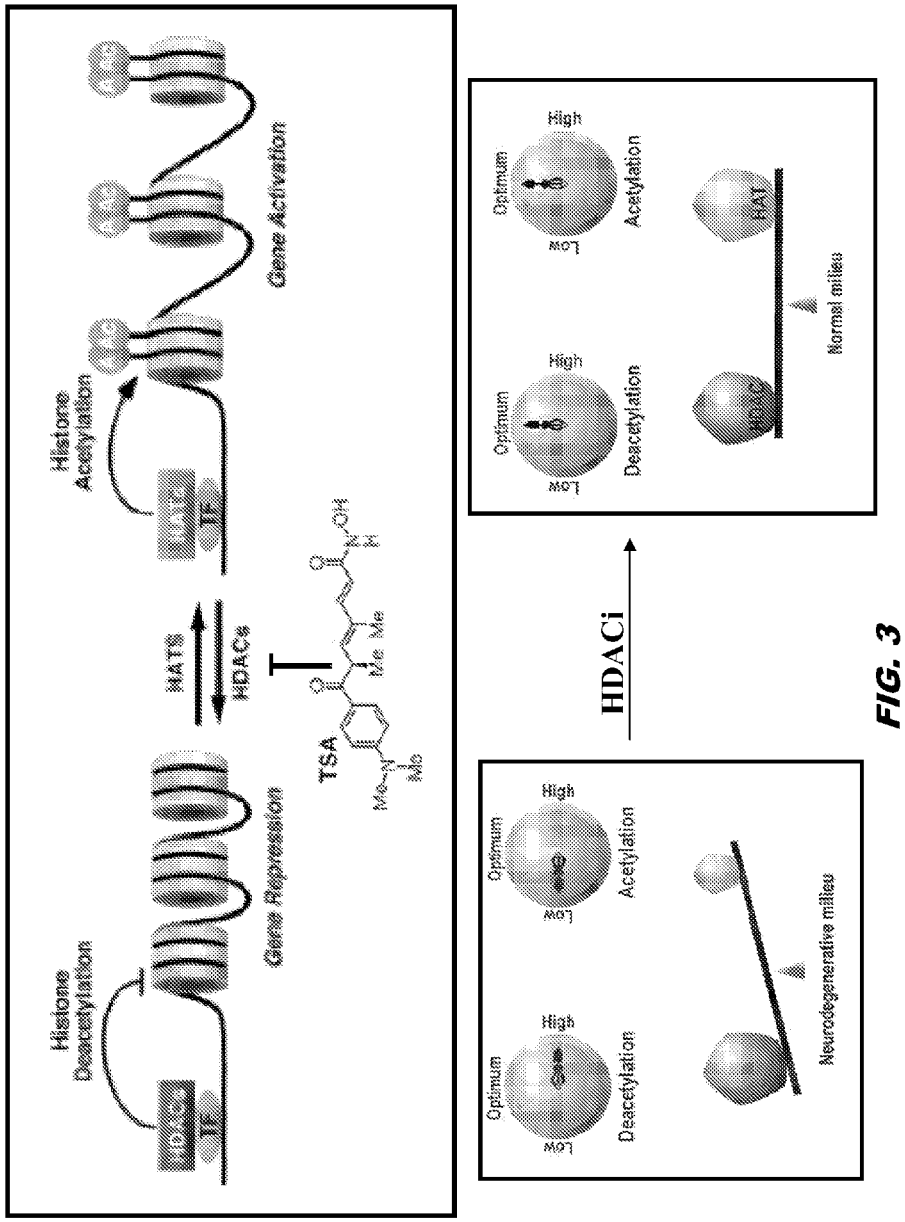
FIG. 3 is a schematic showing the role of a HDAC inhibitor (HDACi; e.g., TSA) in histone acetylation and deacetylation.

In one aspect, the invention is directed to a compound of formula (I).

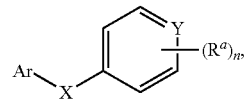

wherein,
Ar is

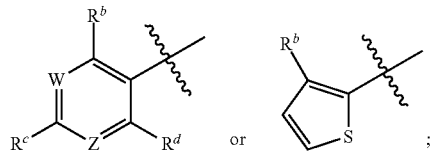

$R^a$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$;

$R^b$ is H, $C_1$-$C_6$-alkyl, $C_2$-$C_6$-alkenyl, $C_3$-$C_8$-cycloalkyl, $C_2$-$C_6$-heteroalkyl, $C_3$-$C_8$-heterocycloalkyl, aryl, heteroaryl, O—($C_1$-$C_6$-alkyl), O—($C_3$-$C_8$-cycloalkyl), O—($C_2$-$C_6$-alkenyl), O—($C_3$-$C_8$-heterocycloalkyl), N($R^{10}$)—($C_1$-$C_6$-alkyl), N($R^{10}$)—($C_3$-$C_8$-cycloalkyl), S—($C_1$-$C_6$-alkyl), O—($C_2$-$C_6$-alkyl)-N($R^{10}$)$_2$, O—($C_3$-$C_8$-cycloalkyl)-N($R^{10}$)$_2$, N($R^{10}$)—($C_2$-$C_6$-alkyl)-N($R^{10}$)$_2$, —($C_1$-$C_6$-alkyl)-N($R^{10}$)$_2$, —($C_1$-$C_6$-alkyl)-$R^3$, O—($C_1$-$C_6$-alkyl)-$R^3$, O—($C_3$-$C_8$-cycloalkyl)-$R^3$, N($R^{10}$)—($C_1$-$C_6$-alkyl)-$R^3$, O-aryl, or O-heteroaryl;

$R^c$ is H, —($C_1$-$C_6$-alkyl), O—($C_1$-$C_6$-alkyl), C(=O)NH-phenyl, wherein phenyl is substituted with one or more halo or haloalkyl;

$R^d$ is H, OH, —($C_1$-$C_6$-alkyl), O—($C_3$-$C_8$-cycloalkyl), O—($C_3$-$C_8$-heterocycloalkyl), O—($C_2$-$C_6$-alkenyl), O—($C_1$-$C_6$-alkyl), O—($C_2$-$C_6$-alkyl)-N($R^{10}$)$_2$, —($C_1$-$C_6$-alkyl)-$R^3$, O—($C_1$-$C_6$-alkyl)-$R^3$, N($R^{10}$)—($C_1$-$C_6$-alkyl)-$R^3$, —N($R^{10}$)—($C_2$-$C_6$-alkyl), —N($R^{10}$)—($C_2$-$C_6$-alkenyl), —N($R^{10}$)—($C_3$-$C_8$-cycloalkyl), —N($R^{10}$)—($C_3$-$C_8$-heterocycloalkyl), N($R^{10}$)—($C_2$-$C_6$-alkyl)-N($R^{10}$)$_2$, —($C_1$-$C_6$-alkyl)-N($R^{10}$)$_2$, S—($C_2$-$C_6$-alkyl)-N($R^{10}$)$_2$, $OCH_2C(O)O$-alkyl, O-aryl, N-aryl, O-heteroaryl, or N-heteroaryl;

W and Z are independently N or $CR^1$;
X is —CO—, —CON($R^{10}$)—, —CON($R^{10}$)($CH_2$)$_n$—, —($CH_2$)$_n$CON($R^{10}$)—, —($CH_2$)$_n$CON($R^{10}$)($CH_2$)$_n$—, —SON($R^{10}$)—, —SON($R^{10}$)($CH_2$)$_n$—, —$SO_2$N($R^{10}$)—, —$SO_2$N($R^{10}$)($CH_2$)$_n$—, —N($R^{10}$)C(=O)N($R^{10}$)—, —N($R^{10}$)CO—, —N($R^{10}$)CO($CH_2$)$_n$—, or —N($R^{10}$)CO($CH_2$)$_n$—, —($CH_2$)$_n$N($R^{10}$)—, —C=N—; or
Ar and X together form

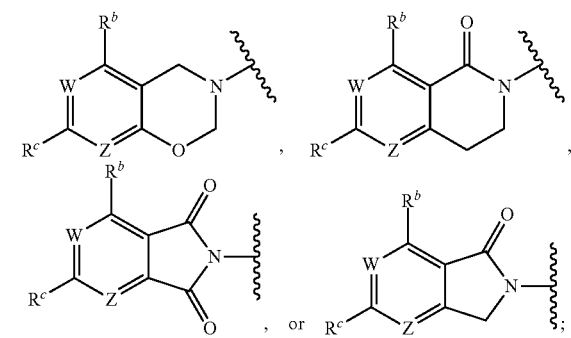

Y is N or CR$^2$;

R$^1$ is H, halogen, O—(C$_1$-C$_6$-alkyl), O—(C$_2$-C$_6$-alkyl)N(R$^{10}$)$_2$;

R$^2$ is H, C$_1$-C$_6$-alkyl, C$_1$-C$_6$-haloalkyl, O—(C$_1$-C$_6$-alkyl), O—(C$_1$-C$_6$-haloalkyl), halogen, CN, or NO$_2$;

R$^3$ is cycloalkylamino, optionally containing a heteroatom selected from N(R$^{10}$), O and S;

R$^{10}$ is independently H, —(C$_1$-C$_4$-alkyl), —(C$_1$-C$_4$-haloalkyl), —(C$_3$-C$_8$-cycloalkyl), —(C$_3$-C$_8$-heterocycloalkyl), aryl or heteroaryl; and each n is independently an integer from 1-3, or a pharmaceutically acceptable salt or hydrate thereof; with the proviso that Ar is not

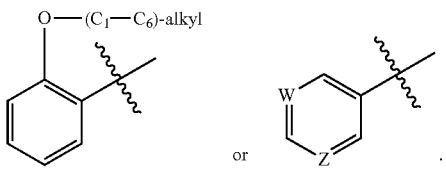

In some embodiments, the compound of formula (I) is

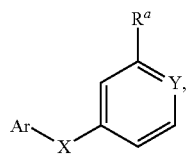

wherein,
Ar is

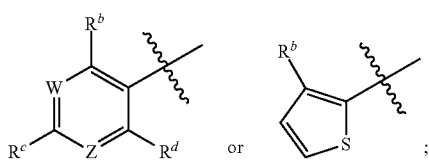

R$^a$ is H, halogen, or haloalkyl;

R$^b$ is H, C$_1$-C$_6$-alkyl, C$_2$-C$_6$-alkenyl, C$_3$-C$_8$-cycloalkyl, C$_2$-C$_6$-heteroalkyl, C$_3$-C$_8$-heterocycloalkyl, aryl, heteroaryl, O—(C$_1$-C$_6$-alkyl), O—(C$_3$-C$_8$-cycloalkyl), O—(C$_2$-C$_6$-alkenyl), O—(C$_3$-C$_8$-heterocycloalkyl), N(R$^{10}$)—(C$_1$-C$_6$-alkyl), N(R$^{10}$)—(C$_3$-C$_8$-cycloalkyl), S—(C$_1$-C$_6$-alkyl), O—(C$_2$-C$_6$-alkyl)-N(R$^{10}$)$_2$, O—(C$_3$-C$_8$-cycloalkyl)-N(R$^{10}$)$_2$, N(R$^{10}$)—(C$_2$-C$_6$-alkyl)-N(R$^{10}$)$_2$, —(C$_1$-C$_6$-alkyl)-N(R$^{10}$)$_2$, —(C$_1$-C$_6$-alkyl)-R$^3$, O—(C$_1$-C$_6$-alkyl)-R$^3$, O—(C$_3$-C$_8$-cycloalkyl)-R$^3$, N(R$^{10}$)—(C$_1$-C$_6$-alkyl)-R$^3$, O-aryl, or O-heteroaryl;

R$^c$ is H, —(C$_1$-C$_6$-alkyl), O—(C$_1$-C$_6$-alkyl), C(=O)NH-phenyl, wherein phenyl is substituted with one or more halo or haloalkyl;

R$^d$ is H, OH, C$_1$-C$_6$-alkyl, O—(C$_3$-C$_8$-cycloalkyl), O—(C$_3$-C$_8$-heterocycloalkyl), O—(C$_2$-C$_6$-alkenyl), O—(C$_1$-C$_6$-alkyl), O—(C$_2$-C$_6$-alkyl)-N(R$^{10}$)$_2$, —(C$_1$-C$_6$-alkyl)-R$^3$, O—(C$_1$-C$_6$-alkyl)-R$^3$, N(R$^{10}$)—(C$_1$-C$_6$-alkyl)-R$^3$, —N(R$^{10}$)—(C$_1$-C$_6$-alkyl), —N(R$^{10}$)—(C$_2$-C$_6$-alkenyl), —N(R$^{10}$)—(C$_3$-C$_8$-cycloalkyl), —N(R$^{10}$)—(C$_3$-C$_8$-heterocycloalkyl), N(R$^{10}$)—(C$_2$-C$_6$-alkyl)-N(R$^{10}$)$_2$, —(C$_1$-C$_6$-alkyl)-N(R$^{10}$)$_2$, S—(C$_2$-C$_6$-alkyl)-N(R$^{10}$)$_2$, OCH$_2$C(O)O-alkyl, O-aryl, N-aryl, O-heteroaryl, or N-heteroaryl;

W and Z are independently N or CR$^1$;

X is —CO—, —CON(R$^{10}$)—, —CON(R$^{10}$)(CH$_2$)$_n$—, —(CH$_2$)$_n$CON(R$^{10}$)—, —(CH$_2$)$_n$CON(R$^{10}$)(CH$_2$)$_n$—, —SON(R$^{10}$)—, —SON(R$^{10}$)(CH$_2$)$_n$—, —SO$_2$N(R$^{10}$)—, —SO$_2$N(R$^{10}$)(CH$_2$)$_n$—, —N(R$^{10}$)C(=O)N(R$^{10}$)—, —N(R$^{10}$)CO—, —N(R$^{10}$)CO(CH$_2$)$_n$—, or —N(R$^{10}$)CO(CH$_2$)$_n$—, —(CH$_2$)$_n$N(R$^{10}$)—, —C=N—; or

Ar and X together form

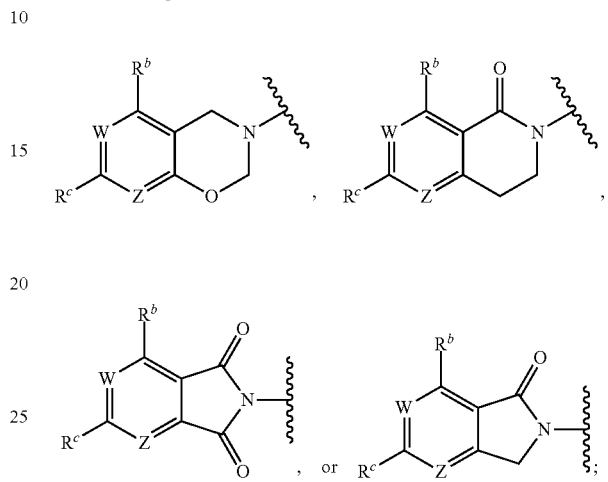

Y is N or CR$^2$;

R$^1$ is H, halogen, O—(C$_1$-C$_6$-alkyl), O—(C$_2$-C$_6$-alkyl)N(R$^{10}$)$_2$;

R$^2$ is H, halogen, haloalkyl, —NO$_2$ or CN;

R$^3$ is cycloalkylamino, optionally containing a heteroatom selected from N(R$^{10}$), O and S;

R$^{10}$ is independently H, —(C$_1$-C$_4$-alkyl), —(C$_1$-C$_4$-haloalkyl), —(C$_3$-C$_8$-cycloalkyl), —(C$_3$-C$_8$-heterocycloalkyl), aryl or heteroaryl; and n is an integer from 1-3, or a pharmaceutically acceptable salt thereof; with the proviso that Ar is not

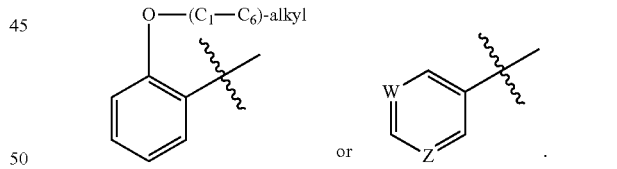

In some embodiments, R$^a$ is H, halogen, or haloalkyl;

Y is CH, C-halogen, or C—CN;

R$^b$ is H, O—(C$_1$-C$_2$-alkyl), S—(C$_1$-C$_2$-alkyl), O-cyclopentyl, OCH$_2$CH$_2$N(CH$_3$)$_2$, or CH$_2$CH$_2$CH$_2$N(CH$_3$)$_2$;

R$^c$ is H; C(=O)NH-phenyl, wherein phenyl is substituted with one or more halo or haloalkyl;

R$^d$ is H, C$_1$-C$_5$-alkyl, OH, O-alkyl, OCH$_2$CH$_2$N(CH$_3$)$_2$, CH$_2$CH$_2$CH$_2$N(CH$_3$)$_2$, SCH$_2$CH$_2$N(CH$_3$)$_2$, or OCH$_2$C(=O)O-alkyl;

Z is CH, C—O—(C$_1$-C$_2$-alkyl), C—OCH$_2$CH$_2$N(CH$_3$)$_2$; and

X is CONH, SONH, SO$_2$NH, NHC(=O)NH, or NHCO, or a pharmaceutically acceptable salt or hydrate thereof.

In some embodiments, when

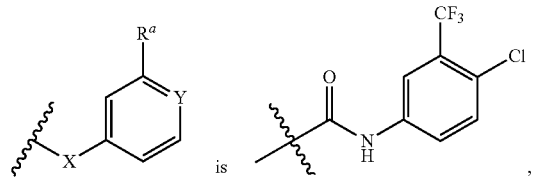

is

Ar is not

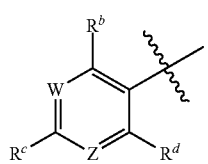

wherein
W and Z are each CH, $R^b$ is ethoxy, $R^c$ is hydrogen, and $R^d$ is —OCH$_2$CH$_2$N(CH$_3$)$_2$ or OH; or
wherein W is C—OCH$_2$CH$_2$N(CH$_3$)$_2$, Z is CH, $R^b$ is hydrogen, $R^c$ is hydrogen, and $R^d$ is hydrogen; or
wherein W and Z are each CH, $R^b$ is cyclopentyloxy, $R^c$ is hydrogen, and $R^d$ is —OCH$_2$CH$_2$N(CH$_3$)$_2$; or
wherein W and Z are each CH, $R^b$ is —OCH$_2$CH$_2$N(CH$_3$)$_2$, $R^c$ is —C(O)NH-(3-CF$_3$, 4-Cl-phenyl), and $R^d$ is —OCH$_2$CH$_2$N(CH$_3$)$_2$; or
wherein W is CH, Z is C-ethoxy, $R^b$ is ethoxy, $R^c$ is —C(O)NH-(3-CF$_3$, 4-Cl-phenyl), and $R^d$ is hydrogen; or
wherein W and Z are each CH, $R^b$ is —CH$_2$CH$_2$CH$_2$N(CH$_3$)$_2$, $R^c$ is —C(O)NH-(3-CF$_3$, 4-Cl-phenyl), and $R^d$ is —CH$_2$CH$_2$CH$_2$N(CH$_3$)$_2$ or hydrogen; or
wherein W and Z are each CH, $R^b$ is ethoxy, $R^c$ is —C(O)NH-(3-CF$_3$, 4-Cl-phenyl), and $R^d$ is hydrogen or —OCH$_2$CH$_2$N(CH$_3$)$_2$; or
wherein W and Z are nitrogen, $R^b$ is ethoxy, $R^c$ is hydrogen, and $R^d$ is —OCH$_2$CH$_2$N(CH$_3$)$_2$;
when

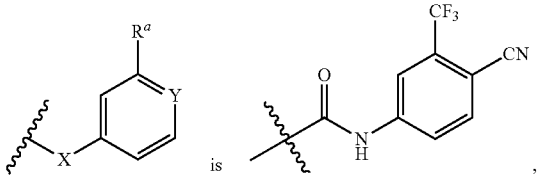

is

Ar is not

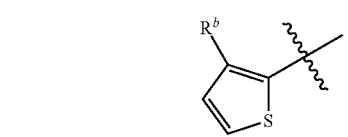

wherein $R^b$ is ethoxy, or Ar is not

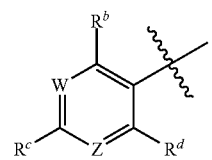

wherein W and Z are each CH, $R^b$ is —Sethyl, $R^c$ is hydrogen, and $R^d$ is n-pentyl; or
when

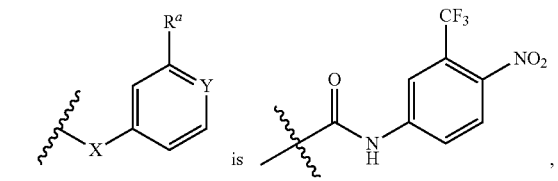

is

Ar is not

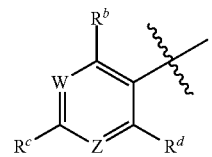

wherein W is CH, Z is nitrogen, $R^b$ is —SCH$_3$, $R^c$ is hydrogen, and $R^d$ is n-pentyl; or
when

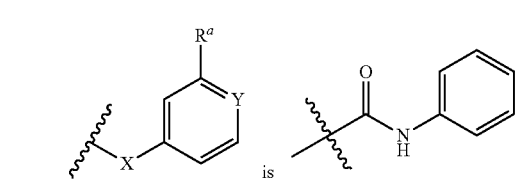

is

Ar is not

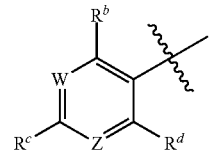

wherein W and Z are each CH, $R^b$ is hydrogen, $R^c$ is hydrogen, and $R^d$ is —OCH$_2$CH$_2$N(CH$_3$)$_2$; or
when

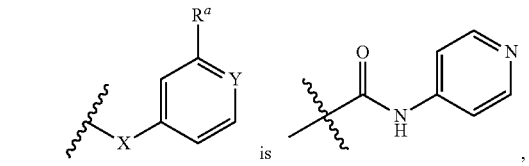

is

Ar is not

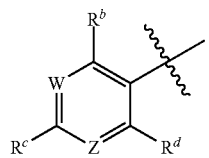

wherein W and Z are each CH, $R^b$ is ethoxy, $R^c$ is hydrogen, and $R^d$ is —OCH$_2$CH$_2$N(CH$_3$)$_2$; or
when

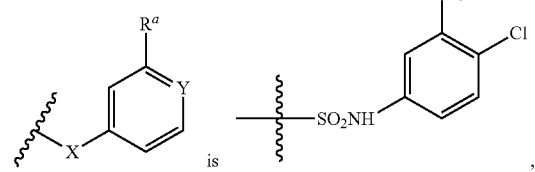

Ar is not

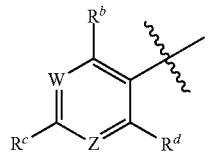

wherein W and Z are each CH, $R^b$ is methoxy, $R^c$ is hydrogen, and $R^d$ is —SCH$_2$CH$_2$N(CH$_3$)$_2$; or
when

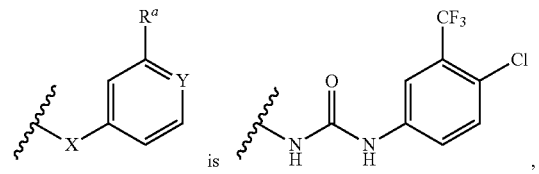

Ar is not

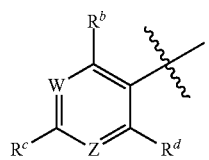

wherein W and Z are each CH, $R^b$ is —OCH$_2$C(O)OR wherein R is H or alkyl, $R^c$ is hydrogen, and $R^d$ is —Sethyl; or when

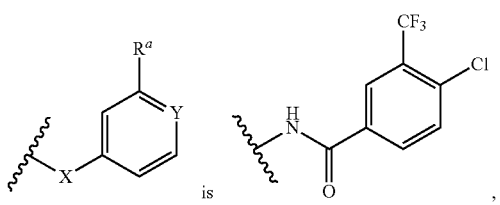

Ar is not

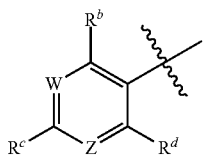

wherein W and Z are each CH, $R^b$ is ethoxy, $R^c$ is hydrogen, and $R^d$ is —SCH$_2$CH$_2$N(CH$_3$)$_2$.

Thus, in some embodiments, the compound of formula (I) is not selected from the group consisting of

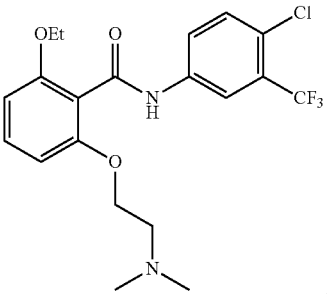

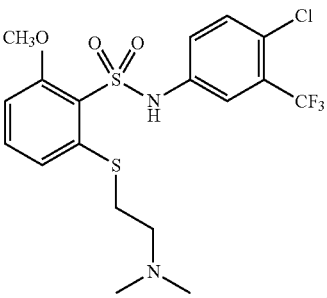

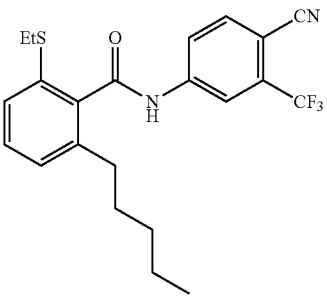

23
-continued
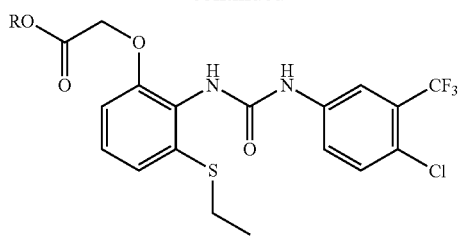
wherein R is H or alkyl,
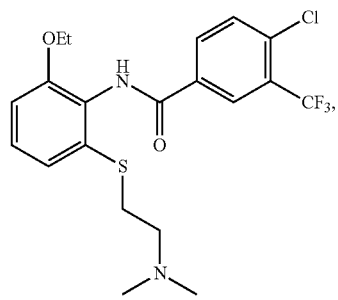
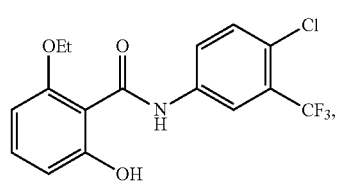
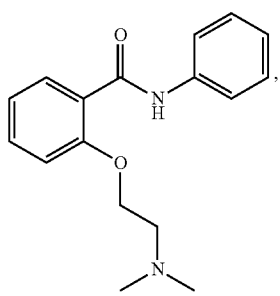
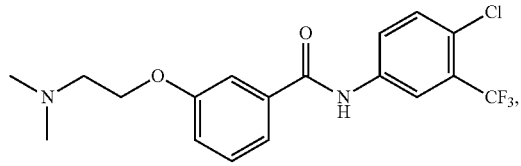
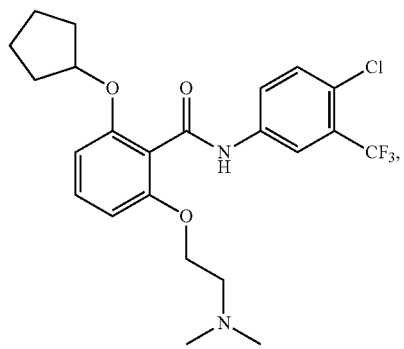
24
-continued
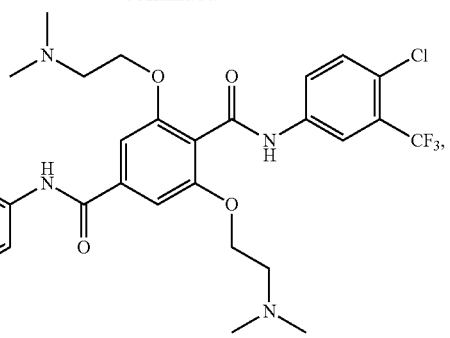
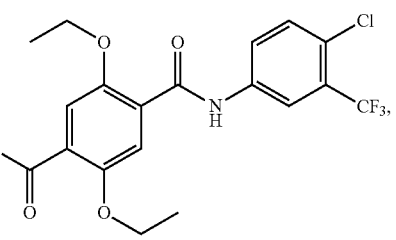
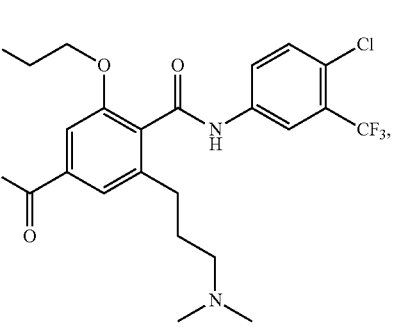
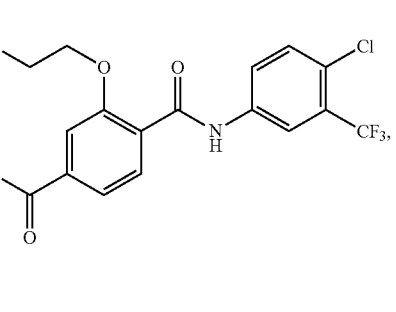
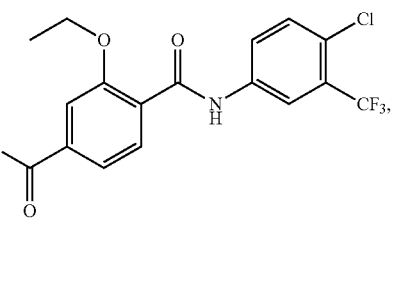

-continued

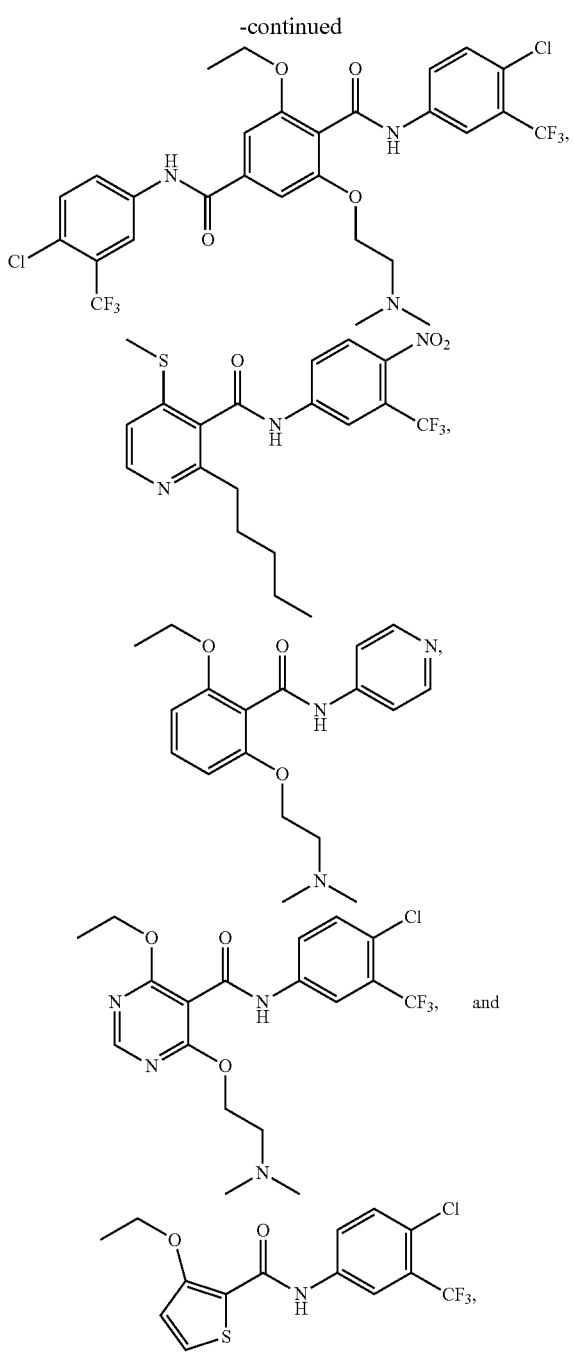

or a pharmaceutically acceptable salt thereof.

In some embodiments Ar is

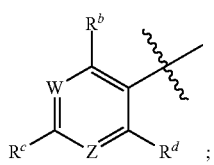

$R^a$ is H, halogen, or haloalkyl;
$R^b$ is H, O—($C_1$-$C_6$-alkyl), O—($C_3$-$C_8$-cycloalkyl), O—($C_2$-$C_6$-alkenyl), O—($C_3$-$C_8$-heterocycloalkyl), N($R^{10}$)—($C_1$-$C_6$-alkyl), N($R^{10}$)—($C_3$-$C_8$-cycloalkyl), O—($C_2$-$C_6$-alkyl)-N($R^{10}$)$_2$, O—($C_3$-$C_8$-cycloalkyl)-N($R^{10}$)$_2$, N($R^{10}$)—($C_2$-$C_6$-alkyl)-N($R^{10}$)$_2$, —($C_1$-$C_6$-alkyl)-N($R^{10}$)$_2$, —($C_1$-$C_6$-alkyl)-$R^3$, O—($C_1$-$C_6$-alkyl)-$R^3$, O—($C_3$-$C_8$-cycloalkyl)-$R^3$, N($R^{10}$)—($C_1$-$C_6$-alkyl)-$R^3$, O-aryl, or O-heteroaryl;

$R^c$ is H, —($C_1$-$C_6$-alkyl), or O—($C_1$-$C_6$-alkyl);

$R^d$ is H, OH, $C_1$-$C_6$-alkyl, O—($C_3$-$C_8$-cycloalkyl), O—($C_3$-$C_8$-heterocycloalkyl), O—($C_1$-$C_6$-alkyl), —O—($C_2$-$C_6$-alkenyl), O—($C_2$-$C_6$-alkyl)-N($R^{10}$)$_2$, —($C_1$-$C_6$-alkyl)-$R^3$, O—($C_1$-$C_6$-alkyl)-$R^3$, N($R^{10}$)—($C_1$-$C_6$-alkyl)-$R^3$, —N($R^{10}$)—($C_1$-$C_6$-alkyl), —N($R^{10}$)—($C_3$-$C_8$-cycloalkyl), —N($R^{10}$)—($C_3$-$C_8$-heterocycloalkyl), —N($R^{10}$)—($C_2$-$C_6$-alkenyl), N($R^{10}$)—($C_2$-$C_6$-alkyl)-N($R^{10}$)$_2$, —($C_1$-$C_6$-alkyl)-N($R^{10}$)$_2$, O-aryl, N-aryl, O-heteroaryl, or N-heteroaryl;

W and Z are $CR^1$;

X is —CO—, —CON($R^{10}$)—, —CON($R^{10}$)(CH$_2$)$_n$—, —(CH$_2$)$_n$N($R^{10}$)—, —C=N—; or

Ar and X together form

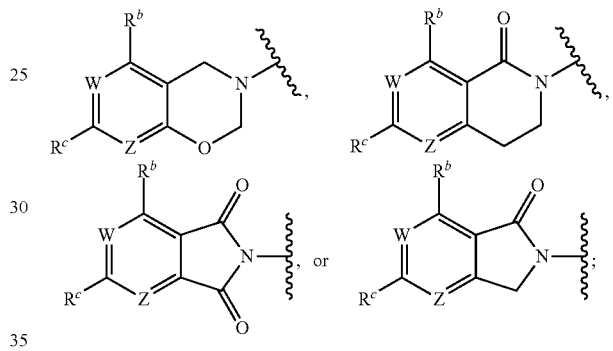

Y is $CR^2$;

$R^1$ is H, halogen, O—($C_1$-$C_6$-alkyl), O—($C_2$-$C_6$-alkyl)N($R^{10}$)$_2$;

$R^2$ is halogen or haloalkyl;

$R^3$ is cycloalkylamino, optionally containing a heteroatom selected from N($R^{10}$), O and S;

$R^{10}$ is independently H, —($C_1$-$C_4$-alkyl), —($C_1$-$C_4$-haloalkyl), —($C_3$-$C_8$-cycloalkyl), —($C_3$-$C_8$-heterocycloalkyl), aryl or heteroaryl; and n is an integer from 1-3, or a pharmaceutically acceptable salt thereof.

In some embodiments, Ar is

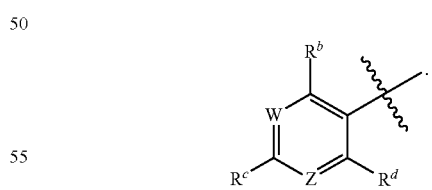

In some embodiments, Ar is

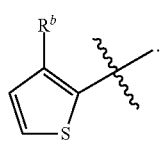

In some embodiments, $R^a$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$. In some embodiments, $R^a$ is $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$. In some embodiments, $R^a$ is $C_1$-$C_3$-alkyl, $C_1$-$C_3$-haloalkyl, O—($C_1$-$C_3$-haloalkyl), halogen, CN, or $NO_2$. In some embodiments, $R^a$ is H, halogen, or $C_1$-$C_6$-haloalkyl. In some embodiments, $R^a$ is H, halogen, or $C_1$-$C_3$-haloalkyl. In some embodiments, $R^a$ is halogen or $C_1$-$C_6$-haloalkyl. In some embodiments, $R^a$ is halogen or $C_1$-$C_3$-haloalkyl. In some embodiments, $R^a$ is $C_1$-$C_6$-haloalkyl. In some embodiments, $R^a$ is $C_1$-$C_3$-haloalkyl. In some embodiments, $R^a$ is $CF_3$.

In some embodiments, $R^b$ is H, O—($C_2$-$C_6$-alkyl), S—($C_2$-$C_6$-alkyl), O—($C_3$-$C_8$-cycloalkyl), O—($C_2$-$C_6$-alkenyl), O—($C_3$-$C_8$-heterocycloalkyl), $N(R^{10})$—($C_1$-$C_6$-alkyl), $N(R^{10})$—($C_3$-$C_8$-cycloalkyl), O—($C_2$-$C_6$-alkyl)-N$(R^{10})_2$, O—($C_3$-$C_8$-cycloalkyl)-N$(R^{10})_2$, $N(R^{10})$—($C_2$-$C_6$-alkyl)-N$(R^{10})_2$, —($C_1$-$C_6$-alkyl)-N$(R^{10})_2$, —($C_1$-$C_6$-alkyl)-$R^3$, O—($C_1$-$C_6$-alkyl)-$R^3$, O—($C_3$-$C_8$-cycloalkyl)-$R^3$, $N(R^{10})$—($C_1$-$C_6$-alkyl)-$R^3$, O-aryl, or O-heteroaryl. In some embodiments, $R^b$ is H, O—($C_2$-$C_6$-alkyl), S—($C_2$-$C_6$-alkyl), O—($C_3$-$C_8$-cycloalkyl), O—($C_2$-$C_6$-alkenyl), O—($C_3$-$C_8$-heterocycloalkyl), $N(R^{10})$—($C_1$-$C_6$-alkyl), $N(R^{10})$—($C_3$-$C_8$-cycloalkyl), O—($C_2$-$C_6$-alkyl)-N$(R^{10})_2$, O-aryl, or O-heteroaryl. In some embodiments, $R^b$ is H, O—($C_2$-$C_6$-alkyl), S—($C_2$-$C_6$-alkyl), O—($C_3$-$C_8$-cycloalkyl), $N(R^{10})$—($C_1$-$C_6$-alkyl), or $N(R^{10})$—($C_3$-$C_8$-cycloalkyl). In some embodiments, $R^b$ is H, O—($C_2$-$C_4$-alkyl), or $N(R^{10})$—($C_1$-$C_6$-alkyl). In some embodiments, $R^b$ is H or O—($C_2$-$C_6$-alkyl). In some embodiments, $R^b$ is H or O—($C_2$-$C_4$-alkyl). In some embodiments, $R^b$ is O—($C_2$-$C_4$-alkyl) or S—($C_2$-$C_4$-alkyl). In some embodiments, $R^b$ is O—($C_2$-$C_4$-alkyl). In some embodiments, $R^b$ is O-ethyl, O-propyl, O-butyl, O-cyclopropyl, or O-cyclobutyl. In some embodiments, $R^b$ is O-ethyl, O-propyl, or O-butyl. In some embodiments, $R^b$ is O-ethyl.

In some embodiments, $R^c$ is H, —($C_1$-$C_6$-alkyl), or O—($C_2$-$C_6$-alkyl). In some embodiments, $R^c$ is H or —($C_1$-$C_6$-alkyl). In some embodiments, $R^c$ is H, or O—($C_2$-$C_6$-alkyl). In some embodiments, $R^c$ is H.

In some embodiments, $R^d$ is H, OH, $C_1$-$C_6$-alkyl, O—($C_3$-$C_8$-cycloalkyl), O—($C_3$-$C_8$-heterocycloalkyl), O—($C_1$-$C_6$-alkyl), —O—($C_2$-$C_6$-alkenyl), O—($C_2$-$C_6$-alkyl)-N$(R^{10})_2$, —($C_1$-$C_6$-alkyl)-$R^3$, O—($C_1$-$C_6$-alkyl)-$R^3$, $N(R^{10})$—($C_1$-$C_6$-alkyl)-$R^3$, —$N(R^{10})$—($C_1$-$C_6$-alkyl), —$N(R^{10})$—($C_3$-$C_8$-cycloalkyl), —$N(R^{10})$—($C_3$-$C_8$-heterocycloalkyl), —$N(R^{10})$—($C_2$-$C_6$-alkenyl), $N(R^{10})$—($C_2$-$C_6$-alkyl)-N$(R^{10})_2$, —($C_1$-$C_6$-alkyl)-N$(R^{10})_2$, O-aryl, N-aryl, O-heteroaryl, or N-heteroaryl. In some embodiments, $R^d$ is O—($C_3$-$C_8$-cycloalkyl), O—($C_3$-$C_8$-heterocycloalkyl), O—($C_1$-$C_6$-alkyl), —O—($C_2$-$C_6$-alkenyl), O—($C_2$-$C_6$-alkyl)-N$(R^{10})_2$, —($C_1$-$C_6$-alkyl)-$R^3$, O—($C_1$-$C_6$-alkyl)-$R^3$, $N(R^{10})$—($C_1$-$C_6$-alkyl)-$R^3$, —$N(R^{10})$—($C_1$-$C_6$-alkyl), —$N(R^{10})$—($C_3$-$C_8$-cycloalkyl), —$N(R^{10})$—($C_3$-$C_8$-heterocycloalkyl), —$N(R^{10})$—($C_2$-$C_6$-alkenyl), $N(R^{10})$—($C_2$-$C_6$-alkyl)-N$(R^{10})_2$, —($C_1$-$C_6$-alkyl)-N$(R^{10})_2$, O-aryl, N-aryl, O-heteroaryl, or N-heteroaryl. In some embodiments, $R^d$ is O—($C_1$-$C_6$-alkyl), —O—($C_2$-$C_6$-alkenyl), O—($C_2$-$C_6$-alkyl)-N$(R^{10})_2$, —($C_1$-$C_6$-alkyl)-$R^3$, O—($C_1$-$C_6$-alkyl)-$R^3$, $N(R^{10})$—($C_1$-$C_6$-alkyl)-$R^3$, $N(R^{10})$—($C_2$-$C_6$-alkyl)-N$(R^{10})_2$, —($C_1$-$C_6$-alkyl)-N$(R^{10})_2$, O-aryl, N-aryl, O-heteroaryl, or N-heteroaryl. In some embodiments, $R^d$ is O—($C_2$-$C_6$-alkyl)-N$(R^{10})_2$, —($C_1$-$C_6$-alkyl)-$R^3$, O—($C_1$-$C_6$-alkyl)-$R^3$, $N(R^{10})$—($C_1$-$C_6$-alkyl)-$R^3$, $N(R^{10})$—($C_2$-$C_6$-alkyl)-N$(R^{10})_2$, or —($C_1$-$C_6$-alkyl)-N$(R^{10})_2$. In some embodiments, $R^d$ is O—($C_2$-$C_4$-alkyl)-N$(R^{10})_2$, —($C_1$-$C_4$-alkyl)-$R^3$, O—($C_1$-$C_4$-alkyl)-$R^3$, $N(R^{10})$—($C_1$-$C_4$-alkyl)-$R^3$, $N(R^{10})$—($C_2$-$C_4$-alkyl)-N$(R^{10})_2$, or —($C_1$-$C_4$-alkyl)-N$(R^{10})_2$. In some embodiments, $R^d$ is O—($C_2$-$C_4$-alkyl)-N$(R^{10})_2$ or O—($C_1$-$C_4$-alkyl)-$R^3$.

In some embodiments, W and Z are independently N or $CR^1$. In some embodiments, W is N. In some embodiments, Z is N. In some embodiments, W is $CR^1$. In some embodiments, Z is $CR^1$. In some embodiments, W and Z are both $CR^1$. In some embodiments, W and Z are both N.

In some embodiments, X is —CO—, —CON($R^{10}$)—, —CON($R^{10}$)(CH$_2$)$_n$—, —(CH$_2$)$_n$N($R^{10}$)—, or —C=N—. In some embodiments, X is —CO—, —CON($R^{10}$)—, —CON($R^{10}$)(CH$_2$)—, or —C=N—. In some embodiments, X is —CON($R^{10}$)— or —C=N—. In some embodiments, X is —CON($R^{10}$).

In some embodiments, Ar and X together form

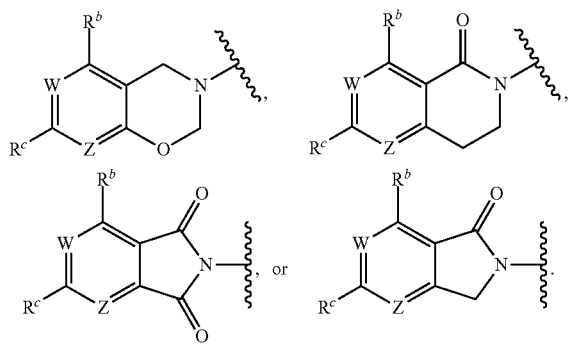

In some embodiments, Ar and X together form

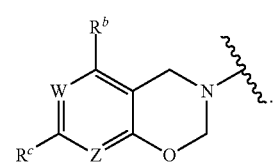

In some embodiments, Ar and X together form

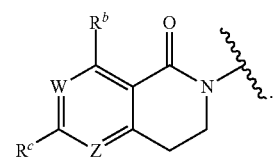

In some embodiments, Ar and X together form

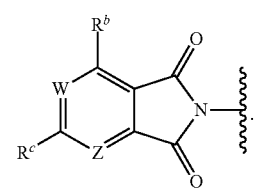

In some embodiments, Ar and X together form

In some embodiments, the compound of formula (I) is

In some embodiments, the compound of formula (I) is

In some embodiments, the compound of formula (I) is

In some embodiments, the compound of formula (I) is

In some embodiments, the compound of formula (I) is

In some embodiments, Y is N or $CR^2$. In some embodiments, Y is $CR^2$. In some embodiments, Y is N.

In some embodiments, $R^1$ is H, halogen, O—($C_1$-$C_6$-alkyl), or O—($C_2$-$C_6$-alkyl)N($R^{10}$)$_2$. In some embodiments, $R^1$ is H or halogen. In some embodiments, $R^1$ is H. In some embodiments, $R^1$ is halogen. In some embodiments, $R^1$ is Cl or F.

In some embodiments, $R^2$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$. In some embodiments, $R^2$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$. In some embodiments, $R^2$ is $C_1$-$C_3$-alkyl, $C_1$-$C_3$-haloalkyl, O—($C_1$-$C_3$-haloalkyl), halogen, CN, or $NO_2$. In some embodiments, $R^2$ is H, halogen, $C_1$-$C_6$-haloalkyl, $NO_2$ or CN. In some embodiments, $R^2$ is H, halogen, or $C_1$-$C_6$-haloalkyl. In some embodiments, $R^2$ is H, halogen, or $C_1$-$C_3$-haloalkyl. In some embodiments, $R^2$ is halogen or $C_1$-$C_6$-haloalkyl. In some embodiments, $R^2$ is halogen or $C_1$-$C_3$-haloalkyl. In some embodiments, $R^2$ is $C_1$-$C_6$-haloalkyl. In some embodiments, $R^2$ is halogen. In some embodiments, $R^2$ is $C_1$-$C_3$-haloalkyl. In some embodiments, $R^2$ is Cl, F, or $CF_3$.

In some embodiments, $R^3$ is cycloalkylamino, optionally containing a heteroatom selected from N($R^{10}$), O and S. In some embodiments, $R^3$ is $C_3$-$C_8$-cycloalkylamino, optionally containing a heteroatom selected from N($R^{10}$), O and S. In some embodiments, $R^3$ is $C_3$-$C_8$-cycloalkylamino, morpolinyl, thiomorpholinyl, or N-alkylpiperazinyl. In some embodiments, $R^3$ is piperidinyl, or N-alkylpiperazinyl.

In some embodiments, $R^{10}$ is independently H, —($C_1$-$C_4$-alkyl), —($C_1$-$C_4$-haloalkyl), —($C_3$-$C_8$-cycloalkyl), aryl or heteroaryl. In some embodiments, $R^{10}$ is independently H, —($C_1$-$C_4$-alkyl), or —($C_1$-$C_4$-haloalkyl). In some embodiments, $R^{10}$ is independently H or —($C_1$-$C_4$-alkyl). In some embodiments, $R^{10}$ is independently H or —($C_1$-$C_2$-alkyl). In some embodiments, $R^{10}$ is independently H or methyl. In some embodiments, $R^{10}$ is H.

In some embodiments, the compound of formula (I) is a compound of formula (I-a), (I-a)

wherein,
$R^a$ is H, halogen, or haloalkyl;
$R^b$ is O—($C_1$-$C_6$)-alkyl or S—($C_1$-$C_6$)-alkyl;
$R^d$ is ($C_1$-$C_6$)-alkyl or O—($C_1$-$C_6$)-alkyl-N($CH_3$)$_2$;
Y is haloalkyl, C—CN, C—$NO_2$, or N;
W is CH or N; and
Z is CH or N, or a pharmaceutically acceptable salt or hydrate thereof.

In some embodiments, the compound of formula (I) is a compound of formula (I-b), (I-b)

wherein
R$^a$ is haloalkyl;
R$^2$ is CN; and
R$^b$ is O—(C$_1$-C$_6$)-alkyl, or a pharmaceutically acceptable salt or hydrate thereof.

In some embodiments, the compound of formula (I) is a compound of formula (I-c),

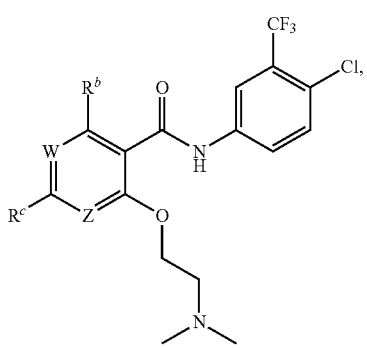

wherein
R$^b$ is H, or ethoxyl;
W and Z are independently CH, C—Cl, or C—OEt; and
R$^c$ is H, ethoxyl, or methyl; or a pharmaceutically acceptable salt or hydrate thereof.

In some embodiments of formula (I-c), R$^b$ is ethoxyl, W and Z are each CH, and R$^c$ is methyl. In some embodiments of formula (I-c), R$^b$ is ethoxyl, W and Z are each C—Cl, and R$^c$ is H. In other embodiments of formula (I-c), R$^b$ is H, W is ethoxyl, R$^c$ is H, and Z is CH. In a further embodiment of formula (I-c), R$^b$ is H, W and Z are each CH, and R$^c$ is ethoxyl.

In some embodiments, the compound of formula (I) is

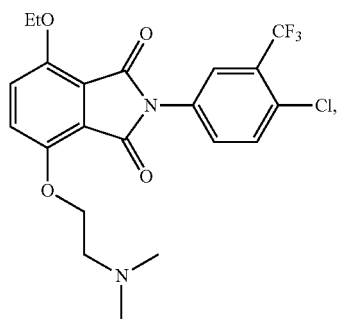 [SMILES: CCOc1ccc(OCCN(C)C)c2c1C(=O)N(c1ccc(Cl)c(C(F)(F)F)c1)C2=O]

or a pharmaceutically acceptable salt or hydrate thereof.

In some embodiments, the compound of formula (I) is compound (I-d),

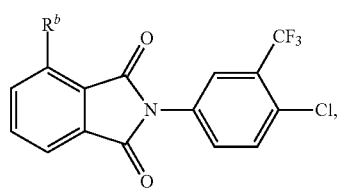

wherein R$^b$ is —O-ethyl, —O—CH$_2$CH$_2$N(CH$_3$)$_2$, —NH-ethyl, or —NH—CH$_2$CH$_2$N(CH$_3$)$_2$, or a pharmaceutically acceptable salt or hydrate thereof.

In some embodiments, the compound of formula (I) is compound (I-e),

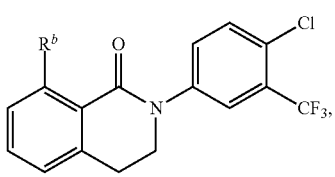

wherein R$^b$ is —O-ethyl, —O—CH$_2$CH$_2$N(CH$_3$)$_2$, —NH-ethyl, or —NH—CH$_2$CH$_2$N(CH$_3$)$_2$, or a pharmaceutically acceptable salt or hydrate thereof.

In some embodiments, the compound of formula (I) is compound (I-f),

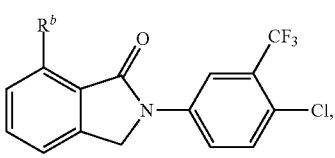

wherein R$^b$ is —O-ethyl, —O—CH$_2$CH$_2$N(CH$_3$)$_2$, —NH-ethyl, or —NH—CH$_2$CH$_2$N(CH$_3$)$_2$, or a pharmaceutically acceptable salt or hydrate thereof.

In some embodiments, the compound of formula (I) is compound (I-g):

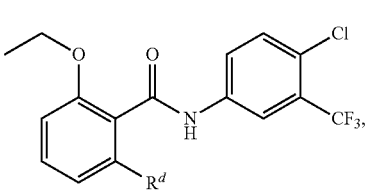

wherein R$^d$ is —O—(C$_1$-C$_6$)-alkyl, —NH—(C$_1$-C$_6$)-alkyl, —O—(C$_2$-C$_6$)-alkenyl, —NH—(C$_2$-C$_6$)-alkenyl, —O—(C$_3$-C$_8$)-cycloalkyl, —NH—(C$_3$-C$_8$)-cycloalkyl, —O—(C$_3$-C$_8$)-heterocycloalkyl, —NH—(C$_3$-C$_8$)-heterocycloalkyl, —O-aryl, —N-aryl, —O-heteroaryl, —N-heteroaryl, —O—(C$_1$-C$_6$)-alkyl-N(R$^{10}$)$_2$, —NH—(C$_1$-C$_6$)-alkyl-N(R$^{10}$)$_2$, —O—(C$_1$-C$_6$-alkyl)-R$^3$, or —NH—(C$_1$-C$_6$-alkyl)-R$^3$.

In some embodiments, the compound of formula (I) is compound (I-h):

(I-h)

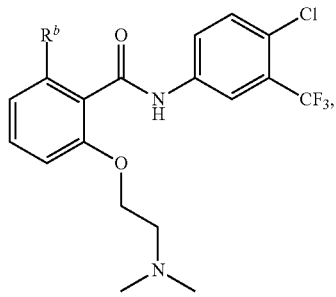

wherein $R^b$ is —O—($C_1$-$C_6$)-alkyl, —O—($C_2$-$C_6$)-alkenyl, —O—($C_3$-$C_8$)-cycloalkyl, —O—($C_3$-$C_8$)-heterocycloalkyl, —O-aryl, —O-heteroaryl, —O—($C_1$-$C_6$)-alkyl-N($R^{10}$)$_2$, or —O—($C_1$-$C_6$-alkyl)-$R^3$.

In some embodiments, the compound of formula (I) is compound (I-i):

(I-i)

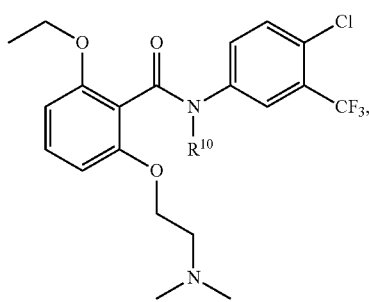

wherein $R^{10}$ is H, —($C_1$-$C_4$-alkyl), —($C_1$-$C_4$-haloalkyl), —($C_3$-$C_8$-cycloalkyl), —($C_3$-$C_8$-heterocycloalkyl), aryl or heteroaryl. In some embodiments, $R^{10}$ is H, —($C_1$-$C_4$-alkyl), —($C_1$-$C_4$-haloalkyl), —($C_3$-$C_8$-cycloalkyl), or —($C_3$-$C_8$-heterocycloalkyl). In some embodiments, $R^{10}$ is H, —($C_1$-$C_4$-alkyl), or —($C_1$-$C_4$-haloalkyl). In some embodiments, $R^{10}$ is H, or —($C_1$-$C_4$-alkyl). In some embodiments, $R^{10}$ is —($C_1$-$C_4$-alkyl).

In some embodiments, the compound of formula (I) is

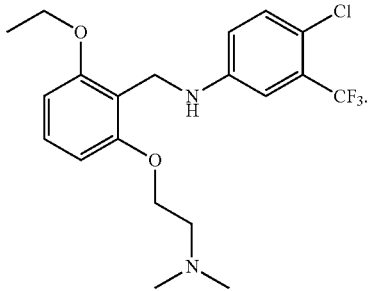 [SMILES: CCOc1cccc(OCCN(C)C)c1CNc1ccc(Cl)c(C(F)(F)F)c1]

In some embodiments, the compound of formula (I) is

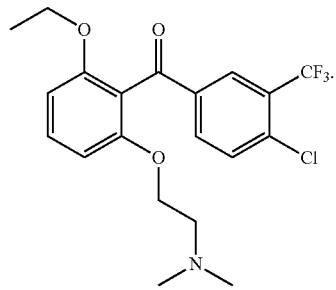 [SMILES: CCOc1cccc(OCCN(C)C)c1C(=O)c1ccc(Cl)c(C(F)(F)F)c1]

In some embodiments, the compound of formula (I) is (I-j)

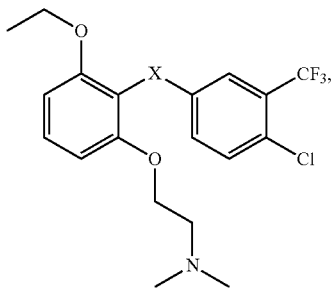

wherein X is CH$_2$CONH(CH$_2$)$_n$, and n is 0-3.

In some embodiments, the compound of formula (I) is (I-k)

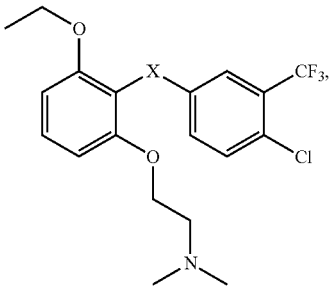

wherein X is CONH(CH$_2$)$_n$, and n is 0-3.

In some embodiments, the compound of formula (I) is (I-l)

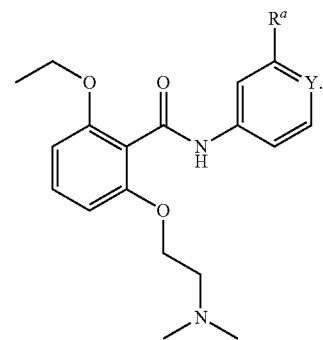

In some embodiments, the compound of formula (I) is a pharmaceutically acceptable salt. In some embodiments, the compound of formula (I) is a hydrate.

The term "HAT modulator" as used herein encompasses, for example, compound of formula (I) and subgenera and/or species thereof. For example, in some embodiments, the HAT modulator compound is a compound of formula (I). In some embodiments, the HAT modulator compound is a compound of formula (I-a), (I-b), (I-c), (I-d), (I-e), (I-f), (I-g), (I-h), (I-i), (I-j), (I-k), (I-l), or any combination thereof. In some embodiments, the compound of formula (I) is a compound of formula (I-a), (I-b), (I-c), (I-d), (I-e), (I-f), (I-g), (I-h), (I-i), (I-j), (I-k), (I-l), or any combination thereof. In some embodiments, the compound is any of compounds 1-26, or any combination thereof. In some embodiments, the compound of formula (I) is any of compounds 1-26, or any combination thereof. In some embodiments, the HAT modulator is a HAT activator. In some embodiments, the HAT modulator is a HAT inhibitor. The term "HAT modulator" may also apply as used elsewhere herein.

In some embodiments, the compound of formula (I) is a compound of formula (I-a). In some embodiments, the compound of formula (I) is a compound of formula (I-b). In some embodiments, the compound of formula (I) is a compound of formula (I-c). In some embodiments, the compound of formula (I) is a compound of formula (I-d). In some embodiments, the compound of formula (I) is a compound of formula (I-e). In some embodiments, the compound of formula (I) is a compound of formula (I-f). In some embodiments, the compound of formula (I) is a compound of formula (I-g). In some embodiments, the compound of formula (I) is a compound of formula (I-h). In some embodiments, the compound of formula (I) is a compound of formula (I-i). In some embodiments, the compound of formula (I) is a compound of formula (I-j). In some embodiments, the compound of formula (I) is a compound of formula (I-k). In some embodiments, the compound of formula (I) is a compound of formula (I-l). Each of the embodiments of formula (I) may be combined with one or more other embodiments of formula (I) to generate further embodiments of formula (I).

Early amnesic changes in Alzheimer's disease (AD) are thought to be linked to synaptic dysfunction. β-amyloid (Aβ), a peptide that is present in high amounts in the disease, has been found to inhibit memory (*Proc Natl Acad Sci USA*, 2006. 103(23): p. 8852-7; *Nat Neurosci*, 2005. 8(1): p. 79-84; each herein incorporated by reference in its entirety) and its electrophysiological model, long-term potentiation (LTP) (*Neuroreport*, 1997, 8(15), 3213-7; *Eur J Pharmacol*, 1999, 382(3), 167-75; *Proc Natl Acad Sci USA*, 2002, 99(20), 13217-21; *Nature*, 2002, 416(6880), 535-9; *J Neurosci Res*, 2000, 60(1), 65-72; *Proc Natl Acad Sci USA*, 1998, 95(11), 6448-53; each herein incorporated by reference in its entirety). Memory is known to be modulated by epigenetics through regulation of gene expression. Epigenetics is defined as the mechanism that changes gene expression by 'marking' DNA or its associated proteins, through processes such as DNA methylation and histone (H) modification, without changing the DNA sequence itself (*Biochem J*, 2001. 356(Pt 1): p. 1-10; herein incorporated by reference in its entirety). Modification of histones by, for example, the addition or removal of acetyl or methyl functional groups causes the chromatin structure to open or close, so that the information contained within the DNA is made more or less accessible to transcription factors. Deregulation of one of the epigenetic mechanisms may lead to memory disruption. For example, reduction of histone acetylation causes the chromatin structure to close, so that the information contained within the DNA can be less accessible to transcription factors and memory formation (*Biochem J*, 2001. 356(Pt 1): p. 1-10; herein incorporated by reference in its entirety).

Epigenetic modifications including acetylation of histones may contribute to gene expression changes important to learning and memory (*Science* 2010: 328(5979), 701-702; herein incorporated by reference in its entirety). Addition of acetyl groups to histones by histone acyltransferases (HAT) enhances gene expression, while their removal by histone deacetylases (HDAC) reduces gene expression. Reduction in histone acetylation has recently been linked to age-induced memory impairment and various neurodegenerative diseases (*Science* 2010: 328(5979), 701-702; herein incorporated by reference in its entirety). HDAC inhibitors have been shown to enhance memory in mice (*Nature* 459, 55-60 (7 May 2009); herein incorporated by reference in its entirety). Although clinical trials of several HDAC inhibitors are currently underway to try to prevent deacetylation, the alternative strategy of increasing histone acetylation by activating HAT has not been significantly explored. Histone acetylation is discussed in, for example, U.S. Patent Publication Nos. 2010/0166781; 2010/0144885; 2009/0076155; *Neuroscience* 2011, 194, 272-281; and *J. Phys. Chem B* 2007, 111(17), 4527-4534 (each of which herein incorporated by reference in its entirety).

Epigenetics is emerging as a new and powerful area for drug development in the field of memory. Currently used AD therapies have limited efficacy. Major efforts are underway to inhibit tangle formation, to combat inflammation and oxidative damage, and to decrease Aβ load in the brain (*Br J Pharmacol*, 2002. 137(5): p. 676-82; *J Neurosci*, 2005. 25(10): p. 2455-62; *Nature*, 1999. 400(6740): p. 173-7; each hereby incorporated by reference in its entirety). However, the role of tau, APP, Aβ, and the secretases in normal physiological function (*Eur J Pharmacol*, 1995. 284(3): p. R1-3; *Biochem Biophys Res Commun*, 1994. 205(3): p. 1829-35; *J Neurochem*, 1999. 73(2): p. 532-7; each hereby incorporated by reference in its entirety), can present a problem in providing effective and safe approaches to AD therapy. Many data strongly support an involvement of epigenetic mechanisms in memory dysfunction in neurodegenerative diseases including AD. HAT activators represent a new class of compounds that may effectively counteract the disease progression. Recently, a novel HAT activator has been demonstrated to improve contextual learning in healthy mice (WO 2011/072243; herein incorporated by reference in its entirety). In some embodiments, the invention comprises compounds that show comparable positive effects, but have improved drug-like characteristics.

The main strategy that is currently used to up-regulate histone acetylation involves inhibition of histone deacetylases (HDACs), enzymes that remove an acetyl group from histones. However, the pleiotropic effect of nonspecific HDAC inhibition can hamper the therapeutic potential of HDAC inhibitors (*J Virol*, 2001. 75(4): p. 1909-17; *J Virol*, 2003. 77(21): p. 11425-35; *Biochemistry*. 2008, Vanderbilt: Nashville. p. 167; *PLoS One*, 2009. 4(8): p. e6612; each of which herein incorporated by reference in its entirety). It has been demonstrated that hippocampal levels of two HATs, CBP and PCAF, are reduced following Aβ elevation. As discussed herein, the data is focused, in part, toward another target that also up-regulates histone acetylation, the HATs. Selective HAT activators that target specifically CBP and PCAF downstream of Aβ will be designed. For example, new HAT activators will be designed and synthesized which can treat AD; compounds with high affinity and good selectivity for selective HAT activators will be identified that target specifically CBP and PCAF; HAT activators will be assessed as to whether they have a good pharmacokinetic (PK) profile and are safe; select HAT activators will be examined for their ability to rescue synaptic dysfunction in APP/PS1 mice; and HAT activators will be further screened to determine beneficial effects against cognitive abnormalities in APP/PS1 mice.

The post-translational acetylation status of chromatin is governed by the competing activities of two classes of enzymes, HATs and HDACs. HDAC inhibitors enhance LTP and contextual fear memory, a form of associative memory in which animals must associate a neutral stimulus with an aversive one (*J Biol Chem*, 2004. 279(39): p. 40545-59; hereby incorporated by reference in its entirety). Also, memory and LTP deficits of CBP$^{+/-}$ mice were reversed by HDAC inhibition (*Neuron*, 2004. 42(6): p. 947-59; hereby incorporated by reference in its entirety). The potential of inhibiting HDACs to counteract neurodegenerative disorders has been widely explored (*Curr Drug Targets CNS Neurol Disord*, 2005. 4(1): p. 41-50; hereby incorporated by reference in its entirety). For instance, in a set of experiments, Tsai et al. have reported that HDAC inhibitors induced sprouting of dendrites, increased number of synapses, and reinstated learning and access to long-term memories in the CK-p25 Tg mouse model of neurodegeneration (*Nature*, 2007. 447(7141): p. 178-82; *EMBO J*, 2007. 26(13): p. 3169-79; each hereby incorporated by reference in its entirety). Moreover, in recent studies it has been shown that the HDAC inhibitor TSA ameliorates LTP and contextual fear conditioning (FC) in the double Tg APP(K670M:N671L)/PS1(M146L, line 6.2) (APP/PS1) mouse model of amyloid deposition (*J Alzheimers Dis*, 2009. 18(1): p. 131-9; hereby incorporated by reference in its entirety). Bolden et al., (*Nature Reviews Drug Discovery*, 2006, 5:769-84; hereby incorporated by reference in its entirety) describe the histone deacetylases family. HATs, however, have been investigated to a lesser extent.

HATs can be divided in two main groups, the nuclear HATs and cytoplasmic HATs (*Biochim Biophys Acta*, 2009. 1789(1): p. 58-68; hereby incorporated by reference in its entirety. Nuclear A-type HATs can be grouped into at least 4 different families based on sequence conservation within the HAT domain: Gcn5 and p300/CBP associated factor (PCAF), MYST (MOZ, Ybf2/Sas3, Sas2 and Tip60), p300 and CBP (named for the two human paralogs p300 and CBP) and Rtt109. While the Gcn5/PCAF and MYST families have homologs from yeast to man, p300/CBP is metazoan-specific, and Rtt109 is fungal-specific. Cytoplasmic B-type HATs, such as HAT1, are involved in histone deposition (*Biochim Biophys Acta*, 2009. 1789(1): p. 58-68; hereby incorporated by reference in its entirety). Marmorstein and Roth (*Curr Opin in Genet and Develop.*, 2001, 11:155-161; hereby incorporated by reference in its entirety) list the HAT families and their transcriptional-related functions.

Although other nuclear HAT families have been described, such as the steroid receptor coactivators, TAF250, ATF-2, and CLOCK, their HAT activities have not been investigated as extensively as the major HAT classes (*Biochim Biophys Acta*, 2009. 1789(1): p. 58-68; hereby incorporated by reference in its entirety). These 4 families show high sequence similarity within families but poor to no sequence similarity between families. Furthermore, the size of the HAT domain of the different families is different (*Biochim Biophys Acta*, 2009. 1789(1): p. 58-68; hereby incorporated by reference in its entirety). Interestingly, HATs are highly conserved in mammals (*Biochim Biophys Acta*, 2009. 1789(1): p. 58-68; hereby incorporated by reference in its entirety). Of all these HATs, three were shown to be involved in memory: CBP, p300 (*Nature*, 2007. 447(7141): p. 178-82; *EMBO J*, 2007. 26(13): p. 3169-79; each hereby incorporated by reference in its entirety), and PCAF (*J Alzheimers Dis*, 2009. 18(1): p. 131-9; hereby incorporated by reference in its entirety). Interestingly, both CBP and PCAF levels are reduced by Aβ elevation.

HAT activators can be a viable approach to enhance histone acetylation. Two scaffolds for HAT activators have been identified. The first one includes CTPB and its derivative CTB (*J Phys Chem B*, 2007. 111(17): p. 4527-34; *J Biol Chem*, 2003. 278(21): p. 19134-40; each hereby incorporated by reference in its entirety). The second one includes only one compound, nemorosone (*Chembiochem*. 11(6): p. 818-27; hereby incorporated by reference in its entirety). CTPB/CTB were found to be insoluble and membrane-impermeable (*J Phys Chem B*, 2007. 111(17): p. 4527-34; *J Biol Chem*, 2003. 278(21): p. 19134-40; each hereby incorporated by reference in its entirety). Moreover, CTPB has unfavorable characteristics to be used in CNS diseases (such as, for example, MW equal to 553.29, c log P equal to 12.70) and the c log P of CTB is 5.13. Nemorosone has a MW of 502 and a c log P of 8.42. Compounds that target CBP and PCAF can be useful in treatment of CNS disorders such as, for example, AD, as their endogenous expression is reduced following Aβ elevation.

HATs share a highly conserved motif containing an acetyl-CoA binding site. HATs can be involved in the pathology of cancer, asthma, neurodegenerative diseases and viral infection. HAT activators have been reported, but many compounds are neither soluble nor membrane permeant, which makes them poor drug candidates.

In some embodiments, the invention provides for compounds with histone acetyltransferase activity. In some embodiments, the compounds are HAT activators. In some embodiments, the compounds are HAT inhibitors. In some embodiments, the compounds have good HAT activation potency, high selectivity, reasonable pharmacokinetics and/or good permeability across the blood-brain-barrier (BBB). In some embodiments, these compounds can be used as therapy with decreased side effects for AD patients. In some embodiments, the compounds improve cognition or memory in AD and Alzheimer's-like pathologies, as well as minimize the side effects for subjects afflicted with other neurodegenerative diseases. In some embodiments, the compounds of the invention can also be developed as anti-cancer therapies. In some embodiments, acylation of histone proteins increases gene expression in a subject resulting in enhanced memory and cognition.

In some embodiments, the invention provides for the utilization of HAT agonists as memory enhancers in normal subjects (for example, a subject not afflicted with a neurodegenerative disease). In some embodiments, the invention provides for the utilization of HAT agonists as memory enhancers in aging subjects (for example, a subject that is greater than about 55 years old). In some embodiments, the invention provides for the utilization of HAT agonists as memory enhancers for other conditions associated with cognitive decrease/impairment. Non-limiting examples of conditions associated with cognitive decrease/impairment include a variety of syndromes associated with mental retardation and syndromes associated with learning disabilities, Parkinson's disease, Pick's disease, a Lewy body disease, amyotrophic lateral sclerosis, Huntington's disease, Creutzfeld-Jakob disease, Down syndrome, multiple system atrophy, neuronal degeneration with brain iron accumulation type I (Hallervorden-Spatz disease), pure autonomic failure, REM sleep behavior disorder, mild cognitive impairment (MCI), cerebral amyloid angiopathy (CAA), mild cognitive deficits, aging, vascular dementias mixed with Alzheimer's disease, a neurodegenerative disease characterized by abnormal amyloid deposition, and any combination thereof.

Eukaryotic DNA is highly organized and packaged into the nucleus. The organization and packaging are achieved through the addition of proteins, including core histones H2A, H2B, H3 and H4, which form a complex structure, the chromatin, together with DNA (See, for example, WO 2011/072243 and references cited therein). The modification of core histones is of fundamental importance to conformational changes of the chromatin. The level of acetylation is related to transcription activity, and then the acetylation induces an open chromatin confirmation that allows the transcription machinery access to promoters. Histone deacetylase (HDAC) and histone acetyltransferase (HAT) are enzymes that influence transcription by selectively deacetylating or acetylating the ε-amino groups of lysine located near the amino termini of core histone proteins. Chromatin acetylation correlates with transcriptional activity (euchromatin), whereas deacetylation correlates with gene silencing. Interestingly, it was shown that increased acetylation of H3 in area CA1 of the hippocampus (an area in the brain that plays an important role in long-tem memory) occurs following associative memory. Additionally, inhibiting HDAC, may manipulate changes in the chromatin and enhance the formation of long-tem memory.

Histone acetylation and deacetylation are increasingly recognized for their contribution to the tight regulation of gene activation and silencing, respectively. Deregulation of these mechanisms may lead to the disruption of memory-associated gene expression, resulting in a number of syndromes associated with mental retardation.

The DNA is firstly wrapped around an octamer complex of histones (H) to form nucleosomal units, giving the appearance of beads on a string (*Nature*, 2001. 409(6822): p. 860-921; herein incorporated by reference in its entirety). In turn, these nucleosomal units, fold into a higher-order chromatin fiber (*Cell*, 1999. 98(3): p. 285-94; herein incorporated by reference in its entirety). Each histone-octamer complex contains two copies of histones H3 and H4 bordered by two copies of histones 2A and 2B (*Cell*, 1999. 98(3): p. 285-94; herein incorporated by reference in its entirety). H1 and its avian variant H5 are linker histones that bind the nucleosome and both the entry and exit sites of the DNA, thus locking the DNA into place and allowing the formation of higher order structure. Every histone has a globular domain, which mediates histone-histone interactions, and an N-terminal 'tail' extension. The histone cores and in particular their tails, are targets for a considerable number of covalent modifications, such as acetylation, ubiquitination, sumoylation, phosphorylation, citrullination, ADP-ribosylation, and methylation (*Angew Chem Int Ed Engl*, 2005. 44(21): p. 3186-216; herein incorporated by reference in its entirety). Histone modifications associated with active gene transcription, such as H3 Lys4 methylation and H3 Lys56 acetylation, were found to lead to gene expression. On the other hand, histone modifications associated with the inactivation of gene transcription, such as H3 Lys27 methylation and H2A Lys119 ubiquitination were found to cause gene silencing. Histones 2B, 3 and 4 have been shown to be involved in memory processes (*Nature*, 2007. 447(7141): p. 178-82; *Neuron*, 2004. 42(6): p. 947-59; each herein incorporated by reference in its entirety).

Histone modifications and their combinations can be involved in gene regulation by modifying the chromatin accessibility and by acting as docking sites for transcription factors and modifying enzymes (*Bioessays*, 2005. 27(2): p. 164-75; *Nature*, 2000. 403(6765): p. 41-5; each herein incorporated by reference in its entirety). One of the most studied histone modifications is the acetylation of the evolutionary-conserved lysine residues on the histone N-termini by histone acetyltransferase (HAT). In contrast, histone deacetylation, catalyzed by histone deacetylase (HDAC), was found to package the DNA into a more condensed form, limiting the access of transcription factors and thus acting as a gene silencer (*Trends Biochem Sci*, 2000. 25(3): p. 121-6; herein incorporated by reference in its entirety). The HATs involved in the regulation of gene expression include at least three groups of enzymes (*J Biochem*, 2005. 138(6): p. 647-62; herein incorporated by reference in its entirety). The general control non-derepressible 5 (Gcn5) is the founding member of the Gcn5 N-acetyltransferases (GNATs). The GNAT family members include Gcn5, PCAF, E1p3, HAT1m Hpa2 and Nut1. The MYST family is named after the founding members of the family: Morf, Ybf2, Sas2 and Tip60 (*J Biochem*, 2005. 138(6): p. 647-62; herein incorporated by reference in its entirety). In addition, other proteins including CBP/p300, Taf1 and a number of nuclear receptor co-activators have been shown to possess intrinsic HAT activity. However, these proteins do not contain a consensus domain and therefore represent an 'orphan class' of HAT enzymes (*J Biochem*, 2005. 138(6): p. 647-62; herein incorporated by reference in its entirety).

HDACs form repressor complexes with transcription activators and with other HDACs (*Biochem J*, 2003. 370(Pt 3): p. 737-49; herein incorporated by reference in its entirety). Mammalian HDACs can be divided into the classical and the silent information regulator 2 (Sir2)-related protein (sirtruin) families (*Oncogene*, 2007. 26(37): p. 5310-8; herein incorporated by reference in its entirety). In humans, members of the classical family have another subdivision, which include class I, II and IV, that share sequence similarity and require Zn+ for deacetylase activity. Class I HDACs (HDAC1-3, HDAC8) are related to the yeast gene repressor Rpd3p, and are subunits of at least two distinct co-repressor complexes, the Sin3 complex and the NuRD complex. Class II HDACs (HDAC4-7, 9 and 10) are similar to the yeast Hda1p HDAC, they act as gene repressors and have been implicated in various roles in cell differentiation and development. Class IV comprises HDAC11, which has some features of both class I and II HDACs. The sirtruin family includes class III HDACs (SIRT1-7), which are similar to yeast Sir2. Class III HDACs are biochemically and structurally distinct from the classical family and require $NAD^+$ as a cofactor. HDACs appear to be involved in gene silencing and heterochromatin formation at centromeres and telomeres (*J Mol Biol*, 2004. 338(1): p. 17-31; herein incorporated by reference in its entirety).

Alterations in epigenetic modifications including acetylation and methylation of DNA and histones can contribute to gene expression changes in cancer and neurological diseases. Addition of acetyl group on histones by Histone Acetyltransferases (HATs) enhances gene expression, while its removal by Histone Deacetylases (HDAC) reduces gene expression. Reduction in histone acetylation has been found in a variety of ailments such as tumors, mood disorders, and neurodegenerative diseases. Examples of HATs include, but are not limited to GCN5, GCN5L, PCAF, HAT1, ELP3, HPA2, ESA1, SAS2, SAS3, TIP60, HBO1, MOZ, MORF, MOF, SRC1, SRC3, TIF2, GRIP1, ATF-2 [see Lee and Workman (2007) *Nat Rev Mol Cell Biol.,* 8(4):284-95, Marmorstein (2001) *J Molec Biol.* 311: 433-444; and Kimura et al., (2005) *J Biochem.* 138(6): 647-662, which are each hereby incorporated by reference in their entireties]. In some embodiments, the HAT modulator compound of the invention is directed to GCN5, GCN5L, HAT1, PCAF, or a combination thereof. In some embodiments, the HAT modulator compound of the invention is directed to proteins that possess intrinsic HAT activity, such as nuclear receptor co-activators (for example, CBP/p300 and Taf1). In some embodiments, the acetylation of H2, H3, and/or H4 histones is increased. In some embodiments, the HAT modulator compound is a compound of formula (I). In some embodiments, the HAT modulator compound is any of compounds 1-26 or any combination thereof.

Increasing histone acetylation has been shown to improve outcome in a wide variety of diseases as diverse as asthma, infectious disease and psychiatric diseases. Although clinical trials of several HDAC inhibitors are currently underway, the alternative strategy where by histone acetylation is increased by HAT modulator has not been extensively explored. For example, compounds in U.S. Patent Publication No. US2009/076155 and PCT Publication No. WO2004/053140 (which are each hereby incorporated by reference in their entireties) have poor solubility and membrane permeability.

No HAT activator is currently in clinical trials, however several HDAC inhibitors are currently in clinical trials. Some of these HDAC inhibitors (HDACi) have shown therapeutic efficacy in preclinical trials. Without being bound by theory, HAT modulators may be useful therapeutic candidates with a role similar to HDACi. However, many HAT activators have little solubility and membrane permeability, making them unsuitable as drugs.

Several HDACi are in trials for cancer, some of which are, for example, 4SC-202 (Nycomed, Germany), which is in a Preclinical stage; AR-42 (Arno therapeutics, Parsippany, N.J.) which is in a Preclinical stage; Belinostat (TopoTarget, Rockaway, N.J.) which is in Phase II clinical trials; and Entinostat (Bayer Schering) which is in Phase II clinical trials. For example, in Table 3 of Lane and Chabner (2009, *J Clin Oncol.,* 27(32):5459-68; incorporated by reference in its entirety), selected clinical trials of HDAC inhibitors are discussed, which include Vorinostat, Depsipeptide, and MGCD0103. In Table 2 of Lane and Chabner (2009, *J Clin Oncol.,* 27(32):5459-68; incorporated by reference in its entirety), selected HDAC inhibitors in clinical use or development are discussed, which include hydroxamic acid compounds (e.g., Vorinostat, Trichostatin A, LAQ824, Panobinostat, Belinostat, and ITF2357), cyclic tetrapeptide compounds (e.g., Depsipeptide), benzamide compounds (e.g., Entinostat and MGCD0103), and short-chain aliphatic acid compounds (e.g., valproic acid, phenyl butyrate, and pivanex).

Some HDACi are or were being developed for neurological diseases, such as an HDACi from Merck (Whitehouse Station, N.J.) that is being used for the treatment of neurodegenerative diseases; and HDACi from TopoTarget (Rockaway, N.J.) that was being used for the treatment of Huntington's disease, now discontinued; isovaleramide NPS-1776 (NPS Pharmaceutical, Bedminster, N.J.) that was being used for bipolar disorder, epilepsy, and migraines, now discontinued; and a histone acetyltransferase inhibitor for cancer from TopoTarget A/S (København, Denmark), which was discontinued in the preclinical stage.

In some embodiments, the synthesis of a new class of HAT modulators with improved solubility and membrane permeability are described. For example, the HAT modulators of formula (I) and/or compounds 1-26 may be used as adjuvant therapy in several cancers, psychiatric and neurodegenerative diseases and may improve efficacy and safety of treatment for these disorders. In some embodiments, the compounds of formula (I) and/or compounds 1-26 have improved solubility and membrane and Blood-brain-Barrier (BBB) permeability. See Abel and Zukin (2008) *Current Opinion in Pharmacology* 8:57-64; and Lee and Workman (2007) *Nat Rev Mol Cell Biol* 8:284-295 (each hereby incorporated by reference in their entireties).

In some embodiments, a HAT modulator compound is used to treat a cancer in a subject in need thereof. Non-limiting examples of cancers include B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, lung cancer, liver cancer, non-Hodgkins lymphoma, Hodgkins lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, and medullary carcinoma.

In some embodiments, a HAT modulator compound is used to treat a neurodegenerative disease in a subject in need thereof. Non-limiting examples of neurodegenerative diseases include Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Refsum's disease, Rett's syndrome, Tau-positive FrontoTemporal dementia, Tau-negative FrontoTemporal dementia, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

A schematic representation of the processes involved in gene transcription and memory is shown, for example, WO 2011/072243 (herein incorporated by reference in its entirety). In the brain, CREB phosphorylation is required for CREB ability to bind to CBP and to stimulate memory associated gene expression. CBP functions as a co-activator that facilitates interactions with the basal transcription machinery and through its HAT activity catalyzes acetylation of the histones, causing a loss in chromosomal repression and increase in the transcription of memory associated genes. Mutations in HAT domain CBP were found to cause LTM impairment. For instance, Korzus et al. demonstrated that inducible dominant-negative CBP mice, with no CBP HAT activity, exhibited normal short-tem memory while LTM was impaired (*Neuron*, 2004. 42(6): p. 961-72; herein incorporated by reference in its entirety). Moreover, the impaired LTM was rescued by suppression of the transgene expression and by HDAC inhibitor administration (*Neuron*, 2004. 42(6): p. 961-72; herein incorporated by reference in its entirety).

The relevance of histone deacetylation in memory processes is underscored by a study from Levenson et al. (*J Biol Chem*, 2004. 279(39): p. 40545-59; herein incorporated by reference in its entirety). In this work acetylation of H3 in area CA1 of the hippocampus (an area in the brain that plays important roles in LTM) was found to be increased following training for contextual fear conditioning, a form of associative memory in which mice associate a new context with an aversive stimulus. However, HDAC inhibition enhanced LTM (*J Biol Chem*, 2004. 279(39): p. 40545-59; herein incorporated by reference in its entiretyHDAC inhibition can be beneficial in certain neurodegenerative disorders, such as Huntington's disease, spinal muscular atrophy, amyotrophic lateral sclerosis, ischemia and Rubinstein-Taybi syndrome (*Nature*, 2007. 447(7141): p. 178-82; *Neuron*, 2004. 42(6): p. 947-59; *Curr Drug Targets CNS Neurol Disord*, 2005. 4(1): p. 41-50; *Proc Natl Acad Sci USA*, 2003. 100(4): p. 2041-6; each herein incorporated by reference in its entirety). The effect of HDAC inhibitors can depend upon specific HDACs, as neuron-specific overexpression of HDAC2, but not that of HDAC1, reduced dendritic spine density, synapse number, synaptic plasticity and memory formation (*Nature*, 2009. 459(7243): p. 55-60; herein incorporated by reference in its entirety). Conversely, HDAC2 deficiency increased synapse number and facilitated memory, similar to chronic treatment with HDAC inhibitors in mice (*Nature*, 2009. 459(7243): p. 55-60; herein incorporated by reference in its entirety). HDAC inhibition can provide a therapeutic avenue for memory impairment in neurodegenerative diseases characterized by cognitive disorders such as AD.

Recent studies have linked CREB/CBP dysfunction to AD. APP(K670N:M671L) transgenic animals showed a decrease in CREB phosphorylation at the downstream level of the α-7-nicotinic-receptor (α7-nAChR)/ERK/MAPK cascade (*J Neurosci*, 2001. 21(12): p. 4125-33; *J Biol Chem*, 2002. 277(25): p. 22768-80; each herein incorporated by reference in its entirety). Perfusion of hippocampal slices with a preparation containing oligomeric $A\beta_{42}$ revealed a reduction of the tetanus-induced increase in CREB phosphorylation, providing a clue to the mechanisms underlying the Aβ-mediated changes in LTP (*J Neurosci*, 2005. 25(29): p. 6887-97; herein incorporated by reference in its entirety). Consistent with these results, Aβ blocked the glutamate-induced increase in CREB phosphorylation in rat hippocampal cultures (*Proc Natl Acad Sci USA*, 2002. 99(20): p. 13217-21; herein incorporated by reference in its entirety). Gong et al. also found that rolipram, a selective PDE IV inhibitor which increases cAMP levels and therefore CREB phosphorylation, ameliorates deficits in both LTP and contextual learning in the APP/PS1 double-transgenic mouse (*J Clin Invest*, 2004. 114(11): p. 1624-34; herein incorporated by reference in its entirety). Without being bound by theory, this protective effect is due to CREB activation that can lead to CBP recruitment and thus histone acetylation. Another investigation demonstrated that PS1 and 2 conditional double knockout (PS cDKO) mice showed impaired memory and LTP that were amplified with age. In addition PS cDKO mice showed a reduction in CBP levels and in CRE-dependent gene expression in the cerebral cortex, which contributed to subsequent neuronal degeneration (*Neuron*, 2004. 42(1): p. 23-36; herein incorporated by reference in its entirety). In addition, a recent study has demonstrated that wild-type (WT) PS1 stimulates the transcriptional ability of CBP and p300, whereas the AD associated mutant of PS1 (M146L) does not have this effect (*Neuroreport*, 2006. 17(9): p. 917-21; *Neurosci Lett*, 2007. 413(2): p. 137-40; each herein incorporated by reference in its entirety). In these experiments, a response to WT PS1 was observed with a construct containing the 721-1679 region of CBP, which contains the CBP acetyltransferase domain (*Neuroreport*, 2006. 17(9): p. 917-21; herein incorporated by reference in its entirety). Moreover, it was shown that CBP loss and histone deacetylation takes place during neuronal death, which was induced by an APP-directed antibody in primary cortical neurons (*Embo J*, 2003. 22(24): p. 6537-49; herein incorporated by reference in its entirety).

An emerging view of the processes involved in memory impairment indicates that the subtlety and variability of the earliest amnesic symptoms, occurring in the absence of any other clinical signs of brain injury, could be due to discrete changes in the function of a single synapse, produced at least in part, by Aβ (*Proc Natl Acad Sci USA*, 2002. 99(20): p. 13217-21; *Neuroreport*, 1997. 8(15): p. 3213-7; *Eur J Pharmacol*, 1999. 382(3): p. 167-75; *Nature*, 2002. 416 (6880): p. 535-9; each herein incorporated by reference in its entirety).

Several evidences have indicate that LTM and synaptic plasticity rely on gene expression after an early induction phase characterized by the activation of a number of pathways (*Philos Trans R Soc Lond B Biol Sci*, 2003. 358(1432): p. 757-63; herein incorporated by reference in its entirety). More recently, a fine regulation of memory-related genes and long-term synaptic plasticity has been discovered to involve epigenetic factors (*Nat Rev Neurosci*, 2005. 6(2): p. 108-18; herein incorporated by reference in its entirety). Indeed, epigenetic modifications, such as DNA methylation and histone post-translational modifications profoundly affect the ability of polymerases to interact with the open reading frame of DNA without changing the DNA sequence itself. Deregulation of epigenetic mechanisms can lead to the disruption of memory-associated gene expression and synaptic plasticity (*Nat Rev Neurosci*, 2005. 6(2): p. 108-18; herein incorporated by reference in its entirety), and contribute to the pathogenesis of diseases characterized by cognitive disorders, such as AD.

The process of memory storage has been described as a dialogue between genes and synapses (*Biosci Rep*, 2001.

21(5): p. 565-611; herein incorporated by reference in its entirety). The formation of long-term memory (LTM) is dependent upon gene transcription (*Nature*, 1990. 345 (6277): p. 718-21; herein incorporated by reference in its entirety), synthesis of new proteins (*Science*, 1986. 234 (4781): p. 1249-54; herein incorporated by reference in its entirety) and structural changes of the synapse (*Science*, 1983. 220(4592): p. 91-3; herein incorporated by reference in its entirety). In addition, the proper regulation of gene expression in LTM is modulated by epigenetics (*Nat Rev Neurosci*, 2005. 6(2): p. 108-18; herein incorporated by reference in its entirety). The N-terminal tails of histone proteins are known to undergo post-translational modifications, such as histone acetylation, ubiquitination, sumoylation, phosphorylation, citrullination, ADP-ribosylation, and methylation that can dictate the transitions between transcriptionally active or transcriptionally silent chromatin states (*Curr Biol*, 2004. 14(14): p. R546-5; herein incorporated by reference in its entirety). Deregulation of one of these mechanisms can lead to disruption of memory associated gene expression and cognitive disorders. Studies of the mechanisms underlying synaptic and memory dysfunction in AD have indicated central roles for the transcription factor CREB (CRE binding protein) and the coactivator CREB binding protein (CBP).

Alzheimer's disease (AD) is characterized by neuronal loss, extracellular senile plaques and intracellular neurofibrillary tangles, leading to memory loss. AD purportedly begins as a synaptic disorder produced at least in part, by Aβ (*Science* 298, 789-791 (2002); herein incorporated by reference in its entirety). Aβ-induced reduction in long-term-potentiation (LTP), a physiological correlate of synaptic plasticity that is thought to underlie learning and memory, and phosphorylation of the memory transcription factor CREB, are ameliorated by nitric oxide (NO) donors and cGMP-analogs (*J Neurosci* 25, 6887-6897 (2005); herein incorporated by reference in its entirety). Vice-versa, genetic ablation of NO-synthase 2 (NOS2) results in worsening of the AD phenotype in mice expressing mutated amyloid precursor protein (APP) (*Proceedings of the National Academy of Sciences* 103, 12867-12872 (2006); herein incorporated by reference in its entirety). These findings show that up-regulation of the NO pathway may be protective in AD.

Alzheimer's disease (AD) is a chronic progressive neurodegenerative disorder, in which the earliest stages are thought to be linked to synaptic dysfunction leading to memory disorders. In this regard, β-amyloid (Aβ) has been found to inhibit memory (*Proc Natl Acad Sci USA*, 2006. 103:8852-7; *Nat Neurosci*, 2005. 8:79 84; each herein incorporated by reference in its entirety) and its cellular model, long-term potentiation (LTP) (*Neuroreport*, 1997. 8:3213-7; *Eur J Pharmacol*, 1999. 382:167-75; *Proc Natl Acad Sci USA*, 2002. 99:13217-21; *Nature*, 2002. 416:535-9; *J Neurosci Res*, 2000. 60:65-72; *Proc Natl Acad Sci USA*, 1998. 95:6448-53; each herein incorporated by reference in its entirety). Aβ is the proteolytic product of a larger precursor protein, the amyloid precursor protein (APP), which in its mutant form has been found to be implicated in familial AD (FAD) (*Nature*, 1987. 325:733-6; herein incorporated by reference in its entirety). Subsequently, two AD associated genes, presenilin 1 (PS1) and presenilin 2 (PS2) (*Nature*, 1995. 375:754-60; *Science*, 1995. 269:970-3; each herein incorporated by reference in its entirety) were found to be involved in FAD as well (*Prog Neurobiol*, 2000. 60:363-84; herein incorporated by reference in its entirety). Presenilins are part of the γ-secretase complex responsible for cleaving APP and producing the Aβ42 peptide (*Neurosci Lett*, 1999. 260:121-4; herein incorporated by reference in its entirety).

AD is characterized neuropathologically by neuronal loss, extracellular senile plaques (SPs) and intracellular neurofibrillary tangles (NFTs). SPs are chiefly comprised of Aβ aggregates. The major component of NFTs is the microtubule binding protein tau. Clinically, AD is characterized by cognitive dysfunction and begins as a synaptic disorder that involves progressively larger areas of the brain over time (*Histol Histopathol*, 1995. 10(2): p. 509-19; herein incorporated by reference in its entirety). An emerging view of the processes involved in synaptic impairment shows that the subtlety and variability of the earliest amnesic symptoms, occurring in the absence of any other clinical signs of brain injury, can be due to discrete changes in the function of a single synapse, produced at least in part, by Aβ (*Neuroreport*, 1997. 8(15): p. 3213-7; *Eur J Pharmacol*, 1999. 382(3): p. 167-75; *Proc Natl Acad Sci USA*, 2002. 99(20): p. 13217-21; *Nature*, 2002. 416(6880): p. 535-9; herein incorporated by reference in its entirety).

A target for developing a causal therapy for Alzheimer's disease is represented by synapses. Synaptic alterations are highly correlated with the severity of clinical dementia (*Histol Histopathol*, 1995. 10(2): p. 509-19; *Science*, 2002. 298(5594): p. 789-91; each herein incorporated by reference in its entirety), whereas other important variables such as senile plaques and neurofibrillary tangles are involved to a lesser extent (*Histol Histopathol*, 1995. 10(2): p. 509-19; herein incorporated by reference in its entirety). The importance of synaptic alterations in AD has been confirmed by studies of transgenic (Tg) mouse models of AD (*Neurochem Res*, 2003. 28(7): p. 1009-15; herein incorporated by reference in its entirety), as well as of long-term potentiation (LTP), a widely studied cellular model of learning and memory (L&M) (*Nature*, 2002. 416(6880): p. 535-9; herein incorporated by reference in its entirety), which is impaired following application of amyloid-β (Aβ) both in slices and in vivo (*Neurochem Res*, 2003. 28(7): p. 1009-15; *Neuroreport*, 1997. 8(15): p. 3213-7; *J Neurophysiol*, 2001. 85(2): p. 708-13; *Eur J Pharmacol*, 1999. 382(3): p. 167-75; *J Neurosci*, 2001. 21(4): p. 1327-33; *J Neurosci*, 2001. 21(15): p. 5703-14; *Proc Natl Acad Sci USA*, 2002. 99(20): p. 13217-21; *Nature*, 2002. 416(6880): p. 535-9; *J Neurosci*, 2005. 25(29): p. 6887-97; each herein incorporated by reference in its entirety). Aβ has been found to markedly inhibit LTP. Electrophysiological studies using Tg, human Aβ producing mice have often revealed significant deficits in basal synaptic transmission and/or LTP in the hippocampus (*Ann Neurol*, 2004. 55(6): p. 801-14; *Nat Neurosci*, 1999. 2(3): p. 271-6; *J Neurosci*, 2001. 21(13): p. 4691-8; *Proc Natl Acad Sci USA*, 1999. 96(6): p. 3228-33; *Neurobiol Dis*, 2002. 11(3): p. 394-409; *Brain Res*, 1999. 840(1-2): p. 23-35; *J Biol Chem*, 1999. 274(10): p. 6483-92; *Nature*, 1997. 387(6632): p. 500-5; each herein incorporated by reference in its entirety).

Recent studies have linked the transcriptional machinery to Alzheimer's disease (AD), a pathology characterized by profound memory disorders. Both the transcription factor CREB (CRE binding protein) and the coactivator CREB binding protein (CBP), two molecules that are known to be associated with chromatin and memory processes (*Neuron*, 2004. 42(6): p. 961-72; *Cell*, 1994. 79(1): p. 59-68; *Cell*, 1994. 79(1): p. 49-58; each herein incorporated by reference in its entirety), play central roles in the mechanisms underlying synaptic and memory dysfunction in AD. Drugs enhancing CREB phosphorylation were shown to ameliorate memory and long-term potentiation (LTP), a type of synaptic plasticity that is thought to underlie learning and memory, both in mouse models of AD and following exposure to sublethal doses of Aβ42, a proteolytic product of the amyloid precursor protein (APP) (*Proc Natl Acad Sci USA*, 2002. 99(20): p. 13217-21; *J Neurosci*, 2005. 25(29): p. 6887-97; Puzzo, D., A. et al, *Sildenafil rescues synaptic and cognitive impairment in a mouse model of Alzheimer's disease*. in *Soc Neurosci. Abstr.* 2006. Atlanta; *J. Clin. Invest.*, 2004. 114: p. 1624-1634; each herein incorporated by reference in its entirety). Following exposure to sublethal doses of A$\beta_{42}$ and in mouse models of AD, drugs enhancing CREB phosphorylation were shown to ameliorate LTP and memory (*Proc Natl Acad Sci USA*, 2002. 99:13217-21; *J Neurosci*, 2005. 25:6887-97; Puzzo et al, in *Soc Neurosci. Abstr.* 2006. Atlanta; *J. Clin. Invest.*, 2004. 114:1624-1634; each herein incorporated by reference in its entirety). Dysregulation of CBP histone acetyltransferase (HAT) activity disrupts memory associated gene expression (*Neuron*, 2004. 42:961-72; herein incorporated by reference in its entirety). In addition, cerebral CBP levels are reduced in mice lacking functional presenilin 1 (PS1) and presenilin 2 (PS2) (*Neuron*, 2004. 42(1): p. 23-36; each herein incorporated by reference in its entirety), two genes that have been implicated in AD (*Nature*, 1995. 375(6534): p. 754-60; *Science*, 1995. 269(5226): p. 970-3; each herein incorporated by reference in its entirety). Moreover, wild-type (WT) PS1 stimulates CBP transcriptional ability, whereas PS1(M146L) mutation does not have this effect (*Neuroreport*, 2006. 17(9): p. 917-21; herein incorporated by reference in its entirety).

NO is a central molecule in cellular biochemical processes. This gas has been established as an important messenger molecule in various steps of brain physiology, from development to synaptic plasticity and learning and memory. In AD research, NO has been found to have a protective effect on Aβ-induced damage of the nervous system (*Med Hypotheses*, 1998. 51(6): p. 465-76; *J Neurosci*, 2000. 20(4): p. 1386-92; *Neuroscience*, 2000. 99(4): p. 737-50; each herein incorporated by reference in its entirety). Studies performed on PC12 cells, sympathetic neurons and hippocampal neurons, have shown that treatment with the NO generator S-nitroso penicillamine exerts a neuroprotective effect due to the inhibition of the pro-apoptotic factor caspase-2 by nitrosylation (*J Neurosci*, 2000. 20(4): p. 1386-92; herein incorporated by reference in its entirety), whereas inhibition of NO synthesis by N-nitro-L-arginine methyl ester does not protect against Aβ-induced neurotoxicity. Aβ has been found to impair NO generation by decreasing NMDA receptor signal transduction (*Med Hypotheses*, 1998. 51(6): p. 465-76; herein incorporated by reference in its entirety), by subtracting NADPH availability to NO-synthase (NOS) (*Faseb J*, 2002. 16(14): p. 1970-2; herein incorporated by reference in its entirety), or by inhibiting the phosphorylation of the serine-threonine kinase Akt (*Neurobiol Aging*, 2003. 24(3): p. 437-51; herein incorporated by reference in its entirety). Moreover, i-NOS deletion enhances AD pathology in the APP mice (*Proc Natl Acad Sci USA*, 2006. 103(34): p. 12867-72; herein incorporated by reference in its entirety). Thus, drugs enhancing the NO-cascade can have a beneficial effect against AD (*Curr Alzheimer Res*, 2005. 2(2): p. 171-82; herein incorporated by reference in its entirety).

Despite the neuroprotective function of NO, it has also been viewed as a major agent of neuropathology and cell death when it is produced in high quantities. High amounts of NO lead to generation of significant quantity of peroxinitrites that are responsible for oxidative and nitrosative stress in Aβ-induced cell death (*Neurosci Lett*, 2002. 322(2): p. 121-5; *Faseb J*, 2001. 15(8): p. 1407-9; *Exp Gerontol*, 1997. 32(4-5): p. 431-40; *J Neurosci*, 2002. 22(9): p. 3484-92; *Brain Res*, 2001. 920(1-2): p. 32-40; *J Neurosci*, 2004. 24(27): p. 6049-56; *J Immunol*, 2003. 171(5): p. 2216-24; each herein incorporated by reference in its entirety). In fact, release of low amounts of NO by the constitutive forms of NOS that include both the neuronal and the endothelial isoforms, n-NOS and e-NOS, promotes synaptic plasticity and learning, whereas uncontrolled production of high amounts of the gas by the inducible form of NOS (i-NOS) can promote oxidative and nitrosative stress via production of peroxinitrite (*Neurosci Lett*, 2002. 322(2): p. 121-5; *Faseb J*, 2001. 15(8): p. 1407-9; *Exp Gerontol*, 1997. 32(4-5): p. 431-40; *J Neurosci*, 2002. 22(9): p. 3484-92; *Brain Res*, 2001. 920(1-2): p. 32-40; *J Neurosci*, 2004. 24(27): p. 6049-56; *J Immunol*, 2003. 171(5): p. 2216-24; each herein incorporated by reference in its entirety). Both Aβ-induced downregulation of the NO cascade which blocks plasticity and memory and generation of peroxinitrites leading to cell death, can play roles in AD. The current status of drug research exploiting these discoveries is focused both on finding ways to upregulate the NO cascade and therefore elicit neuroprotection, as well as on finding ways to block peroxinitrite toxic effects in order to limit neuropathology (*Curr Med Chem*, 2003. 10(20): p. 2147-74; herein incorporated by reference in its entirety).

In some embodiments, the compounds of the invention are HAT modulators. The term "modulate", as it appears herein, refers to a change in the activity or expression of a protein molecule. For example, modulation can cause an increase or a decrease in protein activity, binding characteristics, or any other biological, functional, or immunological properties of a secretase protein molecule. In some embodiments, the compounds activate HAT. In some embodiments, the compounds inhibit HAT.

A HAT modulator compound can be a compound that increases the activity and/or expression of a HAT molecule (e.g., GCN5, GCN5L, PCAF, or HAT1) in vivo and/or in vitro. HAT modulator compounds can be compounds that exert their effect on the activity of a HAT protein via the expression, via post-translational modifications, or by other means. In some embodiments, a HAT modulator compound increases HAT protein or mRNA expression, or acetyltransferase activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

Test compounds or agents that bind to a HAT molecule (such as GCN5, GCN5L, PCAF, or HAT1), and/or have a stimulatory effect on the activity or the expression of a HAT molecule, can be identified by various assays. The assay can be a binding assay comprising direct or indirect measurement of the binding of a test compound or a known HAT ligand to the active site of a HAT protein. The assay can also be an activity assay comprising direct or indirect measurement of the activity of a HAT molecule. The assay can also be an expression assay comprising direct or indirect measurement of the expression of a HAT mRNA or protein. The various screening assays can be combined with an in vivo assay comprising measuring the effect of the test compound on cognitive and synaptic function in an animal model for neurodegenerative disorders, such as, but not limited to, AD or Huntington's Disease.

The inhibitors of the expression of a HAT molecule can be identified via contacting a HAT-positive cell or tissue with a test compound and determining the expression of a HAT protein or HAT mRNA in the cell. The protein or mRNA expression level of a HAT molecule in the presence of the test compound can be compared to the protein or mRNA expression level of a HAT protein in the absence of the test compound. The test compound can then be identified as an inhibitor of expression of a HAT protein (such as GCN5, GCN5L, PCAF, or HAT1) based on this comparison. In other words, the test compound can also be a HAT inhibitor compound (such as an antagonist).

Acivators of the expression of a HAT molecule can also be identified via contacting a HAT-positive cell or tissue with a test compound and determining the expression of a HAT protein or HAT mRNA in the cell. The protein or mRNA expression level of a HAT molecule in the presence of the test compound can be compared to the protein or mRNA expression level of a HAT protein in the absence of the test compound. The test compound can then be identified as an activator of expression of a HAT protein (such as GCN5, GCN5L, PCAF, or HAT1) based on this comparison. For example, when expression of HAT protein or mRNA is statistically or significantly more in the presence of the test compound than in its absence, the compound is identified as an activator of the expression of a HAT protein or mRNA. In other words, the test compound can also be a HAT Activator compound (such as an agonist). The expression level of a HAT protein or mRNA in cells can be determined by methods described herein.

Determining the ability of a test compound to bind to a HAT molecule or a variant thereof can be accomplished using real-time Bimolecular Interaction Analysis (BIA) [McConnell, (1992); Sjolander, (1991)]. BIA is a technology for studying biospecific interactions in real time, without labeling any of the interactants (e.g., BIA-Core™). Changes in optical phenomenon surface plasmon resonance (SPR) can be used as an indication of real-time reactions between biological molecules.

In some embodiments, the invention provides for compounds that bind to a HAT activator protein, such as GCN5, GCN5L, PCAF, or HAT1. These compounds can be identified by the screening methods and assays described herein, and enhance the activity or expression of HAT activator proteins.

In some embodiments, the compound of formula (I) is 8, 9, 10, 11, 12, 13, and/or 14.

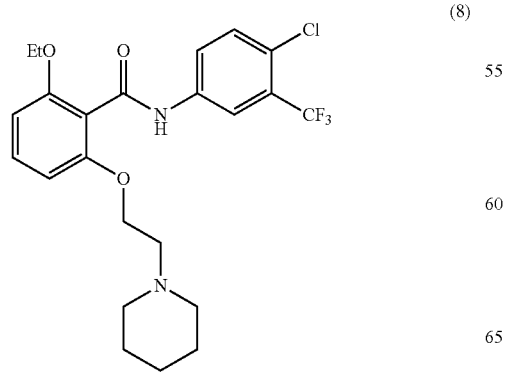

(8)

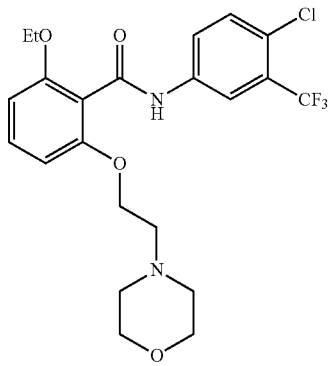

(9)

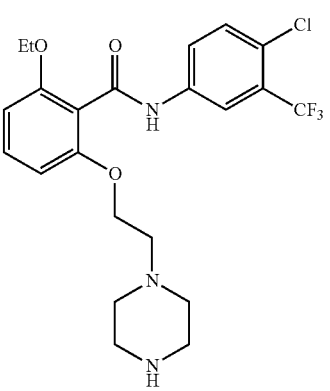

(10)

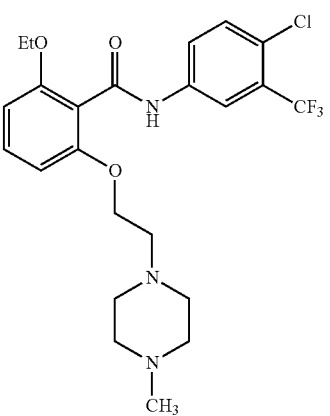

(11)

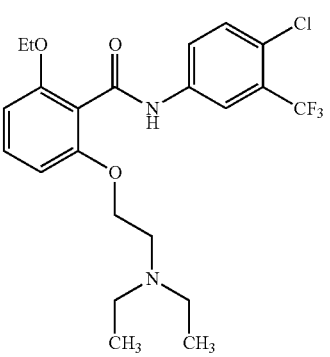

(12)

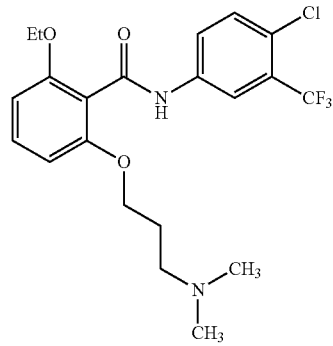
(13)
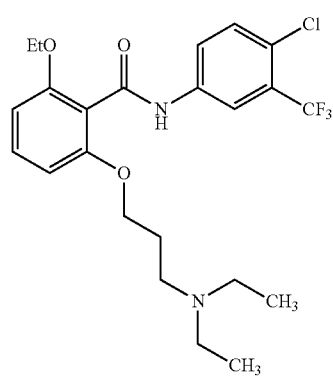
(14)
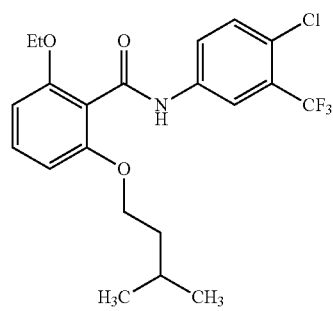
(15)
In some embodiments, the compound of formula (I) is 16 and/or 17.
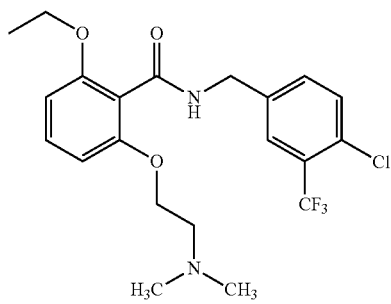
(16)
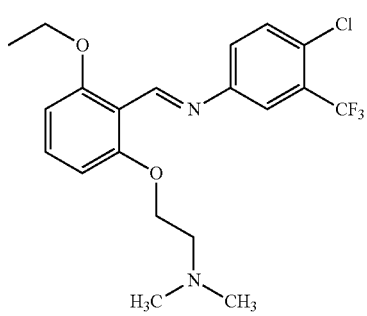
(17)
In some embodiments, the compound of formula (I) is 18, 19, 20, and/or 21.
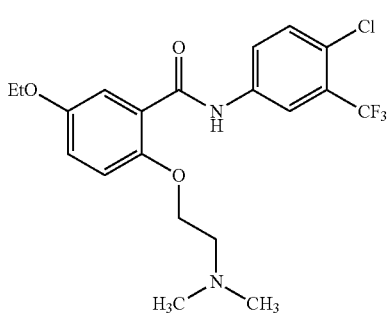
(18)
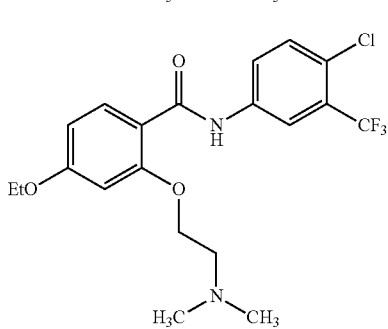
(19)
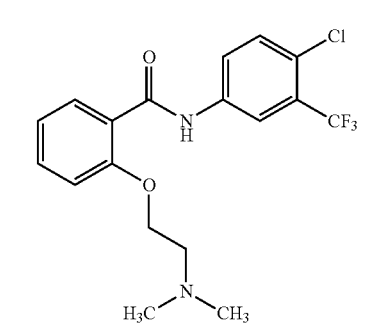
(20)
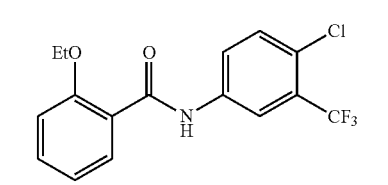
(21)
In some embodiments, the compound of formula (I) is 22, 23, and/or 24.

(22)

(23)

(24)

In some embodiments, the compound of formula (I) is 25 and/or 26.

(25)

(26)

In some embodiments, $R^a$ is H, halogen, or haloalkyl;
Y is CH, C-halogen, or C—CN;
$R^b$ is H, O—($C_1$-$C_2$-alkyl), S—($C_1$-$C_2$-alkyl), O-cyclopentyl, $OCH_2CH_2N(CH_3)_2$, or $CH_2CH_2CH_2N(CH_3)_2$;
$R^c$ is H; C(=O)NH-phenyl, wherein phenyl is substituted with one or more halo or haloalkyl;
$R^d$ is H, $C_1$-$C_5$-alkyl, OH, O-alkyl, $OCH_2CH_2N(CH_3)_2$, $CH_2CH_2CH_2N(CH_3)_2$,
$SCH_2CH_2N(CH_3)_2$, or $OCH_2C(=O)O$-alkyl;
Z is CH, C—O—($C_1$-$C_2$-alkyl), C—$OCH_2CH_2N(CH_3)_2$; and
X is CONH, SONH, $SO_2NH$, NHC(=O)NH, or NHCO, or a pharmaceutically acceptable salt or hydrate thereof.

Figure 5:
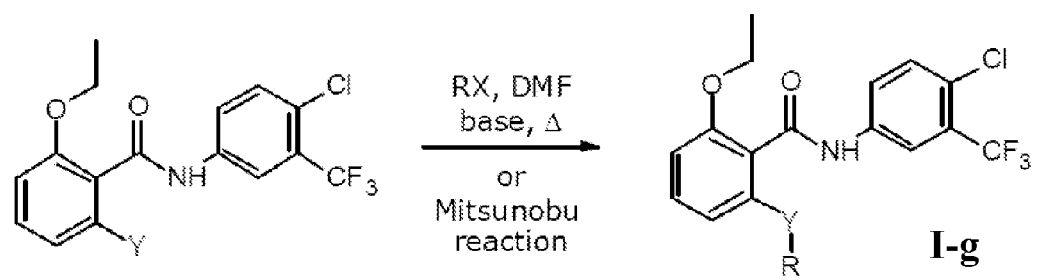
FIG. 5 is an exemplary synthetic scheme for compounds (I-g). Modifications at C2, where Y is OH, or $NH_2$. Modifications at C2 for compounds (I-g), where Y is O, or NH; R is alkyl, cycloalkyl, alkenyl, heterocycle, aryl, heteroaryl, alkylamino, or cycloalkylamino.

In some embodiments, the compound of formula (I) is compound (I-g):

(I-g)

wherein $R^d$ is —O—($C_1$-$C_6$)-alkyl, —NH—($C_1$-$C_6$)-alkyl, —O—($C_2$-$C_6$)-alkenyl, —NH—($C_2$-$C_6$)-alkenyl, —O—($C_3$-$C_8$)-cycloalkyl, —NH—($C_3$-$C_8$)-cycloalkyl, —O—($C_3$-$C_8$)-heterocycloalkyl, —NH—($C_3$-$C_8$)-heterocycloalkyl, —O-aryl, —N-aryl, —O-heteroaryl, —N-heteroaryl, —O—($C_1$-$C_6$)-alkyl-N($R^{10}$)$_2$, —NH—($C_1$-$C_6$)-alkyl-N($R^{10}$)$_2$, —O—($C_1$-$C_6$)-alkyl-$R^3$, or —NH—($C_1$-$C_6$)-alkyl)-$R^3$. Compounds (I-g) can be synthesized according to the scheme depicted in FIG. 5.

In some embodiments, the compound of formula (I) is compound (I-h):

(I-h)

wherein $R^b$ is —O—($C_1$-$C_6$)-alkyl, —O—($C_2$-$C_6$)-alkenyl, —O—($C_3$-$C_8$)-cycloalkyl, —O—($C_3$-$C_8$)-heterocycloalkyl, —O-aryl, —O-heteroaryl, —O—($C_1$-$C_6$)-alkyl-N($R^{10}$)$_2$, or —O—($C_1$-$C_6$)-alkyl)-$R^3$. Compounds (I-h) can be synthesized according to the scheme depicted in FIG. 6.

In some embodiments, the compound of formula (I) is compound (I-i):

(I-i)

wherein $R^{10}$ is H, —($C_1$-$C_4$-alkyl), —($C_1$-$C_4$-haloalkyl), —($C_3$-$C_8$-cycloalkyl), —($C_3$-$C_8$-heterocycloalkyl), aryl or heteroaryl, wherein aryl or heteroaryl.

In some embodiments, the compound of formula (I) is

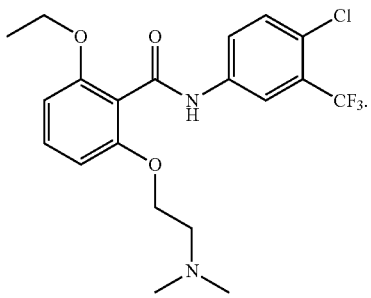 [SMILES: CCOc1cccc(OCCN(C)C)c1C(=O)Nc1ccc(Cl)c(C(F)(F)F)c1]

In some embodiments, the compound of formula (I) is

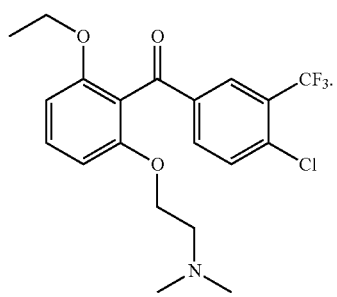 [SMILES: CCOc1cccc(OCCN(C)C)c1C(=O)c1ccc(Cl)c(C(F)(F)F)c1]

In some embodiments, the compound of formula (I) is

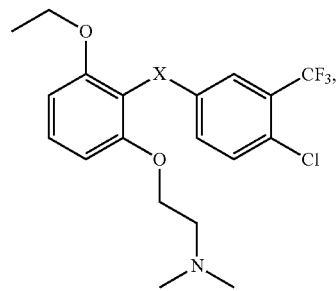

(I-j)

wherein X is CH₂CONH(CH₂)ₙ, and n is 0-3.

In some embodiments, the compound of formula (I) is

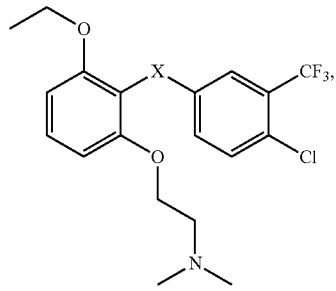

(I-k)

wherein X is CONH(CH₂)ₙ, and n is 0-3.

In some embodiments, the compound of formula (I) is

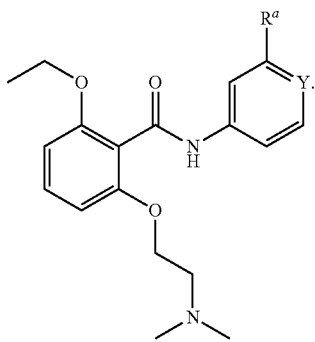

(I-l)

In some embodiments, the compound of formula (I) is

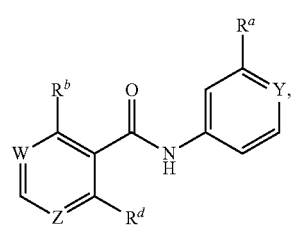

(I-a)

wherein, $R^a$ is H, halogen, or haloalkyl; $R^b$ is O—($C_1$-$C_6$)-alkyl or S—($C_1$-$C_6$)-alkyl; $R^d$ is ($C_1$-$C_6$)-alkyl or O—($C_1$-$C_6$)-alkyl-N(CH$_3$)$_2$; Y is haloalkyl, C—CN, C—NO$_2$, or N; W is CH or N; and Z is CH or N, or a pharmaceutically acceptable salt or hydrate thereof.

In some embodiments, the compound of formula (I) is

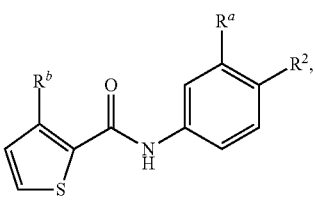

(I-b)

wherein $R^a$ is haloalkyl; $R^2$ is CN; and $R^b$ is O—($C_1$-$C_6$)-alkyl, or a pharmaceutically acceptable salt or hydrate thereof.

In some embodiments, the compound of formula (I) is

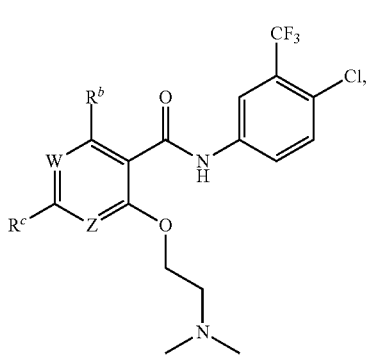

(I-c)

wherein $R^b$ is H, or ethoxyl; W and Z are independently CH, C—Cl, or C—OEt; and $R^c$ is H, ethoxyl, or methyl; or a pharmaceutically acceptable salt or hydrate thereof.

In some embodiments of formula (I-c), $R^b$ is ethoxyl, W and Z are each CH, and $R^c$ is methyl. In some embodiments of formula (I-c), $R^b$ is ethoxyl, W and Z are each C—Cl, and $R^c$ is H. In other embodiments of formula (I-c), $R^b$ is H, W is ethoxyl, $R^c$ is H, and Z is CH. In a further embodiment of formula (I-c), $R^b$ is H, W and Z are each CH, and $R^c$ is ethoxyl.

In some embodiments, the compound of formula (I) is

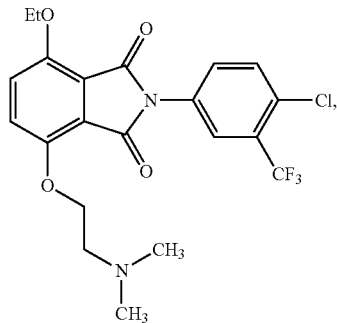 [SMILES: CCOc1ccc(OCCN(C)C)c2c1C(=O)N(c1ccc(Cl)c(C(F)(F)F)c1)C2=O]

or a pharmaceutically acceptable salt or hydrate thereof. Compound 5 can be synthesized according to the scheme depicted in FIG. 11.

In some embodiments, the compound of formula (I) is

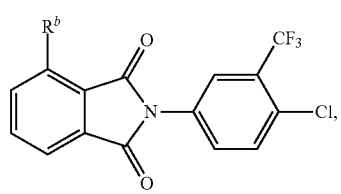

(I-d)

wherein $R^b$ is —O-ethyl, —O—CH$_2$CH$_2$N(CH$_3$)$_2$, —NH-ethyl, or —NH—CH$_2$CH$_2$N(CH$_3$)$_2$, or a pharmaceutically acceptable salt or hydrate thereof. Compounds (I-d) can be synthesized according to the scheme depicted in FIG. 12.

In some embodiments, the compound of formula (I) is

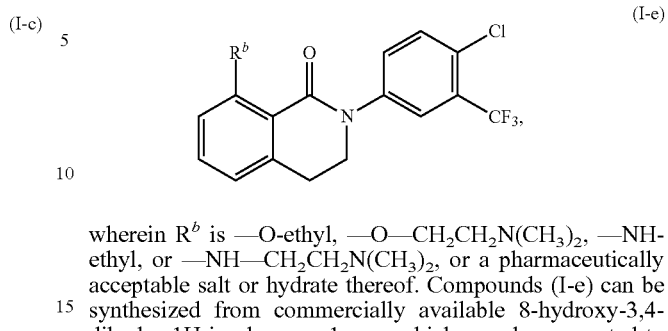

(I-e)

wherein $R^b$ is —O-ethyl, —O—CH$_2$CH$_2$N(CH$_3$)$_2$, —NH-ethyl, or —NH—CH$_2$CH$_2$N(CH$_3$)$_2$, or a pharmaceutically acceptable salt or hydrate thereof. Compounds (I-e) can be synthesized from commercially available 8-hydroxy-3,4-dihydro-1H-isochromen-1-one, which may be converted to the N-substituted 8-hydroxy-isochincolone via treatment with the corresponding amine in pyridine at reflux; followed by alkylation of the hydroxyl group.

In some embodiments, the compound of formula (I) is

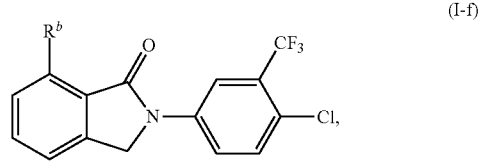

(I-f)

wherein $R^b$ is —O-ethyl, —O—CH$_2$CH$_2$N(CH$_3$)$_2$, —NH-ethyl, or —NH—CH$_2$CH$_2$N(CH$_3$)$_2$, or a pharmaceutically acceptable salt or hydrate thereof. Compounds (I-f) can be synthesized analogous to a published procedure (*Org. Proc. Res. & Dev.* 2009, 13, 1407-1412; hereby incorporated by reference in its entirety).

In some embodiments, the compound of formula (I) is

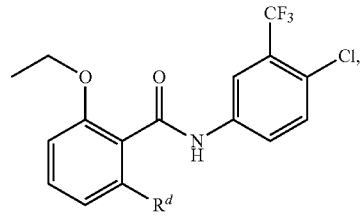

wherein $R^d$ is 2-(piperidin-1-yl) ethyloxy (8); 2-morpholinoethyloxy (9); 2-(piperaz-1-yl)-ethyloxy (10); 2-(4-methylpiperazin-1-yl)-ethyloxy (11); 2-(N,N-diethylamino)ethyloxy (12); 3-(N,N-dimethylamino)propyloxy (13), 3-(N,N-diethylamino)propyloxy (14); 3-methylbutyloxy (15). The compounds 8-15 can be synthesized, for example, via Scheme 1.

Scheme 1[a]

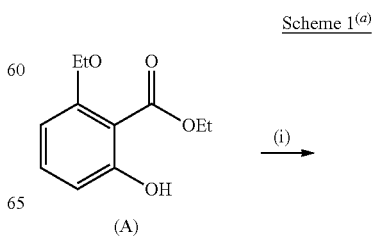

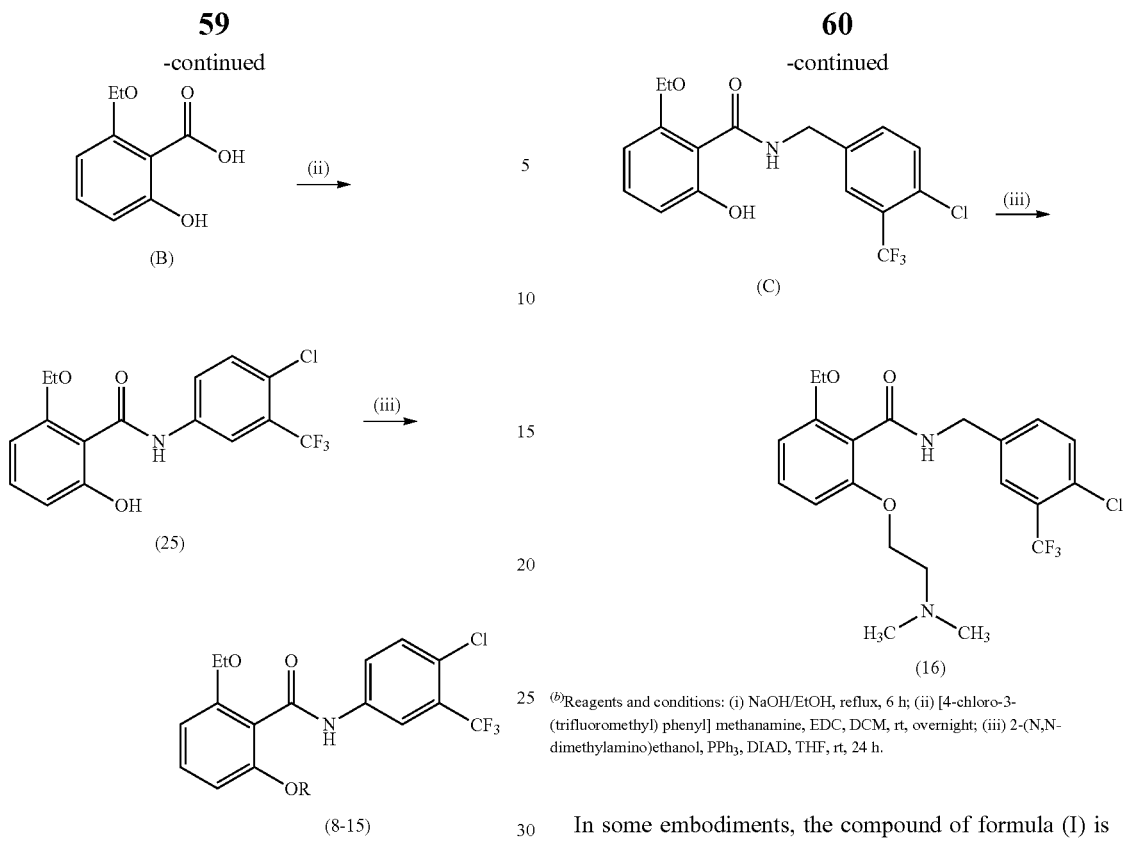

8, R = (2-piperidin-1-yl) ethyl; 9, R = 2-morpholinoethyl; 10, R = 2(piperaz-1-yl) ethyl; 11, R = 2-(4-methylpiperazin-1-yl) ethyl; 12, R = 2-(N,N-diethylamino)ethyl; 13, R = 3-(N,N-dimethylamino)propyl, 14, R = 3-(N,N-diethylamino)propyl; 15, R = 3-methylbutyl. [a]Reagents and conditions: (i) NaOH/EtOH, reflux, 6 h; (ii) [4-chloro-3-(trifluoromethyl) phenyl] methanamine, EDC, DCM, rt, overnight; (iii) ROH, PPh₃, DIAD, THF, rt, 24 h or RX, K₂CO₃, DMF, 80° C., 24 h (X = Halogen).

[b]Reagents and conditions: (i) NaOH/EtOH, reflux, 6 h; (ii) [4-chloro-3-(trifluoromethyl) phenyl] methanamine, EDC, DCM, rt, overnight; (iii) 2-(N,N-dimethylamino)ethanol, PPh₃, DIAD, THF, rt, 24 h.

In some embodiments, the compound of formula (I) is

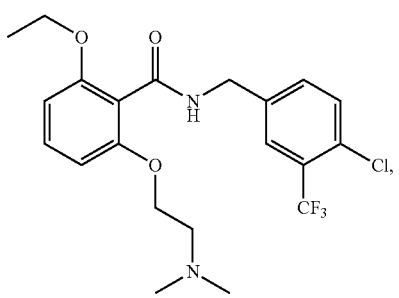 [SMILES: CCOc1cccc(OCCN(C)C)c1C(=O)NCc1ccc(Cl)c(C(F)(F)F)c1]

which can be synthesized, for example, via Scheme 2.

Scheme 2[b]

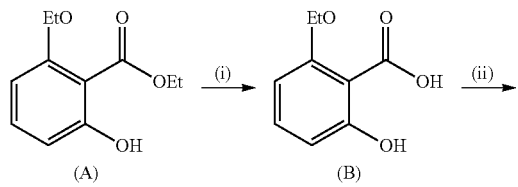

In some embodiments, the compound of formula (I) is

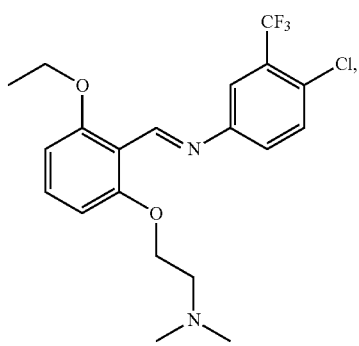 [SMILES: CCOc1cccc(OCCN(C)C)c1/C=N/c1ccc(Cl)c(C(F)(F)F)c1]

which can be synthesized, for example, via Scheme 3.

Scheme 3[c]

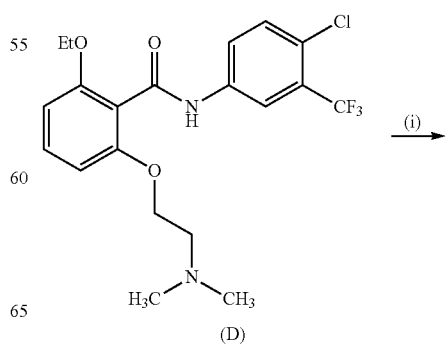

-continued

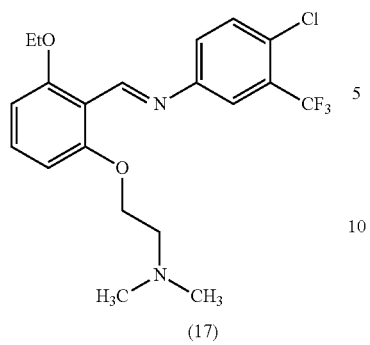

(17)

[c]Reagents and conditions: (i) NaBH₄, BF₃·OEt₂, THF, 60° C., 24 h.

In some embodiments, the compound of formula (I) is

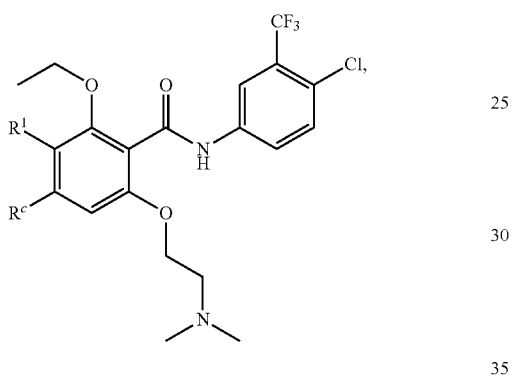

wherein $R^1$ is ethoxyl and $R^c$ is H (18); or $R^1$ is H and $R^c$ is ethoxyl (19). The compounds 18 and 19 can be synthesized, for example, via Scheme 4.

Scheme 4[d]

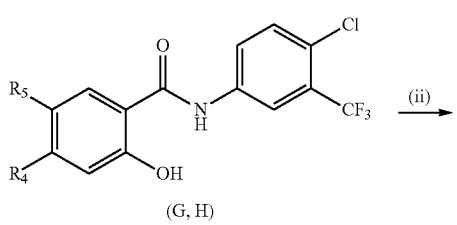

-continued

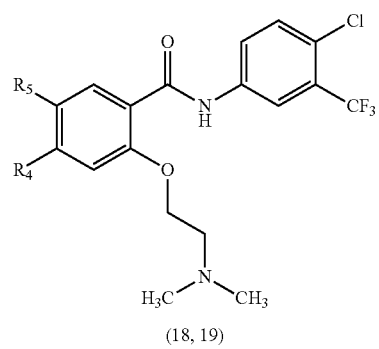

(18, 19)

E, G and 18, $R_5$ = ethoxyl, $R_4$ = H; F, H and 19, $R_5$ = H, $R_4$ = ethoxyl.
[d]Reagents and conditions: (i) 4-chloro-3-(trifluoromethyl) aniline, EDC, DCM, rt, 24 h; (ii) 2-chloro-N,N-dimethylethanamine, K₂CO₃, DMF, 80° C., 24 h.

In some embodiments, the compound of formula (I) is

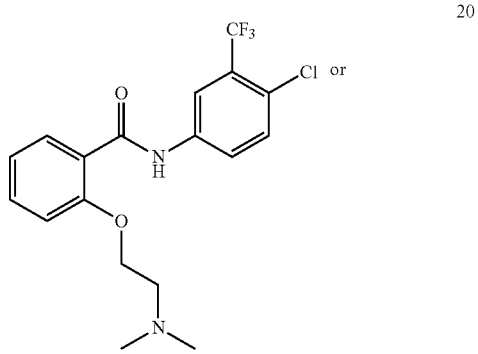

20 or

21

The compounds 20 and 21 can be synthesized, for example, via Scheme 5.

Scheme 5[e]

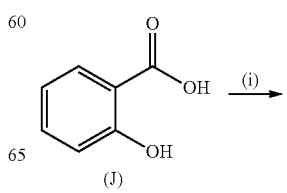

(J)

-continued

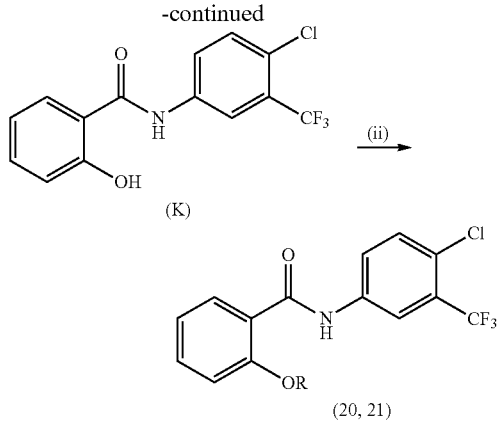

(K)

(20, 21)

20, R = 2-(N,N-dimethylamino)ethyl; 21, R = ethyl.
(e) Reagents and Conditions: (i) SOCl₂, 4-chloro-3-(trifluoromethyl) aniline, DCM, reflux, 16 h; (ii) ROH, PPh₃, DIAD, THF, rt, 24 h or RX, K₂CO₃, DMF, 80° C., 24 h (X = halogen).

In some embodiments, the compound of formula (I) is

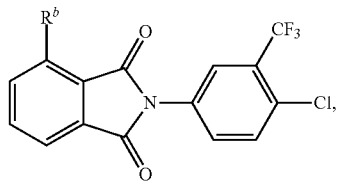

22

The compound 22 can be synthesized, for example, via Scheme 6.

Scheme 6(f)

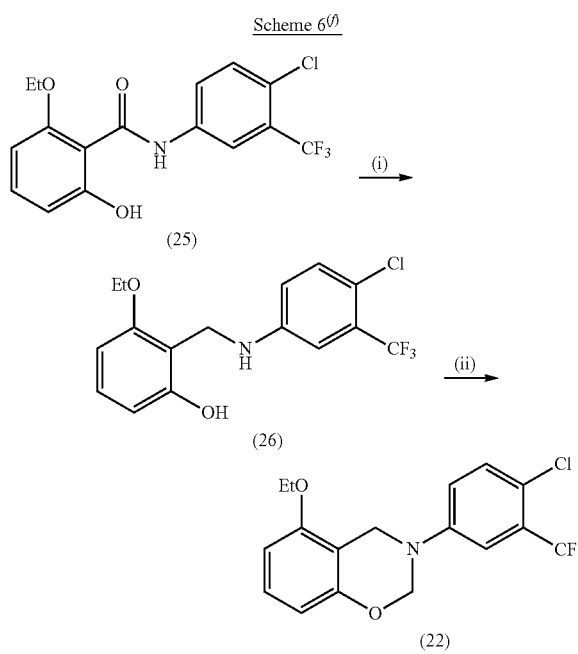

(f) Reagents and Conditions: (i) LAH, THF, reflux, 0.5 h; (ii) Formalin, EtOH, reflux, 2.5 h.

In some embodiments, the compound of formula (I) is

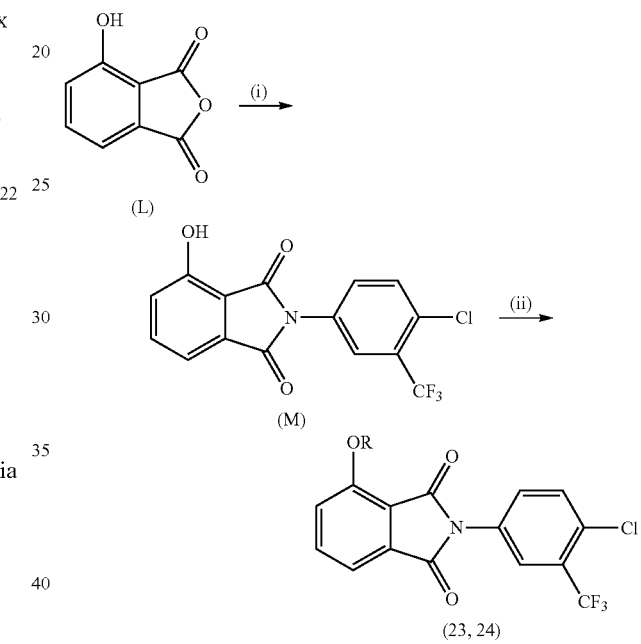

wherein $R^b$ is ethoxy (23), or 2-(N, N-dimethyl)-ethoxy (24). The compounds 23 and 24 can be synthesized, for example, via Scheme 7.

Scheme 7(g)

23, R = ethyl; 24, R = 2-(N,N-dimethylamino)-ethyl.
(g) Reagents and Conditions: (i) 4-chloro-3-(trifluoromethyl) aniline, AcOH, reflux, 2 h; (ii) RX, K₂CO₃, DMF, 80° C., 8 h (For 23, X = halogen and R is ethyl; for 24, RX is 2-chloro-N, N- dimethylethanamine).

Pharmaceutically acceptable salts are known in the art, and can be selected from those listed in Berge, et al. ["Pharmaceutical Salts," *J. Pharm. Sci.,* 66(1):1-19 (January 1977); herein incorporated by reference in its entirety]. In some embodiments, a pharmaceutically acceptable salt of a compound of formula (I) is an acid addition salt, for example a hydrohalide (such as hydrochloride or hydrobromide), sulfate, or phosphate salt. In some embodiments, a pharmaceutically acceptable salt of a compound of formula (I) is a base addition salt, for example a sodium, potassium, calcium, or ammonium salt. In some embodiments, the base addition salt is a tetrafluoroboro salt.

In some embodiments, the invention provides methods for reducing inclusion bodies (e.g., amyloid beta (Aβ) protein deposits, native and phosphorylated Tau proteins, native and phosphorylated alpha-synuclein, lipofuscin, cleaved TAR-DBP (TDB-43), or a combination thereof) in a subject afflicted with a neurodegenerative disease (e.g., a AD, Huntington's Disease, or Parkinson's Disease) by administering any one of the HAT modulator compounds having formula (I). In some embodiments, the invention provides methods for treating a neurodegenerative disease in a subject by administering any one of the HAT modulator compounds having formula (I). In some embodiments, the invention further provides methods for treating cancer in a subject by administering any one of the HAT modulator compounds having formula (I). In some embodiments, the compound administered to a subject is any one of the compounds of formula (I). In some embodiments, the compound administered to a subject is any one of compounds any of compounds 1-26 or any combination thereof.

In some embodiments, the methods comprise administering to the subject an effective amount of a composition comprising a HAT modulator compound. In some embodiments, the subject exhibits abnormally elevated amyloid beta plaques, or elevated Tau protein levels, or accumulations of alpha-synuclein, or accumulations of lipofuscin, or accumulation of cleaved TARDBP (TDB-43) levels, or a combination thereof. In some embodiments, the A$\beta$ protein deposit comprises an A$\beta_{40}$ isomer, an A$\beta_{42}$ isomer, or a combination thereof. In a further embodiment, the subject is afflicted with Alzheimer's disease, Lewy body dementia, inclusion body myositis, Huntington's Disease, Parkinson's Disease, or cerebral amyloid angiopathy. In some embodiments, the subject is afflicted with cancer.

The dosage administered can be a therapeutically effective amount of the composition sufficient to result in amelioration of symptoms of a neurodegenerative disease such as, but not limited to reducing inclusion bodies (e.g., amyloid beta (A$\beta$) protein deposits, native and phosphorylated Tau proteins, native and phosphorylated alpha-synuclein, lipofuscin, cleaved TARDBP (TDB-43), or a combination thereof), or reducing memory loss in a subject. For example, observing at least, about a 25% reduction, at least about a 30% reduction, at least about a 40% reduction, at least about a 50% reduction, at least about a 60% reduction, at least about a 70% reduction, at least about a 80% reduction, at least about a 85% reduction, at least about a 90% reduction, at least about a 95% reduction, at least about a 97% reduction, at least about a 98% reduction, or a 100% reduction in inclusion bodies or memory loss in a subject is indicative of amelioration of symptoms of a neurodegenerative disease (for example, including, but not limited to, AD, Huntington's Disease, Parkinson's Disease). This efficacy in reducing inclusion occurrence, can be, for example, a meaure of ameliorating symptoms of a neurodegenerative disease.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

A HAT modulator compound can be administered to the subject one time (e.g., as a single injection or deposition). Alternatively, a HAT modulator compound of the invention can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can also be used.

A therapeutically effective dose of a HAT modulator compound can depend upon a number of factors known to those of ordinary skill in the art. The dose(s) of a HAT modulator compound, for example a compound of formula (I), can vary, for example, depending upon the identity, size, and condition of the subject or sample being treated, further depending upon the route by which the composition is to be administered, if applicable, and the effect which the practitioner desires the HAT modulator compound to have upon a HAT protein or a protein exhibiting intrinsic HAT activity. These amounts can be readily determined by a skilled artisan.

HAT modulator compounds of the invention can be incorporated into pharmaceutical compositions suitable for administration. Such compositions can comprise a HAT modulator compound (e.g., a compound of formula (I), or any of compounds 1-26 or any combination thereof) and a pharmaceutically acceptable carrier. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a mouse, rat, dog, cat, cow, horse, rabbit, monkey, pig, sheep, goat, or human. In some embodiments, the subject is mouse, rat, monkey, dog or human. In some embodiments, the subject is a mouse, monkey or human. In some embodiments, the subject is a human.

A pharmaceutical composition of the invention can be formulated to be compatible with its intended route of administration. Exemplary routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The injectable composition should be sterile and should be fluid to the extent that easy syringability exists. It should also be stable under the conditions of manufacture and storage and preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many embodiments, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the HAT modulator compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It will recognized that one or more features of any embodiments or aspects disclosed herein can be combined and/or rearranged within the scope of the invention to produce further embodiments that are also within the scope of the invention.

As will be apparent to one of ordinary skill in the art from a reading of this disclosure, the embodiments of the present disclosure can be embodied in forms other than those specifically disclosed above. The particular embodiments described herein are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

A compound, D, that increases histone acetylation was recently discovered (WO 2011/072243; hereby incorporated by reference in its entirety). Compound D (MW 431, c log P 5.15, c log BB 0.17) is soluble, membrane permeable and BBB permeant, and is safe in acute toxicity tests. Compound D is a N-[4-chloro-3-(trifluoromethyl)phenyl]-2-[2-(dimethyl-amino) ethoxy]-6-ethoxybenzamide. Its benzamide ring (I ring) has two substituents at C2 and C6, 2-dimethylamino ethoxy and ethoxy groups, respectively. The nitrogen atom of its amide group bears a substituted phenyl ring (II ring).

Figure 4:
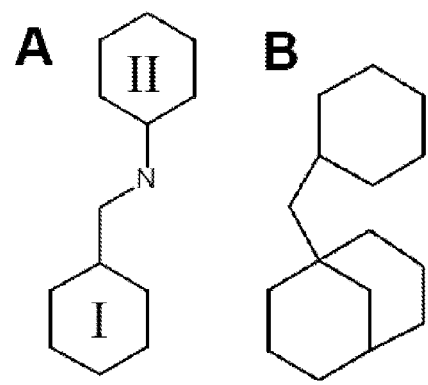
FIG. 4 is a schematic of the compound D/CTPB/CTB (FIG. 4A) and nemorosone (FIG. 4B) scaffolds.

A strategy was employed to assess impact of structure on metabolic stability of D and explore the binding site through SAR analysis, and analysis of DCTPB/CTB and nemorosone. An analysis of D/CTPB/CTB and nemorosone scaffolds shows that the two scaffolds consist of two ring-systems connected by a linker (FIG. 4). In particular, two mono-cyclic rings (I and II ring) linked by a 2-nodes linker form the scaffold of D/CTPB/CTB while in nemorosone's scaffold a bi-cyclic ring is connected with a mono-cyclic ring by a 1-node linker. Derivatives at the level of I ring were explored. In addition, modification of length of the linker in D explored whether the distance between ring I and II is important for HAT activity. With respect to metabolic stability, the N atoms D can be dealkylated by microsomes (*J Pharmacol Toxicol Methods*, 1994. 31(4): p. 177-86; hereby incorporated by reference in its entirety). Amide groups can undergo hydrolysis by carboxylesterase enzymes (*Med Res Rev*, 2001. 21(5): p. 412-49; hereby incorporated by reference in its entirety).

Example 1—Designing and Synthesizing HAT Modulators

Modifications at C2: The ether/amino (I-g) can be obtained using the same synthesis scheme as in FIG. 5 (starting from 2-ethoxy-6-hydroxybenzoate or 2-amino-6-ethoxybenzoate esters). Mitsunobu reaction with an alcohol, in the presence of $PPh_3$ and DIAD, can provide a library of compounds. Should alcohols not be commercially available, corresponding halides will be engaged to carry out simple nucleophilic substitutions. The N,N-dimethylaminoethyl group at the C2 position of D was replaced with other groups. Substituents at the nitrogen such as piperidine (8), morpholine (9), piperazine (10), N-methylpiperazine (11), have been chosen to evaluate whether or not the enzymatic pocket can accommodate such groups (Scheme 1). Compounds 12-14 were synthesized to elucidate impact of increased in the chain length of the alkyl substituents at the N atom. Compound 15 was prepared to elucidate whether or not the nitrogen is important for HAT activity (Scheme 1).

Figure 6:
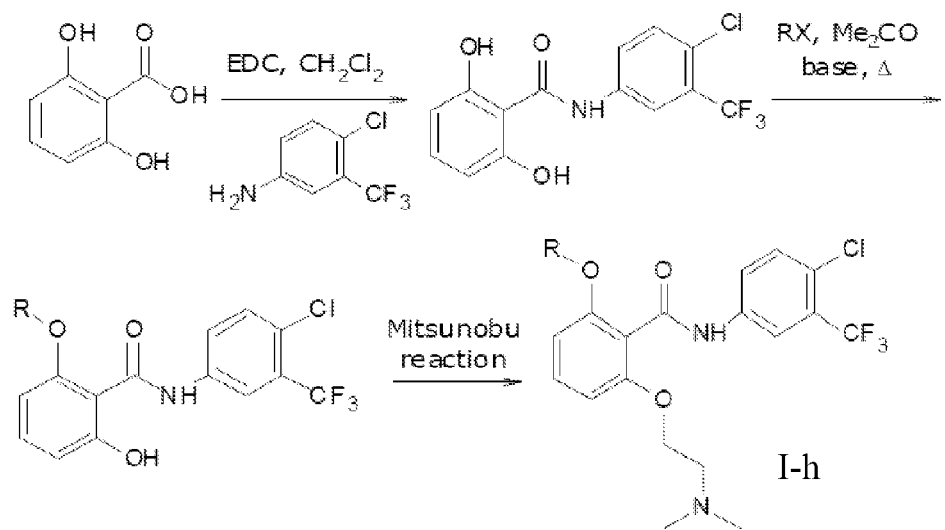
FIG. 6 is an exemplary synthetic scheme for compounds (I-h). Modifications at C6, where R is alkyl, cycloalkyl, alkenyl, heterocycle, aryl, heteroaryl, alkylamino, or cycloalkylamino.

Modifications at C6 (FIG. 6). D is described, for example, in WO 2011/072243 hereby incorporated by reference in its entirety). The amide is obtained by reaction of carboxylic acid with 4-chloro-3-(trifluoromethyl)aniline. Chemoselective monoalkylation of one phenol group should occur with halide in the presence of base in acetone (*Tetrahedron Letters*, 2010. 51: p. 495-498; hereby incorporated by reference in its entirety). Subsequent reaction with 2-chloro-N,N-dimethylethanamine, according to Mitsunobu conditions, gives derivative (I-h).

Figure 7:
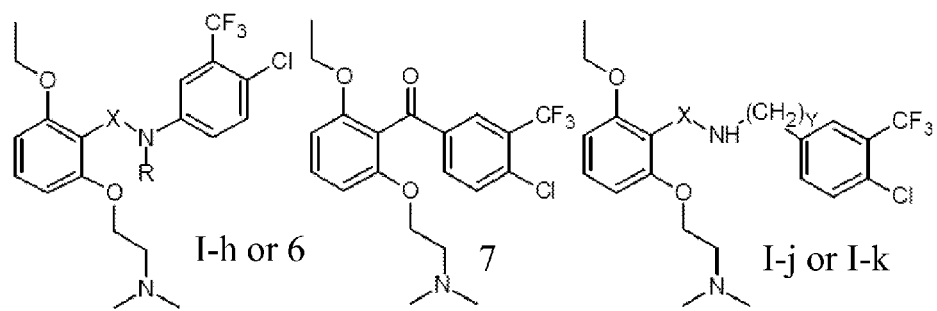
FIG. 7 are exemplary structures showing modifications at linker between I and II rings. For compound (I-i), X is CO, R is H, alkyl, cycloalkyl, heterocycle, aryl, heteroaryl, or substituted aryl and heteroaryl; For compound 6, X is $CH_2$, R is H; For compound (I-j), X is $CH_2CO$, R is H, Y is 0-3; For compound (I-k), X is CO, R is H, Y is 1-3.

Modifications at linker between I and II rings: N-substitution of amide group (I-i), reduction of amide into amine group (6) and shortening/lengthening of linker between the two aromatic rings [7, (I-j), and (I-k)] will be explored (FIG. 7). (I-i) and (I-k) can be obtained following the same synthetic scheme used for D (WO 2011/072243 hereby incorporated by reference in its entirety) but using different amines; N,N-disubstituted amines provide (I-i) while N-monosubstituted amines give (I-k). Amine 6 was prepared after reduction of the amide group of D (*J. Org. Chem.*, 1977. 42: p. 2082-2087; hereby incorporated by reference in its entirety). After Mitsunobu reaction with 2-(dimethyl-amino)ethanol and the subsequent reaction with 4-bromo-2-chloro-1-(trifluoromethyl)benzene in the presence of $^n$BuLi, 7 was obtained (*J. Org. Chem.*, 2006. 71: p. 4992-4995; hereby incorporated by reference in its entirety). (I-j) can be synthesized in 3 steps starting from 4-hydroxybenzofuranone, which provides its O-alkylated derivative by a nucleophilic substitution reaction with $CH_3CH_2I$. The lactone opening-ring of O-alkylated derivative and the amide bond formation can be carried out directly by using amine in the presence of reducing agent in pyridine (WO 2009/115707, PTC/FR2009/000233; each hereby incorporated by reference in its entirety). Such a reaction can be also performed without reducing agents (*Eur. J. Org. Chem.*, 2008: p. 655-672; hereby incorporated by reference in its entirety). Then, Mitsunobu reaction can give amide (I-j). Compound 16 contains a methylene group in the linker, and was synthesized using 4-chloro-3-(trifluoromethyl)benzylamine in the second step of the synthetic scheme for D as shown above (Scheme 2). The reduction of D by using a reducing agent gave the imine 17 (Scheme 3).

Figure 8:
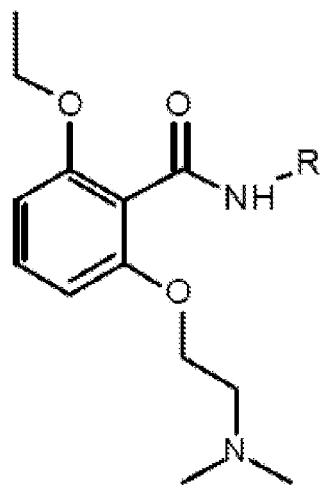
FIG. 8 is an exemplary structure showing modifications at the II ring, where R is a substituted aryl and heteroaryl for compound (I-l).

Modifications at II ring (FIG. 8): This modification strategy involves the replacement of II ring with other substituted aromatic or heterocyclic rings (I-l). Similar to D preparation, these compounds can be synthesized by using requisite amine in the second step of reaction.

Figure 9:
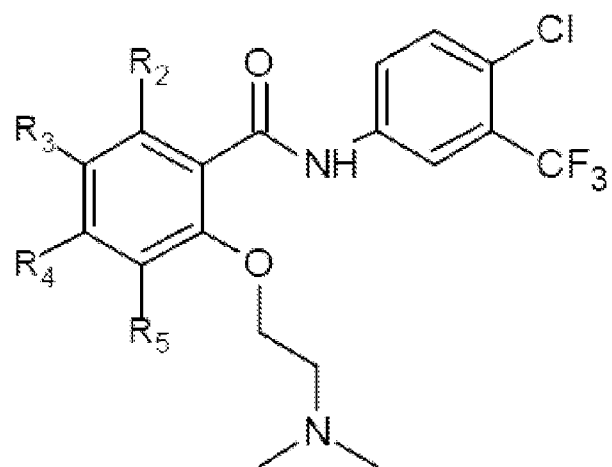
FIG. 9 is an exemplary structure showing modifications at the I ring. For compound 1, $R^2$ is ethoxyl, $R^3$ is H, $R^4$ is methyl, $R^5$ is H; For compound 2, $R^2$ is ethoxyl, $R^3$ is Cl, $R^4$ is H, $R^5$ is Cl; For compound 3, $R^2$ is H, $R^3$ is ethoxyl, $R^4$ is H, $R^5$ is H; For compound 4, $R^2$ is H, $R^3$ is H, $R^4$ is ethoxyl, $R^5$ is H.

Modifications at I ring (FIG. 9): Similar to the procedure shown on FIG. 6, 1 was prepared starting from 2,6-dihydroxy-4-methyl benzoic acid while 2 was synthesized using the D synthetic procedure, except that it required initial chlorination of the I ring. Compounds 3 and 4 bearing an ethoxyl group at W and Z, respectively were also synthesized. The synthesis of these two compounds follows D scheme of synthesis and starts from the corresponding commercially available esters ethyl 5-ethoxy-2-hydroxybenzoate and ethyl 4-ethoxy-2-hydroxybenzoate. Some of the structures in which the ethoxyl group has been moved from the 6-position to the 5- and 4-positions of ring I have also been prepared (18 and 19, respectively) (Scheme 4). Compounds 20 and 21 only have two substituents at ring I: with respect to D, 20 lacks an ethoxyl group while 21 bears an ethoxyl group instead of an N,N-dimethylaminoethoxyl group (Scheme 5).

Figure 10:
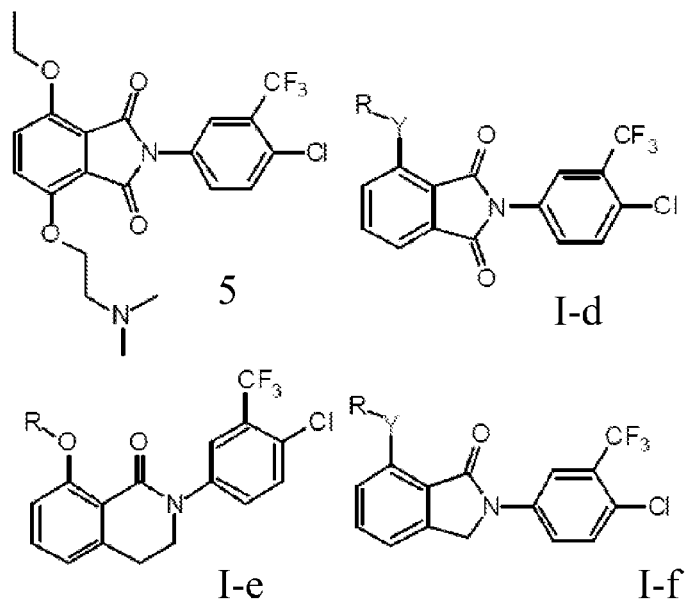
FIG. 10 are drawings of molecular structures that are constrained, where Y is O, or NH; and where R is ethyl, or 2-(dimethylamino)ethyl.
Figure 11:
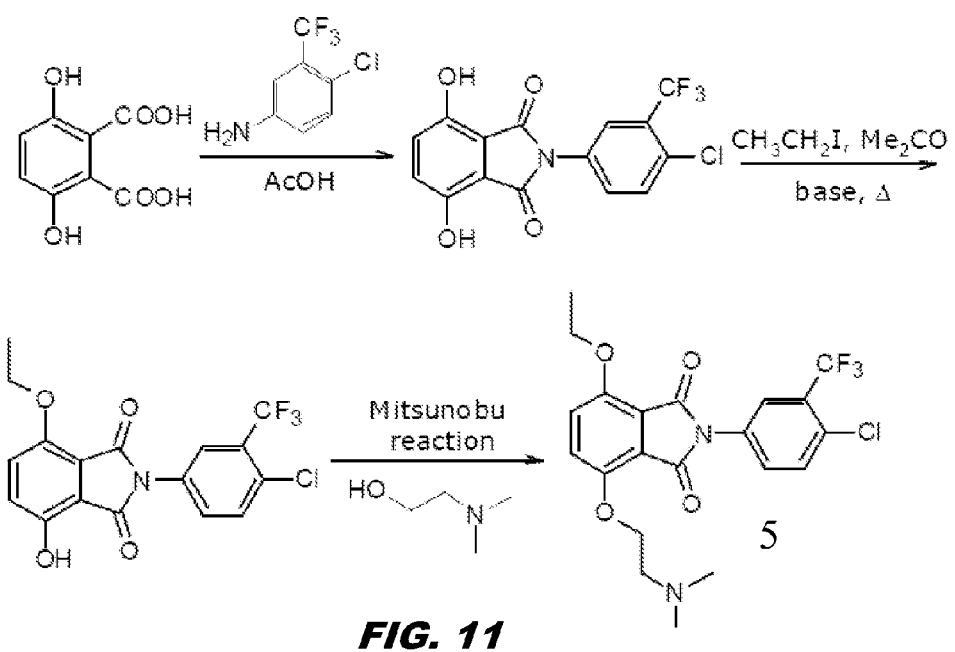
FIG. 11 is a synthetic scheme for compound 5.
Figure 12:
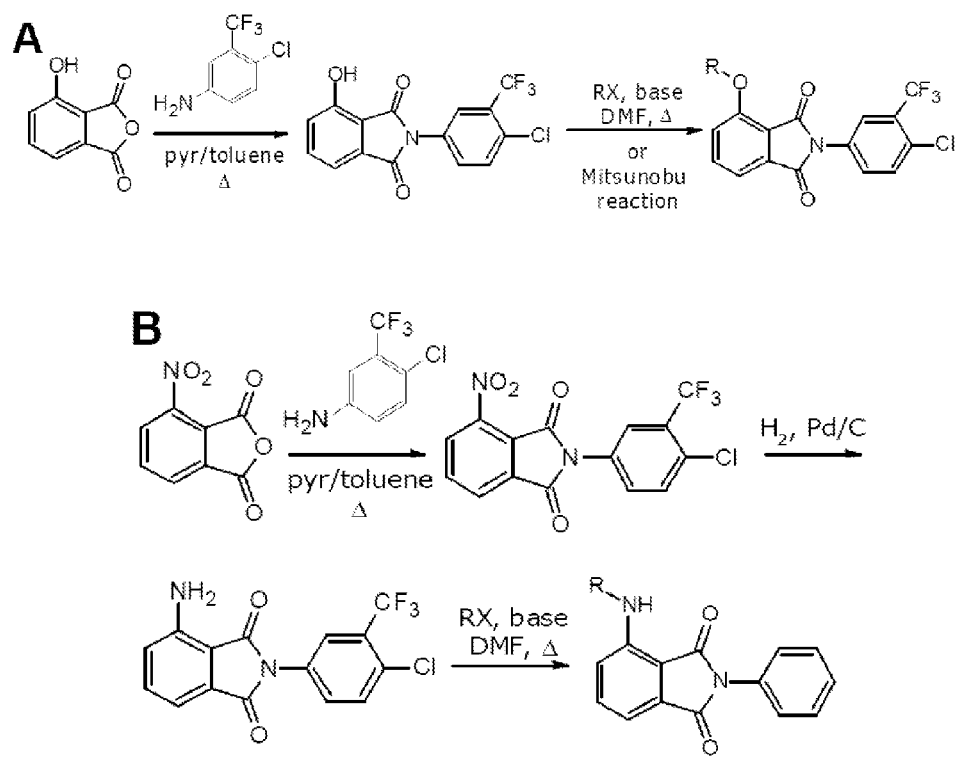
FIG. 12 shows the synthetic scheme for (I-d) compounds 3-alkyloxyphthalimide (FIG. 12A) and 3-aminophthalimide derivatives (FIG. 12B).

Constraining the molecular structure: Several structures [5, (I-d), (I-e), and (I-f)] that contain the amide group into a bicyclic ring have been designed (FIG. 10). This constriction blocks the free rotation bond between I ring and amide group and provides bicyclic scaffolds. Phthalimide derivative 5 bears di-substitution at the benzendicarboximide ring, while (I-d) has only one substitution. Synthesis of each can be carried out in a few steps (FIG. 11 and FIG. 12).

Isoquinolinone (I-e) can be prepared in two steps from commercially available 8-hydroxy-3,4-dihydro-1H-isochromen-1-one, which is converted in N-substituted 8-hydroxy-isochinolone by treatment with the corresponding amine in pyridine under refluxing conditions. Alkylation of hydroxyl group can provide the desired ligand (*Synthetic Communications*, 2010. 40: p. 666-676; hereby incorporated by reference in its entirety). Finally, phthalimidine (I-f) can be synthesized analagous to a published procedure (*Organic Process Research & Development*, 2009. 13: p. 1407-1412; hereby incorporated by reference in its entirety). Structures 23 and 24 that contain a maleimide moiety have been prepared (Scheme 7). Moreover, 22 bears a tertiary amine in place of the amide function (Scheme 6). This constriction blocks the free rotation bond between the I ring and the amide group and provides bicyclic scaffolds.

Example 1-1: (Scheme 1)

2-ethoxy-6-hydroxybenzoic acid, B

A solution of A (3.0 g) in ethanol (5 mL) was treated with a solution of NaOH 1N (15 mL). The solution was stirred to reflux for 6 h. After cooling the solution down, HCl conc. was added until acidic pH. The white precipitate was collected by filtration and dried under pressure to give 2.55 g of a white solid.

N-[4-chloro-3-(trifluoromethyl) phenyl]-2-ethoxy-6-hydroxybenzamide, (25)

N-(3-Dimethylaminopropyl)-N'-ethylcarbodiimide (EDC, 2.19 mL) was added to a solution of B (1.5 g) in methylene chloride (5 mL) at 0° C., and then 4-chloro-3-(trifluoromethyl) aniline (1.61 g) was added. The solution was stirred at room temperature for 24 h. The solvent was evaporated and the residue was dissolved in AcOEt (100 mL) and the organic layer was washed with a solution of HCl 6N (3×50 mL) and a solution of NaOH 20% (3×50 mL). The organic layer was dried over $Na_2SO_4$, filtered and evaporated. Compound 25 (2.2 g) was obtained by crystallization from MeOH.

Example 1-2: (Scheme 2)

N-[4-chloro-3-(trifluoromethyl) benzyl]-2-ethoxy-6-hydroxybenzamide, C

EDC (0.473 mL) was added to a solution of B (300.0 mg) and [4-chloro-3-(trifluoromethyl) phenyl] methanamine (0.243 mL) in 2 mL of methylene chloride at 0° C. The reaction was stirred overnight at room temperature. The solvent was evaporated and the desired product (371.0 mg) was isolated by crystallization from MeOH.

Example 1-3: (Scheme 1)

N-[4-chloro-3-(trifluoromethyl) phenyl]-2-ethoxy-6-[2-(piperidin-1-yl) ethoxy] benzamide, 8

Diisopropyl azodicarboxylate (DIAD, 0.14 mL) was added dropwise to a solution of 25 (200.0 mg), 2-(piperidin-1-yl) ethanol (0.096 mL) and triphenylphosphine ($PPh_3$, 188.8 mg) in THF (2 mL) at 0° C. The solution was stirred at room temperature for 24 h. The solvent was evaporated and the residue was diluted in AcOEt (30 mL) and washed with $H_2O$ (3×30 mL). The organic layer was dried over $Na_2SO_4$, filtered and evaporated. Purification by flash chromatography (10% MeOH in AcOEt) gave a colorless oil (145.0 mg). $^1$H NMR (CDCl$_3$, 300 MHz) δ 8.16 (s, 1H), 7.92-7.87 (m, 2H), 7.46 (d, 1H, J=8.4 Hz), 7.28 (t, 1H, J=8.4 Hz), 7.57 (m, 2H), 4.16 (t, 2H, J=5.4 Hz), 4.08 (q, 2H, J=6.9 Hz), 2.72 (t, 2H, J=5.4 Hz), 2.42 (m, 4H), 1.52-1.45 (m, 4H), 1.38 (t, 5H, J=6.9 Hz).

Example 1-4: (Scheme 1)

N-[4-chloro-3-(trifluoromethyl) phenyl]-2-ethoxy-6-(2-morpholinoethoxy) benzamide, 9

A suspension of 25 (200.0 mg), 4-(2-chloroethyl)-morpholine (124.1 mg) and $K_2CO_3$ (230.5 mg) in DMF (4 mL) was stirred at 80° C. for 24 h. The reaction mixture was diluted with AcOEt (20 mL) and washed with $H_2O$ (3×20 mL). The organic layer was dried over $Na_2SO_4$, filtered and evaporated. The crude product was purified by flash chromatography (10% MeOH in AcOEt) to provide 110 mg of desired product as a colorless oil. $^1$H NMR (CDCl$_3$, 300 MHz) δ 7.90 (s, 1H), 7.87 (s, 1H), 7.46 (t, 1H, J=8.4 Hz), 7.30 (d, 1H, J=8.4 Hz), 6.88 (t, 1H, J=8.7 Hz), 6.59 (t, 2H, J=9.0 Hz), 4.17 (t, 2H, J=5.4 Hz), 4.08 (q, 2H, J=6.9 Hz), 3.62 (t, 4H, J=4.5 Hz), 2.77 (t, 2H, J=5.4 Hz), 2.52 (t, 4H, J=4.5 Hz), 1.40 (t, 3H, J=6.9 Hz).

Example 1-5: (Scheme 4)

N-(4-chloro-3-(trifluoromethyl)phenyl)-5-ethoxy-2-hydroxybenzamide, G

EDC (0.73 mL) was slowly added to a solution of E (500.0 mg) and 4-chloro-3-(trifluoromethyl)aniline (508 mg) in DCM (5 mL) at 0° C. The reaction was stirred at room temperature for 24 h. The solvent was evaporated and the residue was dissolved in AcOEt (100 mL) and washed with HCl 4N (3×80 mL). The organic layer was dried over $Na_2SO_4$, filtered and evaporated to give a crude oil, which was purified by flash chromatography (hexane:AcOEt 1:2) to provide 380.0 mg of desired product as an off-white solid.

N-(4-chloro-3-(trifluoromethyl)phenyl)-2-(2-(dimethylamino)ethoxy)-5-ethoxybenzamide, 18

A mixture of G (350.0 mg) and $K_2CO_3$ (402.19 mg) in DMF (5 mL) was stirred for 30 minutes at 80° C. and then 2-chloro-N,N-dimethylethanamine hydrochloride (140.15 mg) was added. The reaction mixture was stirred at 80° C. for 24 h. After this time, the reaction was partitioned between AcOEt (30 mL) and $H_2O$ (30 mL) and the organic layer was washed with $H_2O$ (3×30 mL), dried over $Na_2SO_4$, filtered and evaporated. The crude product was purified by flash chromatography (10% MeOH in AcOEt) to provide 79.0 mg of 18 as a colorless solid. $^1$H NMR (CDCl$_3$, 300 MHz) δ 10.7 (s, 1H), 8.09 (dd, 1H, $J_1$=1.8, $J_2$=9.0 Hz), 8.01 (s, 1H), 7.79 (d, 1H, J=3.0 Hz), 7.45 (d, 1H, J=8.7 Hz), 7.06-7.02 (m, 1H), 6.96 (d, 1H, J=9.0 Hz), 4.22 (t, 2H, J=5.1 Hz), 4.07 (q, 2H, J=7.0 Hz), 2.77 (t, 2H, J=4.8 Hz), 2.29 (s, 6H), 1.42 (t, 3H, J=7.0 Hz).

Example 1-6: (Scheme 4)

N-(4-chloro-3-(trifluoromethyl)phenyl)-4-ethoxy-2-hydroxybenzamide, H

EDC (0.73 mL) was slowly added to a solution of F (500.0 mg) and 4-chloro-3-(trifluoromethyl)aniline (508 mg) in DCM (5 mL) at 0° C. The reaction was stirred at room temperature for 24 h. The solvent was evaporated and the residue was dissolved in AcOEt (100 mL) and washed with HCl 4N (3×80 mL). The organic layer was dried over $Na_2SO_4$, filtered and evaporated. The oily residue was purified by flash chromatography (hexane:AcOEt 1:2) to provide 490.0 mg of desired product as a sticky yellow solid.

N-(4-chloro-3-(trifluoromethyl)phenyl)-2-(2-(dimethylamino)ethoxy)-4-ethoxybenzamide, 19

A mixture of H (370 mg) and $K_2CO_3$ (426.46 mg) in DMF (5 mL) was stirred for 30 minutes at 80° C. and then 2-chloro-N,N-dimethylethanamine hydrochloride (148.16 mg) was added. The reaction mixture was stirred at 80° C. for 24 h. After this time, the reaction was partitioned between AcOEt (30 mL) and H$_2$O (30 mL) and the organic layer was washed with H$_2$O (3×30 mL), dried over Na$_2$SO$_4$, filtered and evaporated. The crude product was purified by flash chromatography (10% MeOH in AcOEt) to provide 33.0 mg of 19 as a waxy white solid. $^1$H NMR (CDCl$_3$, 300 MHz) δ 10.4 (s, 1H), 8.21 (d, 1H, J=9.3 Hz), 8.10 (dd, 1H, J$_1$=2.1, J$_2$=8.7 Hz), 7.96 (d, 1H, J=2.4 Hz), 7.43 (d, 1H, J=8.7 Hz), 6.64 (dd, 1H, J$_1$=2.4, J$_2$=9.0 Hz), 6.51 (d, 1H, J=2.1 Hz), 4.21 (t, 2H, J=5.7 Hz), 4.10 (q, 2H, J=6.9 Hz), 2.79 (t, 2H, J=5.1 Hz), 2.30 (s, 6H), 1.44 (t, 3H, J=6.9 Hz).

Example 1-7: (Scheme 2)

N-(4-chloro-3-(trifluoromethyl)benzyl)-2-ethoxy-6-hydroxybenzamide, C

EDC (0.437 mL) was slowly added to a solution of B (300.0 mg) and (4-chloro-3-(trifluoromethyl)phenyl)methanamine (0.243 mL) in DCM (5 mL) at 0° C. The reaction was stirred at room temperature overnight. The solvent was evaporated and the residue was dissolved in AcOEt (100 mL) and washed with HCl 4N (3×80 mL). The organic layer was dried over Na$_2$SO$_4$, filtered and evaporated. The desired product (371.0 mg) was obtained by crystallization from MeOH.

N-[4-chloro-3-(trifluoromethyl)benzyl]-2-(2-(dimethylamino)ethoxy)-6-ethoxybenzamide, 16

A mixture of C (200.0 mg) and K$_2$CO$_3$ (223.9 mg) in DMF (5 mL) was stirred for 30 minutes at 80° C. and then 2-chloro-N,N-dimethylethanamine hydrochloride (77.1 mg) was added. The reaction mixture was stirred at 80° C. for 24 h. After this time, the reaction was partitioned between AcOEt (30 mL) and H$_2$O (30 mL) and the organic layer was washed with H$_2$O (3×30 mL), dried over Na$_2$SO$_4$, filtered and evaporated. The crude product was purified by flash chromatography (MeOH in AcOEt 1:1) to provide 130.0 mg of desired product as an off-white solid. $^1$H NMR (CDCl$_3$, 300 MHz) δ 7.72 (d, 1H, J=2.1 Hz), 7.60-7.56 (m, 1H), 7.46 (d, 1H, J=8.1 Hz), 7.23 (d, 2H, J=8.7 Hz), 6.57 (d, 2H, J=8.4 Hz), 4.65 (d, 2H, J=6.6 Hz), 4.15 (t, 2H, J=6.0 Hz), 4.08 (q, 2H, J=6.9 Hz), 2.58 (t, 2H, J=6.0 Hz), 2.18 (s, 6H), 1.38 (t, 3H, J=6.9 Hz).

Example 1-8: (Scheme 1)

N-[4-chloro-3-(trifluoromethyl)phenyl]-2-ethoxy-6-[2-(piperazin-1-yl)ethoxy]benzamide, 10

DIAD (0.14 mL) was added dropwise to a solution of 25 (200.0 mg), 2-(piperazin-1-yl) ethanol (0.088 mL) and PPh$_3$ (188.8 mg) in THF (2 mL) at 0° C. The solution was stirred at room temperature for 24 h. The solvent was evaporated and the residue was diluted in AcOEt (30 mL) and washed with H$_2$O (3×30 mL). The organic layer was dried over Na$_2$SO$_4$, filtered and evaporated. Purification by flash chromatography (AcOEt:MeOH 1:1) gave a colorless oil (38.0 mg). $^1$H NMR (CDCl$_3$, 300 MHz) δ 7.90-7.85 (m, 3H), 7.46 (d, 1H, J=6.6 Hz), 7.30 (d, 1H, J=8.1 Hz), 6.60-6.55 (m, 2H), 4.15 (t, 2H, J=5.4 Hz), 4.08 (q, 2H, J=6.9 Hz), 2.79-2.72 (m, 5H), 2.48-2.45 (m, 5H), 1.37 (t, 3H, J=6.9 Hz).

Example 1-9: (Scheme 1)

N-[4-chloro-3-(trifluoromethyl)phenyl]-2-ethoxy-6-[2-(4-methylpiperazin-1-yl)ethoxy]benzamide, 11

DIAD (0.14 mL) was added dropwise to a solution of 25 (200.0 mg), 2-(4-methylpiperazin-1-yl)ethanol (0.103 mL) and PPh$_3$ (188.8 mg) in THF (2 mL) at 0° C. The solution was stirred at room temperature for 24 h. The solvent was evaporated and the residue was diluted in AcOEt (30 mL) and washed with H$_2$O (3×30 mL). The organic layer was dried over Na$_2$SO$_4$, filtered and evaporated. Purification by flash chromatography (AcOEt:MeOH 7:3) gave a white solid (38.0 mg). $^1$H NMR (CDCl$_3$, 300 MHz) δ 7.95-7.92 (m, 2H), 7.82 (s, 1H), 7.46 (d, 1H, J=9.0 Hz), 7.28-7.25 (m, 1H), 6.60-6.55 (m, 2H), 4.15 (t, 2H, J=5.4 Hz), 4.08 (q, 2H, J=6.9 Hz), 2.76 (t, 2H, J=5.4 Hz), 2.53 (s, 4H), 2.33 (s, 4H), 2.21 (s, 3H), 1.37 (t, 3H, J=6.9 Hz).

Example 1-10: (Scheme 1)

N-(4-chloro-3-(trifluoromethyl)phenyl)-2-(2-(diethylamino)ethoxy)-6-ethoxybenzamide, 12

DIAD (0.14 mL) was added dropwise to a solution of 25 (200.0 mg), 2-(diethylamino)ethanol (0.096 mL) and PPh$_3$ (188.8 mg) in THF (2 mL) at 0° C. The solution was stirred at room temperature for 24 h. The solvent was evaporated and the residue was diluted in AcOEt (30 mL) and washed with H$_2$O (3×30 mL). The organic layer was dried over Na$_2$SO$_4$, filtered and evaporated. Purification by flash chromatography (10% MeOH in DCM) gave 95.0 mg of light yellow oil. $^1$H NMR (CDCl$_3$, 300 MHz) δ 8.14 (s, 1H), 7.92-7.87 (m, 2H), 7.45 (d, 1H, J=8.7 Hz), 7.30-7.24 (m, 1H), 6.57 (dd, 2H, J$_1$=2.4, J$_2$=8.4 Hz), 4.13-4.04 (m, 4H), 2.82 (t, 2H, J=5.4 Hz), 2.58 (q, 4H, J=7.2 Hz), 1.37 (t, 3H, J=6.9 Hz), 0.95 (t, 6H, J=6.9 Hz).

Example 1-11: (Scheme 1)

N-[4-chloro-3-(trifluoromethyl)phenyl]-2-[3-(dimethylamino)propoxy]-6-ethoxybenzamide, 13

DIAD (0.14 mL) was added dropwise to a solution of 25 (200.0 mg), 2-(diethylamino)ethanol (0.084 mL) and PPh$_3$ (188.8 mg) in THF (2 mL) at 0° C. The solution was stirred at room temperature for 24 h. The solvent was evaporated and the residue was diluted in AcOEt (30 mL) and washed with H$_2$O (3×30 mL). The organic layer was dried over Na$_2$SO$_4$, filtered and evaporated. Purification by flash chromatography (10% MeOH in DCM) gave 83.0 mg of a waxy white solid. $^1$H NMR (CDCl$_3$, 300 MHz) δ 7.90 (s, 2H), 7.84 (s, 1H), 7.46 (d, 1H, J=9.0 Hz), 7.30-7.24 (m, 1H), 6.57 (dd, 2H, J$_1$=3.0, J$_2$=8.4 Hz), 4.11-4.04 (m, 2H), 2.42 (t, 2H, J=7.2 Hz), 2.16 (s, 6H), 1.97-1.88 (m, 2H), 1.37 (t, 3H, J=6.9 Hz).

Example 1-12: (Scheme 1)

N-[4-chloro-3-(trifluoromethyl)phenyl]-2-[3-(diethylamino)propoxy]-6-ethoxybenzamide, 14

DIAD (0.14 mL) was added dropwise to a solution of 25 (200.0 mg), 2-(diethylamino)ethanol (0.106 mL) and PPh$_3$ (188.8 mg) in THF (2 mL) at 0° C. The solution was stirred at room temperature for 24 h. The solvent was evaporated and the residue was diluted in AcOEt (30 mL) and washed with H$_2$O (3×30 mL). The organic layer was dried over Na$_2$SO$_4$, filtered and evaporated. Purification by flash chromatography (10% MeOH in DCM) gave 146.0 mg of a colorless oil. $^1$H NMR (CDCl$_3$, 300 MHz) δ 7.94-7.82 (m, 3H), 7.46 (d, 1H, J=8.7 Hz), 7.31-7.25 (m, 1H), 6.57 (d, 2H, J=8.4 Hz), 4.07 (t, 4H, J=6.6 Hz), 2.61 (t, 2H, J=7.2 Hz), 2.53 (q, 2H, J=6.9 Hz), 1.97-1.89 (m, 2H), 1.37 (t, 3H, J=6.9 Hz), 0.98 (t, 6H, J=7.2 Hz).

Example 1-13: (Scheme 3)

4-chloro-N-[2-(2-(dimethylamino)ethoxy)-6-ethoxybenzylidene]-3-(trifluoromethyl)aniline, 17

A solution of 80.0 mg of N-[4-chloro-3-(trifluoromethyl)phenyl]-2-[2-(dimethylamino)ethoxy]-6-ethoxybenzamide (D) in THF (2 mL) was treated with NaBH$_4$ (64.69 mg) at 0° C. After 10 minutes a solution of BF$_3$.OEt$_2$ (0.286 mL) was added dropwise. The resulting solution was stirred for 0.5 h at 0° C. and then 24 h at 60° C. The reaction mixture was concentrated under pressure and dissolved in AcOEt (20 mL) and washed with a saturated solution of NaHCO$_3$ (2×20 mL) and brine (20 mL). The organic layer was dried over Na$_2$SO$_4$, filtered and evaporated. Purification by flash chromatography (Hexane; AcOEt 2:1) provided 23.0 mg of desired product as a white solid. $^1$H NMR (CDCl$_3$, 300 MHz) δ 7.89 (s, 1H), 7.82 (d, 1H, J=8.7 Hz), 7.64 (s, 1H), 7.47 (d, 1H, J=8.7 Hz), 7.32 (t, 1H, J=8.4 Hz), 6.61 (dd, 2H, J$_1$=3.3, J$_2$=8.4 Hz), 4.44 (t, 2H, J=5.4 Hz), 4.09 (q, 2H, J=6.9 Hz), 3.14 (t, 2H, J=5.4 Hz), 2.63 (s, 6H), 1.37 (t, 3H, J=6.9 Hz).

Example 1-14: (Scheme 6)

2-[((4-chloro-3-(trifluoromethyl)phenyl)amino)methyl]-3-ethoxyphenol, 26

LAH was added portionwise at 0° C. to a solution of C (200.0 mg) in 2 mL of THF. The reaction was heated to reflux for 0.5 h and then quenched with AcOEt (1 mL) followed by Rochelle's salt. After 1 h of stirring at room temperature, the aqueous layer was removed and the organic layer was washed with H$_2$O (3×30 mL), dried over Na$_2$SO$_4$, filtered and evaporated to give an off-white solid (130.0 mg). 1H NMR (CDCl$_3$, 300 MHz) δ 7.25 (d, 1H, J=11.6 Hz), 7.12-7.06 (m, 2H), 6.85 (dd, 1H, J$_1$=3.6, J$_2$=11.6 Hz), 6.49-6.44 (m, 2H), 4.46 (s, 2H), 4.06 (q, 2H, J=7.0 Hz), 1.43 (t, 3H, J=7.0 Hz).

Example 1-15: (Scheme 5)

N-(4-chloro-3-(trifluoromethyl)phenyl)-2-hydroxybenzamide, K

A solution of J (1.0 g) and SOCl$_2$ in DCM (10 mL) was heated to reflux for 12 h. After this time 4-chloro-3-(trifluoromethyl)aniline (1.4 g) was added and the mixture was stirred at reflux for 4 h. The solvent was evaporated and the residue was dissolved in AcOEt (50 mL) and washed with HCl 2N (2×50 mL) and NaHCO$_3$ (2×50 mL). The organic layer was dried over Na$_2$SO$_4$, filtered and evaporated. The crude compound was treated with MeOH and the resulting white precipitate (300.0 mg) was collected by filtration.

N-[4-chloro-3-(trifluoromethyl)phenyl]-2-[2-(dimethylamino)ethoxy]benzamide, 20

DIAD (0.136 mL) was added dropwise to a solution of K (200.0 mg), 2-(diethylamino)ethanol (0.070 mL) and PPh$_3$ (180.0 mg) in THF (2 mL) at 0° C. The solution was stirred at room temperature for 24 h. The solvent was evaporated and the residue was diluted in AcOEt (30 mL) and washed with H$_2$O (3×30 mL). The organic layer was dried over Na$_2$SO$_4$, filtered and evaporated. Purification by flash chromatography (AcOEt) gave 80.0 mg of a white solid. $^1$H NMR (CDCl$_3$, 300 MHz) δ 10.61 (s, 1H), 8.27 (dd, 1H, J$_1$=1.8, J$_2$=7.8 Hz), 8.11 (dd, 1H, J$_1$=2.7, J$_2$=8.7 Hz), 7.98 (d, 1H, J=2.7 Hz), 7.49-7.43 (m, 2H), 7.14 (t, 1H, J$_1$=6.0 Hz), 7.02 (d, 1H, J$_2$=8.1 Hz), 4.27 (t, 2H, J=5.4 Hz), 2.80 (t, 2H, J=5.4 Hz), 2.31 (s, 6H).

Example 1-16: (Scheme 5)

N-(4-chloro-3-(trifluoromethyl)phenyl)-2-propoxybenzamide, 21

A suspension of K (100.0 mg), 85.69 mg of K$_2$CO$_3$ and iodoethane (0.025 mL) was heated to 80° C. for 24 h. The reaction was partitioned between AcOEt (30 mL) and H$_2$O (30 mL) and the organic layer was washed with H$_2$O (3×30 mL), dried over Na$_2$SO$_4$, filtered and evaporated to give the desired product (70.0 mg) as an off-white solid.

Example 1-17: (Scheme 1)

N-[4-chloro-3-(trifluoromethyl)phenyl]-2-ethoxy-6-(isopentyloxy)benzamide, 15

A mixture of 25 (200.0 mg) and K$_2$CO$_3$ (153.7 mg) in DMF (5 mL) was stirred for 30 minutes at 80° C. and then 1-bromo-3-methylbutane (77.1 mg) was added dropwise. The reaction mixture was stirred at 80° C. for 24 h. After this time, the reaction was partitioned between DCM (20 mL) and H$_2$O (20 mL) and the organic layer was washed with H$_2$O (3×30 mL), dried over Na$_2$SO$_4$, filtered and evaporated. The crude product was purified by flash chromatography (hexane:AcOEt 9:1) to provide 103.0 mg of desired product as an off-white solid. $^1$H NMR (CDCl$_3$, 300 MHz) δ 7.88 (d, 1H, J=8.4 Hz), 7.81 (s, 1H), 7.55 (s, 1H), 7.46 (d, 1H, J=8.4 Hz), 7.27 (t, 1H, J=8.4 Hz), 6.57 (d, 2H, J=8.4 Hz), 4.11-4.00 (m, 4H), 1.79-1.68 (m, 1H), 1.63 (q, 2H, J=6.3 Hz), 1.37 (t, 3H, J=6.9 Hz), 0.89 (d, 6H, J=6.3 Hz).

Example 1-18: (Scheme 6)

3-[4-chloro-3-(trifluoromethyl)phenyl]-5-ethoxy-3,4-dihydro-2H-benzo[e][1,3]oxazine, 22

A solution of 85.0 mg of 2-[((4-chloro-3-(trifluoromethyl)phenyl)amino)methyl]-3-ethoxyphenol (26) and 0.060 mL of formalin in EtOH (2 mL) was heated to reflux for 2.5 h. The reaction was diluted with H$_2$O (20 mL) and extracted with DCM (3×20 mL). The organic layer was dried over Na$_2$SO$_4$, filtered and evaporated. Purification by flash chromatography provided 33.0 mg of desired compound as a white solid. $^1$H NMR (CDCl$_3$, 300 MHz) δ 7.40 (d, 1H, J=3.0 Hz), 7.34 (d, 1H, J=9.0 Hz), 7.18 (dd, 1H, J=3.0, J$_2$=9.0 Hz), 7.07 (t, 1H, J=8.4 Hz), 6.44 (t, 2H, J=8.4 Hz), 5.29 (s, 2H), 4.54 (s, 2H), 4.03 (q, 2H, J=6.9 Hz), 1.42 (t, 3H, J=6.9 Hz).

Example 1-19: (Scheme 7)

2-(4-chloro-3-(trifluoromethyl)phenyl)-4-hydroxyisoindoline-1,3-dione, M

A solution of L (100.0 mg) and 4-chloro-3-(trifluoromethyl) aniline (142.9 mg) in AcOH (3 mL) was heated to reflux for 2 h. After cooling the reaction down, cold H$_2$O was added. The white precipitate (189.0 mg) was collected by filtration.

2-[4-chloro-3-(trifluoromethyl)phenyl]-4-ethoxy-isoindoline-1,3-dione, 23

A mixture of M (300.0 mg), iodoethane (0.140 mL) and K$_2$CO$_3$ (485.4 mg) was stirred at 80° C. for 8 h. The reaction was allowed to cool down and H$_2$O (10.0 mL) was added and the white precipitate (181.0 mg) was filtered. $^1$H NMR (CDCl$_3$, 300 MHz) δ 7.86 (s, 1H), 7.74 (t, 1H, J=7.2 Hz), 7.62 (d, 2H, J=2.1 Hz), 7.53 (d, 1H, J=7.2 Hz), 7.27 (d, 1H, J=8.4 Hz), 4.30 (q, 2H, J=6.9 Hz), 1.55 (t, 3H, J=6.9 Hz).

Example 1-20: (Scheme 7)

2-[4-chloro-3-(trifluoromethyl)phenyl]-4-[2-(dimethylamino)ethoxy]isoindoline-1,3-dione, 24

A mixture of M (300.0 mg), K$_2$CO$_3$ (485.4 mg) and 2-chloro-N,N-dimethylethanamine hydrochloride (252.9 mg) was stirred at 80° C. for 8 h. The reaction was allowed to cool down and was partitioned between H$_2$O (10.0 mL) and AcOEt (40 mL). The organic layer was washed with H$_2$O (3×30 mL), dried over Na$_2$SO$_4$, filtered and evaporated. Purification by flash chromatography (AcOEt:MeOH 2:1) gave the desired compound as a pale yellow oil. $^1$H NMR (CDCl$_3$, 300 MHz) δ 7.84 (s, 1H), 7.74 (t, 1H, J=7.2 Hz), 7.62 (d, 2H, J=2.1 Hz), 7.54 (d, 1H, J=7.5 Hz), 7.27 (d, 1H, J=8.1 Hz), 4.32 (t, 2H, J=5.4 Hz), 2.87 (t, 2H, J=5.41 Hz), 2.40 (s, 6H).

Example 2: Assays for HAT Affinity and Selectivity for CBP, PCAF, and P300

Compounds can be tested for HAT modulator activity using the HAT Assay kit from Active Motif (USA, CA). For this assay, the catalytic domain of human CBP, PCAF, p300 and GCN5 (Enzo Life Sci., USA) can be used. The catalytic domains for the remaining HATs can be produced using New England Biolabs *K. lactis* Protein Expression Kit. In addition to being potent activators of CBP and/or PCAF (EC$_{50}$<100 nM), the candidate compounds can also be selective. When assayed against all other HATs, they can show a 50-fold greater potency towards CBP and/or PCAF. The most potent/selective compounds that show efficacy in tests of synaptic and memory dysfunction outlined in Examples 4 and 5 can be assayed for selectivity against HDACs. While performing these tests, solubility can also be evaluated (neutral aqueous buffer >10 μg/ml).

Confirmation of in vitro data can be performed using a neuronal preparation. In particular, compounds can be assayed in primary cultures and adult mice. Whether the compounds can increase specific histone acetylation in 10 day old cultured hippocampal neurons (prepared as described in *Neuron*, 2004. 42(1): p. 129-41; hereby incorporated by reference in its entirety) can also be determined. Media can be aspirated and replaced with 0.5 mL of PBS containing the HAT activator. After 30 min at 37° C., cells can be removed and lysed for WB analysis. Selected compounds can also be tested in adult mice, following an assessment of acute toxicity to determine the dose of compound to be administered to the animal (see "toxicity tests" below). Testing in adult mice is useful as cell cultures do not mimic the whole body with complex cell-cell interactions and in vivo drug PK, BBB penetration, etc (see also Example 3 below). Animals can be treated with the HAT compound, hippocampi can be collected 30 min after the i.p. injection, and lysed for WB analysis. Experiments can be performed in triplicate.

On selected compounds, interactions with channels, receptors, transporters can be examined using the NIMH PDSP program (see http://pdsp.cwru.edu for a list of CNS targets; hereby incorporated by reference in its entirety), in addition to ADMET/Tox studies discussed in Example 3.

Example 3: Determination of Pharmacokinetic (PK) and Safety Profiles

Rudimentary PK properties and toxicity of the new HAT modulators can be determined. Pharmacokinetic assays can include the measurement of a) bioavailability and b) brain uptake. Mice can be i.p. injected with the compounds (for some compounds, PK tests can also be performed using p.o. and i.v. routes of administration). 5-6 mice/sex can be used for each time-point. For the assessment of bioavailability (concentration of compound in the blood as a function of time after administration), blood samples can be obtained from test animals following a single acute administration (collected at time intervals up to approximately 24 h). Blood can be harvested by retro-orbital puncture, collected in heparanized tubes, and plasma obtained by centrifugation. Samples can be analyzed by LC-MS to measure the amounts of the candidate compound and metabolites. An indication of brain uptake and BBB penetration can be obtained by tissue extraction of the candidate compound from brain. Brain homogenates can be centrifuged 11,000 rpm for 10 min. An aliquot of the sample can be added to acetonitrile, then injected onto LC-MS/MS for analysis. Similar patterns of brain and plasma concentrations can be indicative of brain uptake as a reflection of concentration in the blood. A peak brain/blood concentration ratio >1 can indicate that brain uptake comparable with that of known CNS drugs in clinical use. For example, the brain/blood ratio for minaprine, a 6-phenylaminopyridazine CNS drug, is >2 (*Xenobiotica*, 1985. 15(12): p. 1111-9; herein incorporated by reference in its entirety).

Acute toxicity can also be evaluated. All clinical signs, time of onset, duration, reversibility of toxicity and mortalities can be recorded. Animals can be observed periodically during the first 24 hrs with continuous monitoring given to the first 4 hrs, then at least once a day for 14 days or until they die to check food and liquid intake, weight, as well as locomotion and exploratory behavior. Maximum tolerated dose (MTD) and chronic toxicity can also be evaluated. MTD can be computed as the maximum administered dose that does not produce any toxicity effect in terms of malaise or death (body weight will be monitored over time). Chronic toxicity can be assessed at the MTD. All clinical signs, time of onset, duration, reversibility of toxicity and mortalities can also be recorded. The occurrence of chronic toxicity signs can be assessed for at least 1 month after the end of the treatment.

It has been estimated that over half of all drugs fail to reach the market because of ADMET problems (*Nat Biotechnol*, 2001. 19(8): p. 722-6; herein incorporated by reference in its entirety). Therefore, before embarking on a course of costly animal toxicological work and following efficacy assessment (see Examples 4 and 5), recent advances in in vitro ADMET testing can be used to screen selected compounds with a quick, inexpensive battery of assays. Two areas that have resulted in the withdrawal of many drugs from the market can be evaluated: drug-drug interactions (liver metabolism), hERG channel blockage (cardiac dysfunction). To test for drug-drug interactions related to hepatotoxicity, the Cytochrome P450 inhibition assay can be performed (performed by SRI international). Additionally, hERG channel blockage assay can be performed using the NIMH PDSP program.

Example 4: Selecting HAT Modulators that Rescue LTP in APP/PS1 Mice

Synaptic dysfunction is a major hallmark of AD (*Histol Histopathol*, 1995. 10(2): p. 509-19; herein incorporated by reference in its entirety). An aspect of the drug screening protocol can include a measurement of the effect of compounds onto synaptic function. The APP/PS1 mouse presents an impairment of LTP by the age of 3 months (*Ann Neurol*, 2004. 55(6): p. 801-14; herein incorporated by reference in its entirety), and therefore permits a relatively fast assessment of synaptic function without waiting a long time for mice aging. LTP can be examined because it is a type of synaptic plasticity thought to underlie learning and memory. D rescues the Aβ-induced reduction of LTP, and other compounds can also be screened to identify those that can re-establish normal LTP. The compounds can be applied for 30 min. Controls can be performed on slices from APP/PS1 mice treated with vehicle, and WT mice treated with compound or vehicle. If the compounds re-establish normal LTP in APP/PS1 slices, one can conclude that the compounds rescue impairment of synaptic plasticity in APP/PS1 mice. Cognitive impairment can also be investigated (see Example 5).

Animals: Tg mice can be obtained by crossing APP (K670M:N671L) with PS1(M146L) (line 6.2) animals. The genotype can be identified by PCR on tail samples (*Nature*, 1996. 383(6602): p. 710-3; *Science*, 1996. 274(5284): p. 99-102; *J Mol Neurosci*, 2002. 19(1-2): p. 135-41; each hereby incorporated by reference in its entirety).

Electrophysiology can be performed on males (see description in *Cell*, 2006. 126(4): p. 775-88; hereby incorporated by reference in its entirety).

Statistical Analyses: see Example 5.

Example 5: Screening for Amelioration of Cognitive Abnormalities in APP/PS1 Mice Treatment with a new HAT modulator indicated by Example 4 will study rescue of cognitive deficits in 3 and 6 month old APP/PS1 mice. As behavioral tasks, the RAWM and contextual FC will be used, two types of tests that assess different types of memory (reference ad associative) that are affected in AD patients. The treatment can be performed with the same timing (i.e. 30 min before training for fear conditioning or before the $1^{st}$ and $2^{nd}$ group of tests for the RAWM). Conditions to be tested can include: APP/PS1 and WT treated with HAT activators, APP/PS1 and WT treated with vehicle. After behavioral testing, mice can be sacrificed and their blood and brains used for Aβ level, Tau protein, TARDBP and TDB levels, and alpha-synuclein measurements. As a control for effectiveness of HAT modulator, hippocampal acetyl-H4 levels can be measured after administration of the compounds 30 min prior to training for fear conditioning and removal of the hippocampi 1 hr after the electric shock (APP/PS1 mice have been shown to have a reduction of acetylated H4 after the electric shock (*J Alzheimers Dis*, 2009. 18(1): p. 131-9; hereby incorporated by reference in its entirety). Further screening can include assays focusing on two areas that have resulted in the withdrawal of many drugs from the market: drug-drug interactions, hERG channel blockage (see Example 3).

Animals: see Example 4.

Behavioral Studies: Experiments can be performed in blind only on male animals to reduce variability. A) Spatial memory. This type of reference memory will be studied with the 2-day RAWM test, as described (*Nat Protoc*, 2006. 1(4): p. 1671-9; hereby incorporated by reference in its entirety). The task is a hybrid of the Morris Water Maze (MWM) and the radial arm land maze. For these experiments, visible platform testing can be conducted to exclude that visual, motor and motivation deficits affect the mouse performance, as described (*Ann Neurol*, 2004. 55(6): p. 801-14; hereby incorporated by reference in its entirety). B) Fear Conditioning to examine both contextual and cued learning will be assessed as described (*J. Clin. Invest.*, 2004. 114: p. 1624-1634; hereby incorporated by reference in its entirety). For these experiments, threshold assessment test can be performed to check sensory perception of electric foot in different groups of mice (*J. Clin. Invest.*, 2004. 114: p. 1624-1634; hereby incorporated by reference in its entirety). In addition, the open-field test can be conducted to evaluate exploratory as described (*Neuroscience*, 2007. 147(1): p. 28-36; *J Neurosci*, 2008. 28(53): p. 14537-45; each hereby incorporated by reference in its entirety).

Histone acetylation assay: Western blot can be performed from snap-frozen in liquid nitrogen hippocampi. Tissue can be homogenized in RIPA buffer, then sonicated before centrifugation at 10,000 rpm for 5 min. Whole cell extracts can be electrophoresed on 10-20% gradient PAGE gel (Invitrogen) and then immunoblotted. Antibodies can be used at a 1:1,000 concentration for immunoblotting. All anti-histone antibodies can be purchased from Millipore. Immunoblot data can be quantified by measuring the band intensity using imaging software (NIH ImageJ).

Determination of Aβ levels can be performed on homogenates of frozen hemi-brains and plasma as previously described (*Ann Neurol*, 2004. 55(6): p. 801-14; hereby incorporated by reference in its entirety).

Determination of alpha-synuclein levels can be performed on homogenates of frozen hemi-brains using an α-Synuclein ELISA Kit (Catalog # NS400; Millipore, Billerica, Mass.) according to manufacturer's instructions.

Determination of TARDBP/TDP-43 levels can be performed on homogenates of frozen hemi-brains using a Human TAR DNA binding protein 43, TARDBP/TDP-43 ELISA Kit (Catalog # E1951h; Wuhan EIAab Science Co, Wuhan, China) according to manufacturer's instructions.

Determination of total Tau and phosphorylated Tau (Thr 231) levels can be performed on homogenates of frozen hemi-brains and plasma using assay and kits according to manufacturer's instructions available from MesoScale Discovery (Gaithersburg, Md.) (see http://www.mesoscale.com/catalogsystemweb/webroot/products/assays/alzheimers.aspx; hereby incorporated by reference in its entirety).

Statistics: Experiments involving mice can be performed in blind. Results can be expressed as Standard Error Mean (SEM). Level of significance can be set for p<0.05. Results can be analyzed with ANOVA with post-hoc correction with drug or genotype as main effect.

Example 6: Screening for Amelioration of Cognitive Abnormalities in Mouse Models for Huntington's Disease Treatment with a HAT compound indicated by Example 13 to assess whether the compound can rescue the cognitive deficits in a mouse model of Huntington's Disease (e.g., FVB-Tg(YAC128)53Hay/J and FVB/NJ-Tg(YAC72)2511Hay/J mice, available from the Jackson Laboratory, Bar Harbor Me.) can be examined. As behavioral tasks, the RAWM and contextual FC can be employed, two types of tests assessing different types of memory (reference ad associative). The treatment can be performed with the same timing (i.e. 30 min before training for fear conditioning or before the $1^{st}$ and $2^{nd}$ group of tests for the RAWM). Conditions to be tested can include: Huntington's Disease mice and WT treated with HAT modulator, Huntington's Disease mice and WT treated with vehicle. After behavioral testing mice can be sacrificed and their blood and brains used for Huntingtin protein level measurement. As a control for effectiveness of HAT modulation, hippocampal acetyl-H4 levels can be measured after administration of the compounds 30 min prior to training for fear conditioning and removal of the hippocampi 1 hr after the electric shock. Assays focusing on two areas that have resulted in the withdrawal of many drugs from the market can also be employed: drug-drug interactions, hERG channel blockage (see Example 3).

Animals: Mouse models of Huntington's Disease (e.g., FVB-Tg(YAC128)53Hay/J [Stock no. 004938] and FVB/NJ-Tg(YAC72)2511Hay/J mice [Stock no. 003640]) can be obtained from the Jackson Laboratory (Bar Harbor Me.). See also, Hodgson et al., (May 1999) *Neuron*, Vol. 23, 181-192; hereby incorporated by reference in its entirety.

Behavioral Studies: Experiments can be performed in blind only on male animals to reduce variability. A) Spatial memory. This type of reference memory can be studied with the 2-day RAWM test, as described (*Nat Protoc,* 2006. 1(4): p. 1671-9; hereby incorporated by reference in its entirety). The task is a hybrid of the Morris Water Maze (MWM) and the radial arm land maze. For these experiments, visible platform testing can be conducted to exclude that visual, motor and motivation deficits affect the mouse performance, as described (*Ann Neurol,* 2004. 55(6): p. 801-14; hereby incorporated by reference in its entirety). B) Fear Conditioning to examine both contextual and cued learning can be assessed as described (*J. Clin. Invest.,* 2004. 114: p. 1624-1634; hereby incorporated by reference in its entirety). For these experiments, threshold assessment test can performed to check sensory perception of electric foot in different groups of mice (*J. Clin. Invest.,* 2004. 114: p. 1624-1634; hereby incorporated by reference in its entirety). In addition, the open-field test can be conducted to evaluate exploratory as described (*Neuroscience,* 2007. 147(1): p. 28-36; *J Neurosci,* 2008. 28(53): p. 14537-45; each hereby incorporated by reference in its entirety).

Histone acetylation assay: Western blot can be performed from snap-frozen in liquid nitrogen hippocampi. Tissue can be homogenized in RIPA buffer, then sonicated before centrifugation at 10,000 rpm for 5 min. Whole cell extracts can be electrophoresed on 10-20% gradient PAGE gel (Invitrogen) and then immunoblotted. Antibodies can be used at a 1:1,000 concentration for immunoblotting. All anti-histone antibodies can be purchased from Millipore. Immunoblot data can be quantified by measuring the band intensity using imaging software (NIH ImageJ).

Determination of huntingtin levels can be performed on homogenates of frozen hemi-brains and plasma using a Huntingtin (Htt) ELISA Kit (Catalog # ABIN423526; Antibodies-online, Atlanta, Ga.) according to manufacturer's instructions.

Statistics: Experiments on mice can be performed in blind. Results can be expressed as Standard Error Mean (SEM). Level of significance can be set for $p<0.05$.

Results can be analyzed with ANOVA with post-hoc correction with drug or genotype as main effect.

Example 7: Screening for Amelioration of Cognitive Abnormalities in Mouse Models for Parkinson's Disease Parkinson's Disease (PD) is a degenerative disease with a neuronal death up to 75-95% of the dopamine neurons in the substantia nigra nucleus. Treatment with a HAT modulator compound indicated by Example 4 to assess rescue of abnormal motor movements in a mouse model of PD (e.g., see Parkinson's Disease mice models available from the Jackson Laboratory, Bar Harbor Me. at http://jaxmice.jax.org/list/ra1594.html; see also Emborg, *Journal of Neuroscience Methods* 139 (2004) 121-143; Lane, *Psychopharmacology* (2008) 199:303-312; and Meredith et al., *Acta Neuropathol* (2008) 115:385-398; each hereby incorporated by reference in its entirety) can be assessed. Behavioral tasks, for example, dyskinesia, bradykinesia, tremor, and/or grip force for the evaluation of the compound's efficacy, can be examined at various stages of PD. Conditions to be tested can include: PD mice and WT treated with HAT modulator, PD mice and WT treated with vehicle. After behavioral evaluation, mice can be sacrificed and their brains used for aggregated alpha-synuclein protein measurement. As a control for effectiveness of HAT modulation, hippocampal acetyl-H4 levels can be measured.

Animals: Mouse models of Parkinson's Disease can be obtained from the Jackson Laboratory (Bar Harbor Me.). See also, Meredith et al., *Acta Neuropathol* (2008) 115:385-398; hereby incorporated by reference in its entirety).

Behavioral Studies: Experiments can be performed in blind only on male animals to reduce variability, according to methods described by Fleming et al., ((2004) The Journal of Neuroscience, 24(42):9434-9440) and Hwang et al., ((2005) The Journal of Neuroscience, 25(8):2132-2137; each hereby incorporated by reference in its entirety).

Histone acetylation assay: Western blot can be performed from snap-frozen in liquid nitrogen hippocampi. Tissue can be homogenized in RIPA buffer, then sonicated before centrifugation at 10,000 rpm for 5 min. Whole cell extracts can be electrophoresed on 10-20% gradient PAGE gel (Invitrogen) and then immunoblotted. Antibodies can be used at a 1:1,000 concentration for immunoblotting. All anti-histone antibodies can be purchased from Millipore. Immunoblot data can be quantified by measuring the band intensity using imaging software (NIH ImageJ).

Determination of alpha-synuclein levels can be performed on homogenates of frozen hemi-brains using an α-Synuclein ELISA Kit (Catalog #NS400; Millipore, Billerica, Mass.) according to manufacturer's instructions or via standard neuropathological methods (brain tissue histology).

Statistics: Experiments in mice can be performed in blind. Results can be expressed as Standard Error Mean (SEM). Level of significance can be set for $p<0.05$. Results can be analyzed with ANOVA with post-hoc correction with drug or genotype as main effect.

Example 8: Biological Screening of Compounds

Figure 13:
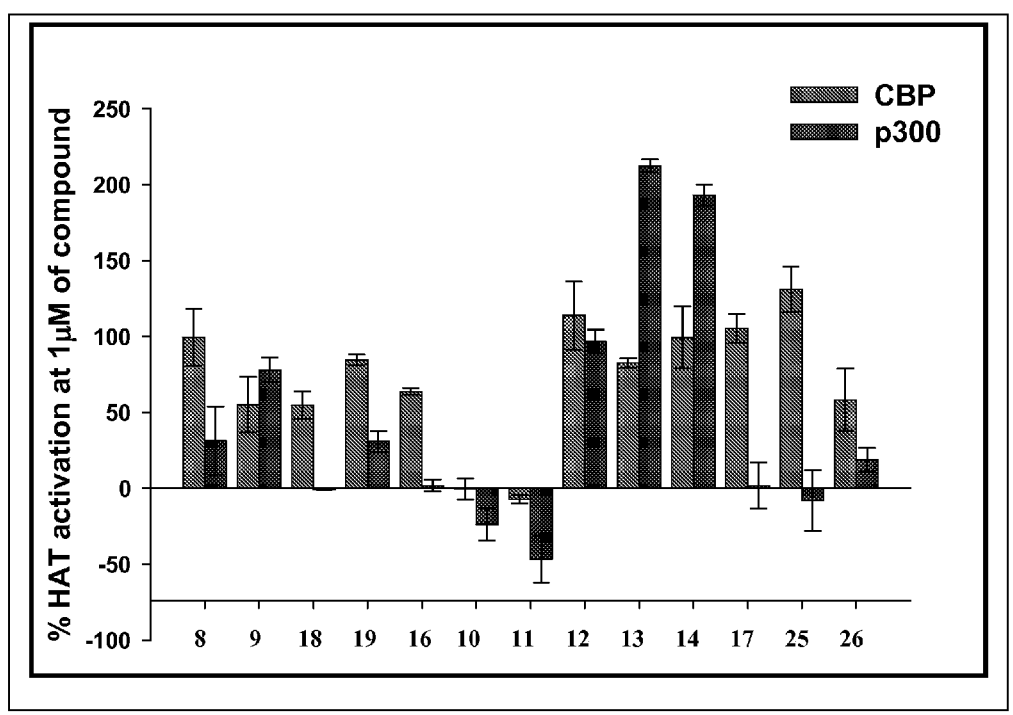
FIG. 13 shows in vitro measurements of HAT enzymatic activity for selected compounds.

Commercial human HATs (CBP, p300, GCN5, PCAF (Enzo Life Sciences), and Tip60 (SignalChem)) were assayed in an acetyltransferase activity assay (Enzo Life Sciences, Cat. No. ADI-907-026). Each well contained, in addition to a HAT, histone 3 as the acetyl acceptor, acetyl-CoA as the acetyl donor in the reaction mixture and compounds (1% DMSO) at the appropriate concentrations. The reaction was carried out at room temperature. Enzyme activity was measured by monitoring the breakage of the substrate acetyl-CoA by HAT using a proprietary detection mixture. The fluorescent signal was measured using a Tecan microplate reader (excitation: 380 nm, emission: 520 nm). The assay methodology was adopted as it provided a 10-fold higher signal/background ratio and was more sensitive than other assays. Using this method, the $EC_{50}$ values of D for CBP (4.5 nM) and Tip60 (>200 μM) were established. Initial screening revealed that compounds such as 8, 9, 12-14, and 19 behave as activators with respect to CBP and P300. Compounds 16, 17, 18, 25 and 26 activated only CBP, whereas 11 inhibited P300 and had no effect on CBP. Compound 10 had no effect with either P300 or CBP (FIG. 13).

Representative compounds exhibited EC50 values for activation of P300 of about 3 nM or less. EC50 values for some compounds are provided in Table 1.

TABLE 1

EC50 Values for Selected Compounds

| Compound | EC50 (nM) |
|---|---|
| D | 3.81 |
| 8 | 2.75 |
| 9 | 2.07 |
| 10 | 2.10 |
| 11 | 2.28 |
| 12 | 1.47 |
| 13 | 1.32 |
| 16 | 1.84 |
| 18 | 2.30 |
| 19 | 1.85 |

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:
1. A compound of any one of the formulae below:

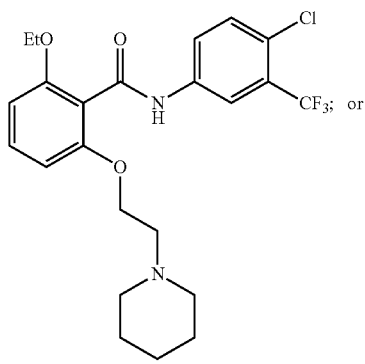
(8)

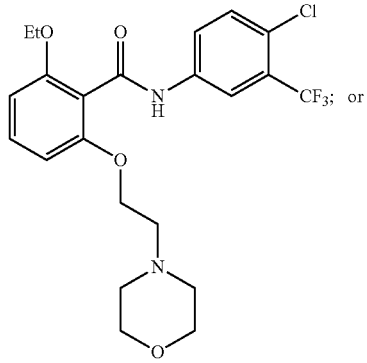
(9)

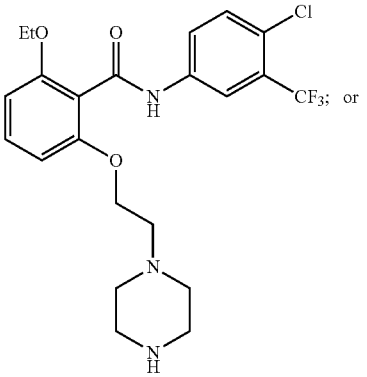
(10)

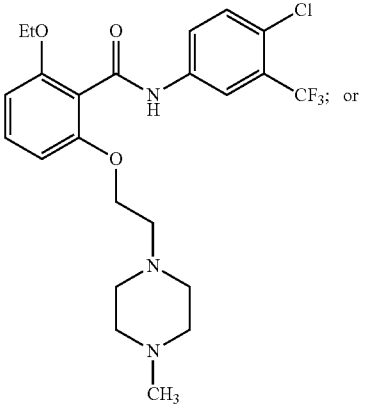
(11)

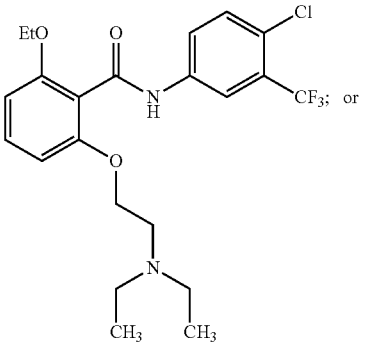
(12)

-continued

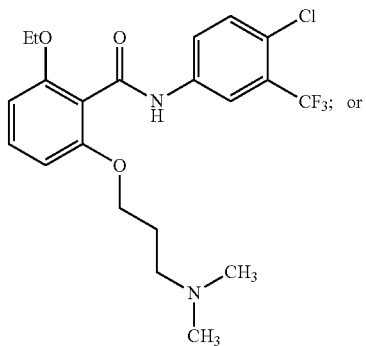

(13)

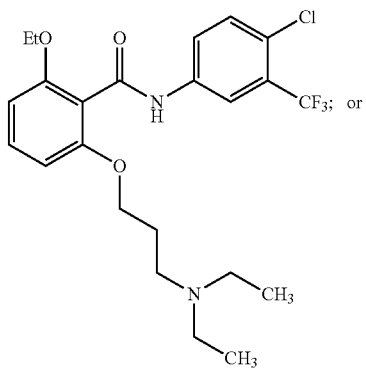

(14)

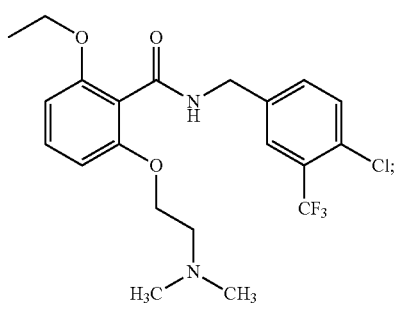

(16)

or a pharmaceutically acceptable salt thereof.

2. The compound of claim 1, wherein the compound is:

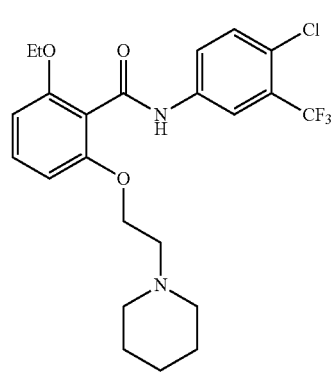

(8)

or a pharmaceutically acceptable salt thereof.

3. A pharmaceutical composition, comprising a compound of claim 1, or a pharmaceutically acceptable salt thereof and at least one pharmaceutically acceptable carrier.

4. A pharmaceutical composition, comprising a compound of claim 2, or a pharmaceutically acceptable salt thereof and at least one pharmaceutically acceptable carrier.

5. The compound of claim 1, wherein the compound is:

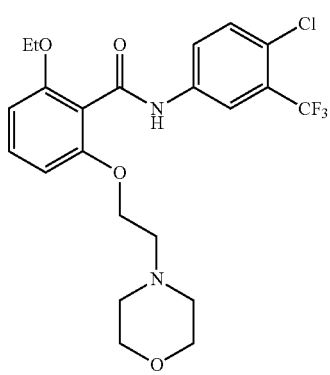

(9)

or a pharmaceutically acceptable salt thereof.

6. The compound of claim 1, wherein the compound is:

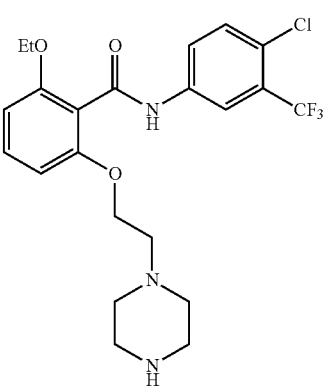

(10)

or a pharmaceutically acceptable salt thereof.

7. The compound of claim 1, wherein the compound is:

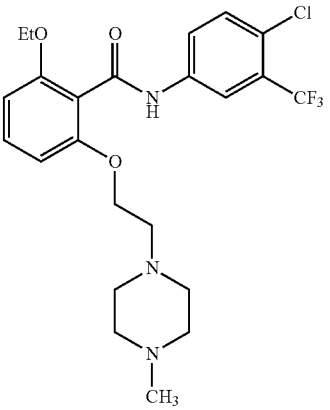

(11)

or a pharmaceutically acceptable salt thereof.

8. The compound of claim 1, wherein the compound is:

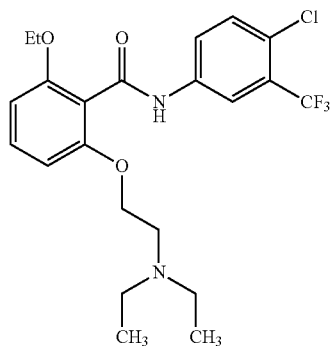
(12)

or a pharmaceutically acceptable salt thereof.

9. The compound of claim 1, wherein the compound is:

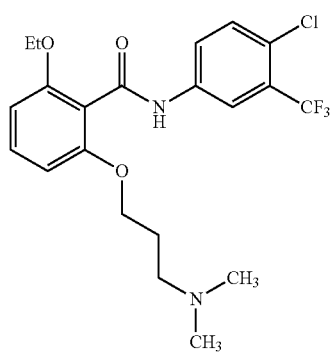
(13)

or a pharmaceutically acceptable salt thereof.

10. The compound of claim 1, wherein the compound is:

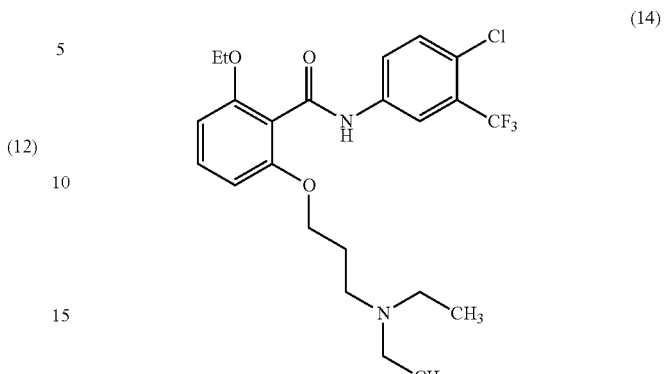
(14)

or a pharmaceutically acceptable salt thereof.

11. The compound of claim 1, wherein the compound is:

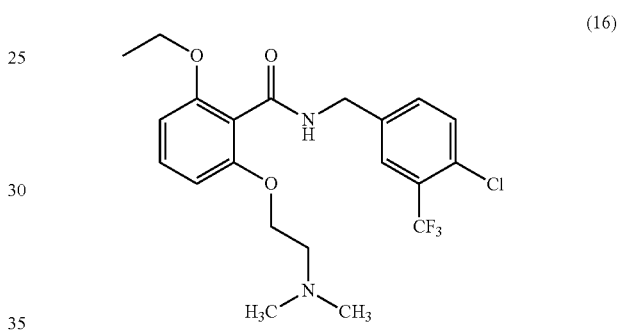
(16)

or a pharmaceutically acceptable salt thereof.

12. A pharmaceutical composition, comprising the compound of claim 5, and at least one pharmaceutically acceptable carrier.

13. A pharmaceutical composition, comprising the compound of claim 6, and at least one pharmaceutically acceptable carrier.

14. A pharmaceutical composition, comprising the compound of claim 7, and at least one pharmaceutically acceptable carrier.

15. A pharmaceutical composition, comprising the compound of claim 8, and at least one pharmaceutically acceptable carrier.

16. A pharmaceutical composition, comprising the compound of claim 9, and at least one pharmaceutically acceptable carrier.

17. A pharmaceutical composition, comprising the compound of claim 10, and at least one pharmaceutically acceptable carrier.

18. A pharmaceutical composition, comprising the compound of claim 11, and at least one pharmaceutically acceptable carrier.

* * * * *